US008748571B2

(12) United States Patent
Liu et al.

(10) Patent No.: US 8,748,571 B2
(45) Date of Patent: *Jun. 10, 2014

(54) THROMBOPOIETIC COMPOUNDS

(75) Inventors: Chuan-Fa Liu, Waltham, MA (US); Ulrich Feige, Benglen (CH); Janet C. Cheetham, Montecito, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/278,137

(22) Filed: Oct. 20, 2011

(65) Prior Publication Data
US 2012/0034657 A1 Feb. 9, 2012

Related U.S. Application Data

(60) Division of application No. 10/933,133, filed on Sep. 2, 2004, now Pat. No. 8,044,174, which is a continuation of application No. 09/422,838, filed on Oct. 22, 1999, now Pat. No. 6,835,809.

(60) Provisional application No. 60/105,348, filed on Oct. 23, 1998.

(51) Int. Cl.
*A61K 38/16* (2006.01)
*C07K 14/00* (2006.01)

(52) U.S. Cl.
USPC ........... 530/324; 530/326; 530/327; 514/21.3

(58) Field of Classification Search
USPC ......................................... 530/324, 326, 327
See application file for complete search history.

(56) References Cited

U.S. PATENT DOCUMENTS

| | | | |
|---|---|---|---|
| 3,691,016 A | 9/1972 | Patel |
| 3,941,763 A | 3/1976 | Sarantakis |
| 3,969,287 A | 7/1976 | Jaworek |
| 4,002,531 A | 1/1977 | Royer |
| 4,179,337 A | 12/1979 | Davis et al. |
| 4,195,128 A | 3/1980 | Hildebrand |
| 4,229,537 A | 10/1980 | Hodgins |
| 4,247,642 A | 1/1981 | Hirohara et al. |
| 4,289,872 A | 9/1981 | Denkewalter |
| 4,301,144 A | 11/1981 | Iwashita et al. |
| 4,330,440 A | 5/1982 | Ayers |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 4,904,584 A | 2/1990 | Shaw |
| 4,925,673 A | 5/1990 | Steiner |
| 5,013,556 A | 5/1991 | Woodle |
| 5,089,261 A | 2/1992 | Nitecki et al. |
| 5,098,833 A | 3/1992 | Lasky et al. |
| 5,116,964 A | 5/1992 | Capon et al. |
| 5,216,131 A | 6/1993 | Lasky et al. |
| 5,223,409 A | 6/1993 | Ladner et al. |
| 5,225,538 A | 7/1993 | Capon et al. |
| 5,229,490 A | 7/1993 | Tam |
| 5,252,714 A | 10/1993 | Harris et al. |
| 5,281,698 A | 1/1994 | Nitecki |
| 5,284,656 A | 2/1994 | Platz |
| 5,336,603 A | 8/1994 | Capon et al. |
| 5,338,665 A | 8/1994 | Schatz et al. |
| 5,362,852 A | 11/1994 | Geoghegan |
| 5,376,367 A | 12/1994 | Williams et al. |
| 5,428,130 A | 6/1995 | Capon |
| 5,432,018 A | 7/1995 | Dower et al. |
| 5,455,165 A | 10/1995 | Capon et al. |
| 5,480,981 A | 1/1996 | Goodwin |
| 5,498,530 A | 3/1996 | Schatz et al. |
| 5,514,582 A | 5/1996 | Capon et al. |
| 5,565,335 A | 10/1996 | Capon et al. |
| 5,608,035 A | 3/1997 | Yanofsky et al. |
| 5,714,147 A | 2/1998 | Capon et al. |
| 5,726,290 A | 3/1998 | Bpdary et al. |
| 5,733,731 A | 3/1998 | Schatz et al. |
| 5,739,277 A | 4/1998 | Presta |
| 5,767,234 A | 6/1998 | Yanofsky et al. |
| 5,773,569 A | 6/1998 | Wrighton et al. |
| 5,786,331 A | 7/1998 | Barrett et al. |
| 5,792,451 A | 8/1998 | Sarubbi |
| 5,808,029 A | 9/1998 | Brockhaus et al. |
| 5,824,784 A | 10/1998 | Kinstler et al. |
| 5,834,594 A | 11/1998 | Hakimi et al. |
| 5,840,844 A | 11/1998 | Lasky et al. |
| 5,869,451 A | 2/1999 | Dower |

(Continued)

FOREIGN PATENT DOCUMENTS

| CA | 2436671 A1 | 6/2002 |
|---|---|---|
| EP | 0 124 961 | 11/1984 |

(Continued)

OTHER PUBLICATIONS

Abuchowski et al., "Effect of Covalent Attachment of Polyethylene Glycol on Immunogenicity and Circulating Life of Bovine Liver Catalase," J. Biol. Chem, 252(11):3582-3586 (1977).
Abuchowski et al., Cancer Biochem, Biophys., 7:175-186 (1984).
Adey et al. (1996), 'Identification of calmodulin-binding peptide consensus sequences from a phage-displayed random peptide library', Gene 169:133-134.
Adey et al. (1997), 'Isolation of peptides from phage-displayed random peptide libraries that interact with the talin-binding domain of vinculin', Biochem. J. 324:523-528.
Ahern et al, (1990), 'Special Report: The Peptide-Oligonucleotide Partnership', The Scientist 4 (19):24-25.
Akers et al., "Peptides and Proteins as Parenteral Solutions, Pharmaceutical Formulation Development of Peptides and Proteins," Sven Frokjaer, Lars Hovgaard, eds, Pharmaceutical Science, Taylor and Francis, UK, 8:145-177 (1999).
Akeson et al. (1996), 'AF12198, a Novel Low Molecular Weight Antagonist, Selectively Binds the Human Type I Interleukin (IL)-1 Receptor and Blocks in vivo Responses to IL-1', J. Biol. Chem. 271:30517-30523.

(Continued)

Primary Examiner — Michael Borin
(74) Attorney, Agent, or Firm — Robert T. Ramos

(57) ABSTRACT

The invention relates to the field of compounds, especially peptides or polypeptides, that have thrombopoietic activity. The peptides and polypeptides of the invention may be used to increase platelets or platelet precursors (e.g., megakaryocytes) in a mammal.

28 Claims, 7 Drawing Sheets

(56) References Cited

U.S. PATENT DOCUMENTS

| | | | |
|---|---|---|---|
| 5,869,452 A | 2/1999 | Ng et al. | |
| 5,877,151 A | 3/1999 | Pereira | |
| 5,880,096 A | 3/1999 | Barrett et al. | |
| 5,880,103 A | 3/1999 | Urban et al. | |
| 5,886,150 A | 3/1999 | Duchesne et al. | |
| 5,888,763 A | 3/1999 | Hanafusa et al. | |
| 5,922,545 A | 7/1999 | Mattheakis et al. | |
| 5,932,546 A | 8/1999 | Barrett | |
| 5,932,946 A | 8/1999 | Miyasaka et al. | |
| 5,945,507 A | 8/1999 | Montelaro et al. | |
| 5,985,265 A | 11/1999 | Kinstler et al. | |
| 5,985,599 A | 11/1999 | McKenzie et al. | |
| 6,117,655 A | 9/2000 | Capon et al. | |
| 6,251,864 B1 | 6/2001 | Dower | |
| 6,423,685 B1 | 7/2002 | Drummond et al. | |
| 6,433,135 B1 | 8/2002 | El-Taylor et al. | |
| 6,586,398 B1 | 7/2003 | Kinstler et al. | |
| 6,635,646 B1 | 10/2003 | Laughlin | |
| 6,660,843 B1 | 12/2003 | Feige et al. | |
| 6,835,809 B1 * | 12/2004 | Liu et al. | 530/324 |
| 6,919,426 B2 | 7/2005 | Boone et al. | |
| 7,189,827 B2 * | 3/2007 | Feige | 530/391.7 |
| 7,332,474 B2 * | 2/2008 | Min et al. | 530/317 |
| 7,442,778 B2 | 10/2008 | Gegg et al. | |
| 7,488,590 B2 | 2/2009 | Feige et al. | |
| 2008/0070840 A1 | 3/2008 | Min et al. | |
| 2008/0254020 A1 | 10/2008 | Walker et al. | |
| 2009/0011497 A1 | 1/2009 | Min et al. | |
| 2009/0053242 A1 | 2/2009 | Nichol et al. | |
| 2009/0258017 A1 | 10/2009 | Callahan et al. | |

FOREIGN PATENT DOCUMENTS

| | | |
|---|---|---|
| EP | 0 154 316 | 9/1985 |
| EP | 01 73 494 | 3/1986 |
| EP | 0 315 456 | 5/1989 |
| EP | 0 325 224 | 7/1989 |
| EP | 0 335 423 | 10/1989 |
| EP | 0 401 384 | 12/1990 |
| EP | 0 442 724 | 8/1991 |
| EP | 0 539 167 | 8/1991 |
| EP | 0 473 268 | 3/1992 |
| EP | 0 526 452 B1 | 2/1993 |
| EP | 0 585 287 | 3/1994 |
| EP | 0 770 624 | 5/1997 |
| EP | 0 911 393 | 4/1999 |
| EP | 0 714 912 | 5/1999 |
| EP | 0958829 A1 | 11/1999 |
| EP | 1 029 870 | 8/2000 |
| WO | WO90-04606 | 5/1990 |
| WO | WO90-07938 | 7/1990 |
| WO | WO92/16221 | 10/1992 |
| WO | WO 93/08207 | 4/1993 |
| WO | WO 93/21259 | 10/1993 |
| WO | WO94/07921 | 4/1994 |
| WO | WO94/13322 | 6/1994 |
| WO | WO95/09917 | 4/1995 |
| WO | WO95/14714 | 6/1995 |
| WO | WO 95/18858 | 7/1995 |
| WO | WO 95/21919 | 8/1995 |
| WO | WO 95/21920 | 8/1995 |
| WO | WO 95/26746 | 10/1995 |
| WO | WO96/05309 | 2/1996 |
| WO | WO96/11214 | 4/1996 |
| WO | WO96/11953 | 4/1996 |
| WO | WO96/17942 | 6/1996 |
| WO | WO96/18412 | 6/1996 |
| WO | WO96/23899 | 8/1996 |
| WO | WO96/30057 | 10/1996 |
| WO | WO96/32478 | 10/1996 |
| WO | WO 96/32478 | 10/1996 |
| WO | WO 96/40189 A1 | 12/1996 |
| WO | WO 96/40750 | 12/1996 |
| WO | WO96/40772 | 12/1996 |
| WO | WO96/40987 | 12/1996 |
| WO | WO97/00270 | 1/1997 |
| WO | WO97/04801 A1 | 2/1997 |
| WO | WO97/08203 | 3/1997 |
| WO | WO97/08553 | 3/1997 |
| WO | WO97/41220 | 4/1997 |
| WO | WO97/23183 | 7/1997 |
| WO | WO97/23614 | 7/1997 |
| WO | WO97/28828 | 8/1997 |
| WO | WO97/31019 | 8/1997 |
| WO | WO 97/34631 | 9/1997 |
| WO | WO97/35969 | 10/1997 |
| WO | WO97/40070 | 10/1997 |
| WO | WO97/44453 | 11/1997 |
| WO | WO98/09985 | 3/1998 |
| WO | WO98/10795 | 3/1998 |
| WO | WO98/15833 | 4/1998 |
| WO | WO98/24477 | 6/1998 |
| WO | WO 98/25965 A2 | 6/1998 |
| WO | WO98/28427 | 7/1998 |
| WO | WO98/31820 | 7/1998 |
| WO | WO98/33812 | 8/1998 |
| WO | WO98/46257 | 10/1998 |
| WO | WO98/46751 | 10/1998 |
| WO | WO98/53842 | 12/1998 |
| WO | WO98/55620 | 12/1998 |
| WO | WO99/05302 | 2/1999 |
| WO | WO99/10494 | 3/1999 |
| WO | WO99/14244 | 3/1999 |
| WO | WO99/17789 | 4/1999 |
| WO | WO99/18243 | 4/1999 |
| WO | WO99/18781 | 4/1999 |
| WO | WO99/24462 | 5/1999 |
| WO | WO99/38526 | 8/1999 |
| WO | WO99-42592 | 8/1999 |
| WO | WO99/45944 | 9/1999 |
| WO | WO99/47151 | 9/1999 |
| WO | WO99/50282 | 10/1999 |
| WO | WO99/51254 | 10/1999 |
| WO | WO99/60013 | 11/1999 |
| WO | WO99/61476 | 12/1999 |
| WO | WO99/62539 | 12/1999 |
| WO | WO00/01402 | 1/2000 |
| WO | WO00/04048 | 1/2000 |
| WO | WO00/09560 | 2/2000 |
| WO | WO00/11028 | 3/2000 |
| WO | WO00/24770 | 5/2000 |
| WO | WO00/24782 | 5/2000 |
| WO | WO00/47740 | 8/2000 |
| WO | WO01/02440 | 1/2001 |
| WO | WO01/83525 A2 | 11/2001 |
| WO | WO02/46238 | 6/2002 |
| WO | WO02/078612 | 10/2002 |
| WO | WO03/031589 | 4/2003 |
| WO | WO 03/057134 | 7/2003 |
| WO | WO2004/002417 | 1/2004 |
| WO | WO2004/002424 | 1/2004 |
| WO | WO2004/026329 | 4/2004 |
| WO | WO2004/039337 | 5/2004 |
| WO | WO2004/050017 | 6/2004 |
| WO | WO2004/058988 | 7/2004 |
| WO | WO2004/092215 A2 | 10/2004 |
| WO | WO2005/023834 | 3/2005 |
| WO | WO2006/010057 | 1/2006 |
| WO | WO2006/094813 | 9/2006 |
| WO | WO 2007/022070 A2 | 2/2007 |

OTHER PUBLICATIONS

Alberts et al., "Synthesis of a Novel Hematopoietic Peptide, SK&F 107647," Thirteenth Am. Pep. Symp., 367-369 (1993).

Aledort, et al., Am. J. Hematol. 76:205-213, 2004.

Alexander et al., Blood, 87: 2162-2170 1996.

Ashkenazi, Avi and Chamow, Steven M., entitled Immunoadhesins as research tools and therapeutic agents, Current Opinion in Immunology, 195-200 (1995).

Ball et al. (1997), 'Cell-cycle arrest and inhibition of Cdk4 activity by small peptides based on the carboxy-terminal domain of p21WAF1', Current Biology 7:71-80.

Barna et al., Cancer Immunol. Immunother., 38:38-42 (1994).

(56) References Cited

OTHER PUBLICATIONS

Beauchamp et al, "A New Procedure for the Synthesis of Polyethylene Glycol-Protein Adducts ; Effects on Function, Receptor Recognition, and Clearance of Superoxide Dismutase, Lactoferrin, and α2-Macroglobulin," Anal. Biochem., 131:25-33 (1983).
Becker et al. (1989), "Expression of a Hybrid Immunoglobulin-T cell Receptor Protein in Transgenic Mice," Cell 58: 911-921.
Bernard et al. (1980), "Nucleotide sequence of immunoglobulin heavy chain joining segments between translocated Vh and μ constant region genes," Proc. Natl. Acad. Sci. USA 77(6): 3630-3634.
Bhatnagar et al. (1996), 'Structure-Activity Relationships of Novel Hematoregulatory Peptides', J. Med. Chem. 39:3814-3819.
Blondelle, Sylvie E. and Houghten, Richard A. entitled Novel antimicrobial compounds identified using synthetic combinatorial library technology, TIBTECH Feb. 1996 (vol. 14) Copyright 1996, Elsevier Science Ltd., pp. 60-65.
Böttger et al. (1996), 'Identification of novel mdm2 binding peptides by phage display', Oncogene 13:2141-2147.
Böttger et al. (1997), 'Molecular Characterization of the hdm2-p53 Interaction', J. Mol. Biol. 269:744-756.
Boulianne et al. (1984), "Production of functional chimaeric Mousem/human antibody," Nature 312: 643-646.
Brocks et al. (1997), "A TNF receptor antagonistic scFv, which is not secreted in mammalian cells, is expressed as a soluble mono- and bivalent scFv derivative in insect cells," Immunotechnology 3(3):173-184.
Broudy, et al., Blood, 85:1719-1726 (1995).
Burstein et al. (1988), 'Thymic Humoral Factor γ2: Purification and Amino Acid Sequence of an Immunoregulatory Peptide from Calf Thymus', Biochemistry 27:4066-4071.
Busseel et al., Abstract #220, Blood, 106:68a (2005).
Bussel, et al. Title: AMG 531, a Thrombopoiesis-Stimulating Protein, for Chronic ITP; The New England Journal of Medicine—2006;355: pp. 1672-1681.
Cacace et al., "The Hofmeister Series: Salt and Solvent Effects on Interfacial Phenomena," Quarterly Reviews of Biophysics, 30(3) : 241-277 (1997).
Carosella et al. (1990), "Anti-Human Interleukin 2 Receptor Monoclonal Antibody Isotypic Switching: Chimeric Rat-Human Antibodies," Human Immunology 29:233-246.
Carpenter et al., "Interactions of Stabilizing Additives with Proteins During Freeze-Thawing and Freeze-Drying," Develop. Biol. Standard, 74:225-239 (1991).
Chamow et al. (1996), "Immunoadhesins: principles and applications," Tibtech. 14:52-60.
Chan et al., Cell, 93:681-684 (1998).
Chang et al., "Development of a Stable Freeze-dried Formulation of Recombinant Human Interleukin-1 Receptor Antagonist," Pharm Res., 13(2):243-249 (1996).
Chang et al., "Surface-Induced Denaturation of Proteins during Freezing and Its Inhibition by Surfactants," J., Pharm. Sci., 85(12):1325-1330 (1996).
Chen et al., "Influence of Calcium Ions on the Structure and Stability of Recombinant Human Deoxyribonuclease I in the Aqueous and Lyophilized States," J. Pharm Sci., 88(4) : 477-482 (1999).
Chen et al., "Influence of Histidine on the Stability and Physical Properties of a Fully Human Antibody in Aqueous and Solid Forms," Pharm Res., 20(12) : 1952-1960 (2003).
Chen, Tracy, "Formulation Concerns of Protein Drugs," Drug Development and Industrial Pharmacy, 18:1311-1354 (1992).
Chevalier F. et al., "Maillard Glycation of β-lactoglobulin Induces Conformation Changes," Nahrung/Food, 46(2): 58-63 (2002).
Chirinos-Rojas et al. (1998), 'A Peptidomimetic Antagonist of TNF-α-Mediated Cytotoxicity Identified from a Phage-Displayed Random Peptide Library', Journal of Immunology 161:5621-5626.
Conforti et al., "PEG Superoxide Dismutase Derivatives: Anti-Inflammatory Activity in Carrageenan Pelurisy in Rats," Pharm. Research Commun., vol. 19(4):287-294 (1987).

Cooper et al. (1987), 'Purification and characterization of a peptide from amyloid-rich pancreases of type 2 diabetic patients', PNAS 84:8628-8632.
Cortese et al. (1996), 'Selection of biologically active peptides by phage display of random peptide libraries', Current Opinion in Biotechnology 7:616-621.
Couet et al. (1997), 'Identification of Peptide and Protein Ligands for the Caveolin-scaffolding Domain', The Journal of Biological Chemistry 272 (10):6525-6533.
Couet et al. (1997), 'Interaction of a Receptor Tyrosine Kinase, EGF-R, with Caveolins', The Journal of Biological Chemistry vol. 272 (48):30429-30438.
Cuthbertson et al. (1997), 'Design of Low Molecular Weight Hematoregulatory Agents from the Structure-Activity Relationship of a Dimeric Pentapeptide', J. Med. Chem 40:2876-2882.
Dedman et al. (1993), 'Selection of Targeted Biological Modifiers from a Bacteriophage Library of Random Peptides', The Journal of Biological Chemistry 268 (31):23025-23030.
Delgado et al., "Coupling of PEG to Protein By Activation With Tresyl Chloride, Applications In Immunoaffinity Cell Partitioning," Fisher et al., eds., Separations Using Aqueous Phase Systems, Applications In Cell Biology and Biotechnology, Plenum Press, N.Y. N.Y., 211-213 (1989).
Derrick et al., "Effect of Metal Cations on the Conformation and Inactivation of Recombinant Human Factor VIII," J. Pharm. Sci., 93(10) : 2549-2557 (2004).
Douglas et al., Am. J. Clin. Pathol., 117:844-850 (2002).
Dyson et al. (1995), 'Selection of peptide inhibitors of interactions involved in complex protein assemblies: Association of the core and surface antigens of hepatitis B virus', Proc. Natl. Acad. Sci. USA 92:2194-2198.
Fahraeus et al. (1996), 'Inhibition of pRb phosphorylation and cell-cycle progression by a 20-residue peptide derived from p16CDKN2/INK4A', Current Biology 6:84-91.
Fairbrother et al. (1998), 'Novel Peptides Selected to Bind Vascular Endothelial Growth Factor Target the Receptor-Binding Site', Biochemistry 37:17754-17764.
Fatouros et al., "Recombinant Factor VIII SQ-Influence of Oxygen, Metal Ions, pH and Ionic Strength on its Aqueous Solution," Int. J. Pharm., 155:121-131 (1997).
Fields et al., "A Spectrophotometric Method for the Microdetermination of Periodate," Biochem J., 108:883-887 (1968).
Francis et al., "PEG-Modified Proteins," Stability of protein pharmaceuticals: Part B in vivo pathways of degradation and strategies for protein stabilization, Eds. Ahern., T. Manning, M.C., Plenum, N.Y., pp. 235-263 (1992).
Francis, Gillian E., "Protein Modification and Fusion Proteins," Focus on Growth Factors,Guest Review: Royal Free Hospital School of Medicine, London, UK,3:4-10, (1992).
Fransson J.R., "Oxidation of Human Insulin-Like Growth Factor I in Formulation Studies, 3. Factorial Experiments of the Effects of Ferric Ions, EDTA, and Visible Light on Methionine Oxidation and Covalent Aggregation in Aqueous Solution," J. Pharm. Sci., 86(9):1046-1050 (1997).
Frederickson, et al. Title: A rationally designed agonist antibody fragment that functionally mimics thrombopoietin; Sep. 26, 2006; Applied Biological Sciences—vol. 103, No. 39, pp. 14307-14312.
Fukumoto et al. (1998), 'Peptide mimics of the CTLA4-binding domain stimulate T-cell proliferation', Nature Biotechnology, 16:267-270.
Gaertner et al., "Chemo-enzymic Backbone Engineering of Proteins," J. Biol. Chem., 269(10):7224-7230 (1994).
Gaertner et al., "Construction of Protein Analogues by Site-Specific Condensation of Unprotected Fragments," Bioconjugate Chem., 3:262-268 (1992).
Gan et al. (1988), 'Echistatin', JBC 263:19827-19832.
Garber et al. (2001), "A new synthetic class A amphipathic peptide analogue protects mice from diet-induced atherosclerosis," J. Lipid Research 42: 545-552.
Gascoigne et al. (1987), "Secretion of a chimeric T-cell receptor-immunoglobulin protein," Proc. Natl. Acad. Sci. USA 84: 2936-2940.

(56) References Cited

OTHER PUBLICATIONS

Geoghegan et al., "Site-Directed Conjugation of Nonpeptide Groups to Peptides and Proteins via Periodate Oxidation of a 2-Amino Alcohol. Application to Modification at N-Terminal Serine," Bioconjugate Chem., 3:138-146 (1992).
Ghetie et al. (1997), 'Increasing the serum persistence of an IgG fragment by random mutagenesis', Nature Biotechnology 15:637-640.
Gibbs et al. (1994), 'Farnesyltransferase Inhibitors: Ras Research Yields a Potential Cancer Therapeutic', Cell 77:175-178.
Gibbs et al. (1994), 'Pharmaceutical Research in Molecular Oncology', Cell 79:193-198.
Goodson et al. (1994), 'High-affinity urokinase receptor antagonists identified with bacteriophase peptide display', Proc. Natl. Acad. Sci. USA 91:7129-7133.
Graf et al., Peptides, 7:1165-1187 (1986).
Greenwald et al., "Poly(ethylene glycol) Conjugated Drugs and Prodrugs: A Comprehensive Review," Crit Rev Therap Drug Carrier Syst, 17(2):101-161 (2000).
Harris et al., "Pegylation, A Novel Process for Modifying Pharmacokinetics," Clin Pharmacokinet, 40(7): 539-551 (2001).
Harwig et al., Methods Enz., 236:160-172 (1994).
Herz et al. (1997), Molecular Approaches to Receptors as Targets for Drug Discovery, J. of Receptor & Signal Transduction Research 17(5):671-776.
Hollander-Rodriguez et al., "Hyperkalemia," Am. Fam. Physician., 73(2): 283-290 (2006).
Hong et al. (1995), 'Protein ligands of the human adenovirus type 2 outer capsid identified by biopanning of a phage-displayed peptide library on separate domains of wild-type and mutant penton capsomers', The EMBO Journal 14:4714-4727.
Hughes, David (1998), 'Therapeutic antibodies make a comeback', Drug Discovery Today 3(10):439-442.
Hurneny A. et al., "Qualitative Determination of Specific Protein Glycation Products by Matrix-Assisted Laser Desorption/Ionization Mass Spectrometry Peptide Mapping," J. Agric Food Chem., 50: 2153-2160 (2002).
Inagaki-Ohara et al. (1996), 'Effects of a Nonapeptide Thymic Hormone on Intestinal Intraepithelial Lymphocytes in Mice Following Administration of 5-Fluorouracill', Cellular Immunology 17:30-40.
Inglot, Anna D. (1997), 'Classification of Cytokines According to the Receptor Code', Archivum Immunologies et Therapine Experimentalis 45:353-357.
Ishikawa et al (1998), 'GD1α-replica peptides functionally mimic GD1α, an adhesion molecule of metastatic tumor cells, and suppress the tumor metastasis', FEBS 441:20-24.
Jefferies, D. (1998), 'Selection of Novel Ligands from Phage Display Libraries: An Alternative Approach to Drug and Vaccine Discovery?', Parasitology Today 14(5):202-206.
Jones et al. (1998), 'Stromal Expression of Jagged I Promotes Colony Formation by Fetal Hematopoietic Progenitor Cells', Blood 92(5):1505-1511.
Junghans, R.P. (1997), Finally! The Brambell Receptor (FcRB), Immunologic Research 16(1):29-57.
Kappelgaard et al., "Liquid Growth Hormone: Preservatives and Buffers," Horm Res., 62(Suppl 3):98-103 (2004).
Katre et al., "Chemical Modification of Recombinant Interleukin 2 by Polyethylene Glycol Increases its Potency in the Murine Meth A Sarcoma Model," Proc. Natl. Acad. Sci. U.S.A., vol. 84: 1487-1491 (1987).
Kaushansky, L., Hematopoietic Growth Factor Mimetics, Annuals of the New York Academy of Sciences, Jun. 2001, pp. 131-138, vol. 938, New York Acadmey of Sciences, New York, NY, US.
Kaushansky, M.D. Title: Thrombopoietin; Sep. 10, 1998; The New England Journal of Medicine; pp. 746-754.
Kautz et al., "The Hydrolsis of Sucrose by Hydrochloric Acid in the Presence of Alkali and Alkaline earth Chlorides," JACS, 50(4), 1022-1030 (1928).
Kay et al., Gene, 128 (1993), 59-65.

Kemp et al. (1981), "Direct Immunoassay for detecting *Escherichia coli* colonies that contain polypeptides encoded by cloned DNA segments," Proc. Natl. Acad. Sci. USA 78(7):4520-4524.
Kimura et al., Journal of Biochemistry, Molecular Biology & Biophysics, 2:281-286 (1999).
King et al. (1991), 'Modulation of Bone Marrow Stromal Cell Production of Colony Stimulating Activity by the Synthetic Peptide', Exp. Hematol. 19:481.
King et al. (1995), 'Hematoregulatory Peptide, SK&F Induced Stromal Cell Production of KC Enhances CFU-GM Growth and Effector Cell Function', Blood 86(1):309a.
Kitamura et al. (1993), 'Adrenomedullin: A Novel Hypotensive Peptide Isolated from Human Pheochromocytoma', BBRC 192:553-560.
Kluczyk et al. (1997), 'Immunomodulatory Activity of Oligopeptides Related to Interleukin 1 Receptor Antagonist Sequence', Archivum Immunologiac et Therapiae Experimentalis 45:427-433.
Knapp et al. (1989), "Towards a better definition of human leucocyte surface molecules," Immunology Today 10(8):253-258.
Koivunen et al. (1999), 'Tumor targeting with a selective gelatinase inhibitor', Nature Biotech. 17:768-774.
Kopeček et al., "Water Soluble Polymers in Tumor Targeted Delivery," J. Controlled Release, 74:147-158 (2001).
Kraft et al. (1999), 'Definition of an Unexpected Ligand Recognition Motif for αvβ6 Integrin', Journal of Biological Chemistry 274(4):1979-1985.
Kreeger, Karen Y., "Immunological Applications Top List of Peptide-Synthesis Services," The Scientist, 10(13): 18-20 (1996).
Kuter et al., Blood, 100:3457-3469 (2002).
Kuter, et al. Title: Efficacy of romiplostim in patients with chronic immune thrombocytopenic purpura: a double-blind randomized controlled trial; Feb. 2, 2008; The Lancet—vol. 371, pp. 39.
Laerum et al. (1988), 'The Dimer of Hemoregulatory Peptide (HP5B) Stimulates Mouse and Human Myelopoiesis in vitro', Exp. Hemat. 16:274-280.
Lam et al., "Antioxidants for Prevention of Methionine Oxidation in Recombinant Monoclonal Antibody HER2," J. Pharm Sci., 86(11):1250-1255 (1997).
Laursen et al., "Pain Perception after Subcutaneous Injections of Media Containing Different Buffers," Basic Clin Pharmacol Toxicol, 98: 218-21 (2006).
Lee et al., "Thermal Stability of Proteins in the Presence of Poly(ethylene glycols)," Biochemistry, 26: 7813-7819 (1987).
Lehninger, Albert L., "The Molecular Basis of Cell Structure and Function," Biochemistry, 2nd Edition, Worth Publishers, Inc., New York, 71-77 (1975).
Liao, et al., Influence of the Active Pharmaceutical Ingredient Concentration on the Physical State of Mannitol-Implications in Freeze-Drying, Pharmaceutical Research, Nov. 2005, pp. 1978-1985, vol. 22, No. 11.
Linse et al. (1997), 'A Region of Vitamin K-dependent Protein S That Binds to C4b Binding Protein (C4BP) Identified Using Bacteriophage Peptide Display Libraries', The Journal of Biological Chemistry 272(23):14658-14665.
Linsley et al. (1991), 'CTLA-4 is a Second Receptor for the B Cell Activation Antigen B7', J. Exp. Med. 174:561-569.
Liu et al., "Reversible Self-Association Increases the Viscosity of a Concentrated Monoclonal Antibody in Aqueous Solution," J. Pharm Sci., 94(9) : 1928-1940 (2005).
Liu et al., "Reversible Self-Association Increases the Viscosity of a Concentrated Monoclonal Antibody in Aqueous Solution," J. Pharm Sci., 95(1) : 234-235 (2006).
Loetscher et al. (1993), "Efficacy of a chimeric TNFR-IgG fusion protein to inhibit TNF activity in animal models of septic shock," Elsevier Science Publishers pp. 455-462.
Love et al. (1989), "Recombinant Antibodies Possessing Novel Effector Functions," Methods in Enzymology 178:515-527.
Lowman, H.B., "Bacteriophage Display and Discovery of Peptide Leads for Drug Development," Ann. Rev. Biophys. Biomol. Struct., 26: 401-424 (1997).
Lundergan et al., J. Periodontal Res., 34:223-228 (1999).

(56) References Cited

OTHER PUBLICATIONS

MacKenzie et al., "Non-Equilibrium Freezing Behaviour of Aqueous Systems [and Discussion]," Phil Trans R Soc London, Ser B, Biol, 278:167-189 (1977).
Mariuzza et al. (1989), "Secretion of a Homodimeric VaCK t-cell Receptor-Immunoglobulin Chimeric Protein," J. Biological Chemistry 24(13):7310-7316.
Martens et al. (1995), 'Peptides which bind to E-selectin and block neutrophil adhesion', The Journal of Biological Chemistry 270(36):21129-21136.
Maurer et al. (1997), 'Autodisplay: One-Component System for Efficient Surface Display and Release of Soluble Recombinant Proteins from *Escherichia coli*', ournal of Bacteriology 179(3):794-80.
McGregor, Duncan (1996), 'Selection of proteins and peptides from libraries displayed on filamentous bacteriophage', Molecular Biotechnology 6:155-162.
Miller et al., Cancer 47:207-214 (1981).
Minogue et al., "Bacteriostatic Saline Containing Benzyl Alcohol Decreases the Pain Associated with the Injection of Propofol," Anesth Analg., 100:683-686 (2005).
Moodie et al. (1994), 'The 3Rs of Llife: Ras, Raf and Growth Regulation', TIG 10(2):44-48.
Moonga et al., Exp. Physiol, 83:717-725 (1998).
Morikis et al. (1998), 'Solution structure of Compstatin, a potent complement inhibitor', Protein Science 7:619-627.
Morrison (1985), "Transfectomas Provide Novel Chimeric Antibodies," Science 229:1202-1207.
Morrison et al, (1984), "Chimeric human antibody molecules: Mouse anigen-binding domains with human constant region domains," Proc. Natl. Acad. Sci. USA 81:6851-6855.
Munro (1984), "Uses of chimaeric antibodies," Nature 312:597-.
Naranda et al. (Jun. 1999), "Activation of erythropoietin receptor in the absence of hormone by a peptide that binds to a domain different from the hormone binding site," Proc. Natl. Acad. Sci. USA 96:7569-7574.
Nathan et al., "Copolymers of Lysine and Polyethylene Glycol: A New Family of Functionalized Drug Carriers," Bioconj Chem., 4:54-62 (1993).
Nathan et al., "Hydrogels Based on Water-Soluble Poly(ether urethanes) Derived from L-Lysine and Poly(ethylene glycol)," Macromolecules, 25:4476-4484 (1992).
Neuberger et al. (1984), "Recombinant antibodies possessing novel effector functions," Nature 312:604-608.
Nishi et al. (1996), 'Tight-binding inhibitory sequences against pp60c-src identified using a random 15-amino-acid peptide library', FEBS 399:237-240.
Oeswein, et al., "Aerosolization of Protein Pharmaceuticals", Proc. Symp. Resp., Drug Delivery II, Keystone, Colorado, pp. 14, 16-48 (Mar. 1990).
Park et al., Nat. Biotechnol., 18:194-198 (2000).
Pasquaimi et al. (1996), 'Organ targeting in vivo using phage display peptide libraries', Nature 380:364-366.
Paukovits et al. (1984), 'Structural Investigations on a Peptide Regulating Hemopoiesis in vitro and vivo'. Hoppe-Seylers Z Physiol. Chem 364:303-311.
Pawson et al. (1993), 'SH2 and SH3 Domains', Current Biology 3(7):434-442.
Picksley et al., Oncogene, 9:2523-2529 (1994).
Pierce et al. (1995), 'Identification of cyclized calmodulin antagonists from a phage display random peptide library', Molecular Diversity 1:259-265.
Piette et al. (1997), Mdm2: keeping p53 under control, Oncogene 15:1001-1010.
Powell et al., "Compendium of Excipients for Parenteral Formulations," PDA J. Pharm. Sci. Technology, 52:238-311 (1998).
Powis, Garth (1991), Signalling targets for anticancer drug development, TIPS 12:188-194.
Randolph et al., "Surfactant-Protein Interactions," Pharm Biotechnol., 13:159-175 (2002).

Remmele et al., "Interleukin-1 Receptor(IL-1R) Liquid Formulation Development Using Differential Scanning Calorimetry," Pharm. Res., 15(2) : 200-208 (1998).
Remmele et al., "Minimization of Recombinant Human Flt3 Ligand Aggregation at the Tm Plateau: A Matter of Thermal Reversibility," Biochemistry, 38:5241-5247 (1999).
Rickles et al. (1994), 'Identification of Src, Fyn, Lyn, PI3K and Abl SH3 domain ligands using phage display libraries', The EMBO Journal 13(23):5598-5604.
Roberts et al., "RNA-Peptide Fusions for the in vitro Selection of Peptides and Proteins," Proc. Natl. Acad. Sci. USA, 94:12297-12302 (1997).
Rodriguez-Viciana et al. (1994), 'Phosphatidylinositol-3-OH kinase as a direct target of Ras', Nature 370:527-532.
Roy et al., "Effects of Benzyl Alcohol on Aggregation of recombinant Human Interleukin-1-Receptor Antagonist in Reconstituted Lyophilized Formulations," J. Pharm Sci., 94(2) : 382-396 (2005).
Rudikoff, et al., Proc. Natl. Acad. Sci., 1982, 79, 1979-1983.
Rudolf et al,. The Journal of Immunology, 1998, 160, 3315-21.
Russel et al, Introduction to phage biology and phage display, In A Practical Approach; Oxford University Press; 2004; 1-26.
Sahu et al. (1996), 'Inhibition of Human Complement by a C3-Binding Peptide Isolated from a Phage-Displayed Random Peptide Library I', The Journal of Immunology 157:884-891.
Sharon et al. (1984), "Expression of a VHCK chimaeric protein in mouse myeloma cells," Nature 309:364-367.
Siemion et al. (1991), 'The Evidence on the Possible Interleukin-1α Tuftsin Competition', Archivum Immunologiae et Therapiae Experimentalis 39:605-611.
Smith et al., "Isolation of Glucagon Antagonists by Random Molecular Mutagenesis and Screening," Mol. Pharmacol. 43: 741-748 (1993).
Sparks et al. (1994), 'Identification and Characterization of Src SH3 Ligands from Phage-displayed Random Peptide Libraries', The Journal of Biological Chemistry 269(39):23853-23856.
Sparks et al. (1996), 'Distinct ligand preferences of Src homology 3 domains from Src, Yes, Abl, Cortactin, p53bp2, PLCγ, Crk, and Grb2', Proc. Natl. Acad. Sci. USA 93:1540-1544.
Stauffer et al. (1997), 'Inhibition of Lyn Function in Mast Cell Activation by SH3 Domain Binding Peptides', Biochemistry 36:9388-9394.
Stepan et al., Abstract #1240, Blood, 87:567-573 (1996).
Stoffel et al., Blood, 87:567-573 (1996).
Stryer et al., in Biochemistry, Third edition, W.H. Freeman Company, New York, pp. 31-33, 1998.
Suzuki et al., "Physiochemical and Biological Properties of Poly(ethylene Glycol)-Coupled Immunoglobulin G," Biochem. Biophys. Acta, vol. 788:248-255 (1984).
Suzuki et al., Comp. Biochem, Physiol., 102B:679-690 (1992).
Tai et al. (1990), "A Bifunctional Fusion Protein Containing Fc-Binding Fragment B of Staphylococcal Protein A Amino Terminal to Antidigoxin Single-Chain Fv," Biochemistry 29:8024-8030.
Takasaki et al., "Structure-based Design and Characterization of Exocyclic Peptidomimetics that Inhibit TNFαBinding to its Receptor," Nature Biotech., 15:1266-1270 (1997).
Tang et al., "Design of Freeze-Drying Processes for Pharmaceuticlas:Practical Advice," Pharm Res., 21(2):191-200 (2004).
Tomita et al., "Sensitized Photooxidation of Histidine and Its Derivatives. Products and Mechanism of the Reaction," Biochemistry, 8(12) 5149-5160 (1969).
Traunecker et al. (1986), "A novel approach for preparing anti-T cell receptor constant region antibodies," Eur. J. Immunol. 16: 851-853.
Traunecker et al. (1988), "Soluble CD4 molecules neutralize human immunodeficiency virus type I," Nature 331:84-86.
Traunecker et al. (1989), "Highly efficient neutralization of HIV with recombinant CD4-immunoglobulin molecules," Nature 339: 68-70.
Ulich et al., Blood, 86:971-976 (1995).
Uto, I., et al. "Determination of Urinary Tamm-Horsfall Protein by ELISA using a Maleimide Method for Enzyme-Antibody Conjugation," J. Immunol. Methods 138, 87-94 (1991).

(56) References Cited

OTHER PUBLICATIONS

Van Zee et al. (1996), 'Protection Against Lethal *Escherichia coli* Bacteremia in Baboons (*Papio anubis*) by Pretreatment with a 55-kDa TNF Receptor (CD120a)-Ig Fusion Protein, Ro 45-2081', J. Immunol. 156:2221-2230.
Veronese et al., "Surface Modification of Proteins, Activation of Monomethoxy-Polyethylene Glycols by Phenylchloroformates and Modification of Ribonuclease and Superoxide Dismutase," Appll. Biochem. and Biotech., 11:141-152 (1985).
Wang et al;., Clin. Pharmacol. Ther., 76:628-638 (2004).
Wells et al., "Rapid Evolution of Peptide and Protein Binding Properties in vitro," Curr. Opin. Biotechnol., 3:355-362 (1992).
Whitty et al., Chemistry & Biology, 6:R107-R118 (1999).
Wieczorek et al. (1994), 'The Immunomodulatory Activity of Tetra- and Tripeptides of Tuftsin-Kentsin Group', Peptides 15(2):215-221.
Wieczorek et al. (1997), 'A Hexapeptide VTKFYF from C-Terminal Part of Interleukin-1 Receptor Antagonist, an Inhibitor of IL-1—IL-1 Receptor Interaction', Polish Journal of Pharmacology 49:107-117.
Williams et al. (1986), "Production of antibody-tagged enzymes by myeloma cells: application to DNA polymerate I Klenow fragment," Gene 43:319-324.
Wilson et al. (1998), 'Phage display: applications, innovations, and issues in phage and host biology', Can. J. Microbiol. 44:313-329.
Wrighton et al., "Small Peptides as Potent Mimetics of the Protein Hormone Erythropoietin," Science, 273:458-463 (1996).
Yanagida et al., Brit. J. Haematol., 99:739-745 (1997).
Yanofsky et al. (1996), 'High Affinity type I interleukin 1 receptor antagonists discovered by screening recombinant peptide libraries', PNAS 93:7381-7386.
Yin et al., "Effects of Antioxidants on the Hydrogen Peroxide-Mediated Oxidation of Methionine Residues in Granulocyte Colony-Stimulating Factor and Human Parathyroid Hormone Fragment 13-34," Pharm Res., 21(12):2377-2383 (2004).
Yoshida et al. (1984), 'The Activity of Synthetic analogs of Serum Thymic Factor (FTS) to Convert Mouse Pre-T Cells into Thy-1 Positive Cells', Int. J. Immunopharmac. 6(2):141-146.
Yu et al. (1994), 'Structural Basis for the Binding of Proline-Rich Peptides to SH3 Domains', Cell 76:933-945.
Zalipsky et al., "Poly(ethylene glycol)-Grafted Liposomes with Oligopeptide or Oligosaccharide Ligands Appended to the Termini of the Polymer Chains," Bioconjug Chem., 8:111-118 (1997).
Notice of References Cited PTO-892, dated Apr. 20, 2006 of U.S. Appl. No. 09/563,286.
Notice of References Cited PTO-892, dated Nov. 30, 2005 of U.S. Appl. No. 09/563,286.
Final Office Action, dated Oct. 16, 2007 of U.S. Appl. No. 09/563,286.
Final Office Action, dated Nov. 30, 2005 of U.S. Appl. No. 09/563,286.
Information Disclosures Statement, dated Feb. 19, 2008 of U.S. Appl. No. 09/563,286.
Information Disclosures Statement, dated Feb. 28, 2002 of U.S. Appl. No. 09/563,286.
Information Disclosures Statement, dated Feb. 28, 2008 of U.S. Appl. No. 09/563,286.
Information Disclosures Statement, dated Mar. 2, 2004 of U.S. Appl. No. 09/563,286.
Information Disclosures Statement, dated May 25, 2007 of U.S. Appl. No. 09/563,286.
Information Disclosures Statement, dated Jun. 7, 2002 of U.S. Appl. No. 09/563,286.
Information Disclosures Statement, dated Sep. 7, 2006 of U.S. Appl. No. 09/563,286.
Information Disclosures Statement, dated Dec. 19, 2000 of U.S. Appl. No. 09/563,286.
Information Disclosures Statement, dated Mar. 10, 2006 of U.S. Appl. No. 09/563,286.
Information Disclosures Statement, dated Apr. 20, 2006 of U.S. Appl. No. 09/563,286.
Response to Final Office Action, dated Feb. 19, 2008 of U.S. Appl. No. 09/563,286.
Response to Final Office Action, dated Feb. 28, 2006 of U.S. Appl. No. 09/563,286.
Response to Office Action, dated Sep. 15, 2005 of U.S. Appl. No. 09/563,286.
Response to Office Action, dated Oct. 26, 2006 of U.S. Appl. No. 09/563,286.
Response to Restriction Requirement, dated Aug. 5, 2004 of U.S. Appl. No. 09/563,286.
Response to Restriction Requirement, dated Dec. 2, 2004 of U.S. Appl. No. 09/563,286.
Restriction Requirement, dated May 5, 2004 of U.S. Appl. No. 09/563,286.
Restiction Requirement, dated Nov. 2, 2004 of U.S. Appl. No. 09/563,286.
Notice of References Cited PTO-892, dated Jun. 26, 2006 of US 7,189,827.
Information Disclosures Statement, dated Mar. 15, 2004 of US 7,189,827.
Information Disclosures Statement, dated May 9, 2006 of US 7,189,827.
Information Disclosures Statement, dated Jul. 31, 2003 of US 7,189,827.
Information Disclosures Statement, dated Oct. 26, 2006 of US 7,189,827.
Office Action, dated Jun. 26, 2006 of US 7,189,827.
Information Disclosures Statement, dated Jan. 19, 2006 of US20060189531.
Information Disclosures Statement, dated Oct. 29, 2008 of US20060189531.
Information Disclosures Statement, dated Dec. 13, 2007 of US20060189531.
Information Disclosures Statement, dated Feb. 19, 2008 of US20090011497.
Information Disclosures Statement, dated Sep. 12, 2008 of US20090011497.
Information Disclosures Statement, dated Oct. 22, 2008 of US20090011497.
Notice of References Cited PTO-892, dated Feb. 7, 2006 of US 7,332,474.
Final Office Action, dated Nov. 1, 2006 of US 7,332,474.
Information Disclosures Statement, dated Jun. 5, 2003 of US 7,332,474.
Office Action, dated Feb. 7, 2006 of US 7,332,474.
International Search Report of WO2003/031589A2.
Notice of References Cited PTO-892, dated Oct. 9, 2009 of US20080254020.
Information Disclosures Statement, dated Aug. 13, 2007 of US20080254020.
Office Action, dated Oct. 9, 2009 of US US20080254020.
International Search Report of WO2006/010057A2.
Information Disclosures Statement, dated Aug. 13, 2008 of US20090258017.
Information Disclosures Statement, dated Nov. 13, 2007 of US20090258017.
International Search Report of WO2007/124090A2.
Information Disclosures Statement, dated Mar. 17, 2008 of US20090053242.
Information Disclosures Statement, dated Sep. 4, 2007 of US20090053242.
International Search Report of WO2007/087428A2.
Notice of References Cited PTO-892, dated Apr. 2, 2009 of US20080070840.
Information Disclosures Statement, dated Oct. 2, 2009 of US20080070840.
Information Disclosures Statement, dated Nov. 13, 2007 of US20080070840.
Office Action, dated Apr. 2, 2009 of US20080070840.
International Search Report of WO2007/149529A2.
Notice of References Cited PTO-892, dated Jan. 8, 2007 of US20050080014.

(56) References Cited

OTHER PUBLICATIONS

Notice of References Cited PTO-892, dated Sep. 14, 2007 of US20050080014.
Advisory Action, dated Dec. 12, 2008 of US20050080014.
Final Office Action, dated Jun. 13, 2008 of US20050080014.
Final Office Action, dated Sep. 4, 2009 of US20050080014.
Information Disclosures Statement, dated Mar. 4, 2010 of US20050080014.
Information Disclosures Statement, dated Apr. 28, 2010 of US20050080014.
Information Disclosures Statement, dated Sep. 2, 2004 of US20050080014.
Information Disclosures Statement, dated Oct. 29, 2008 of US20050080014.
Notice of Appeal, dated Nov. 11, 2008 of US20050080014.
Office Action, dated Jan. 8, 2007 of US20050080014.
Office Action, dated Sep. 14, 2007 of US20050080014.
RCE, dated Mar. 4, 2010 of US20050080014.
RCE, dated Jun. 11, 2009 of US20050080014.
Response to Office Action, dated Mar. 13, 2008 of US20050080014.
Response to Office Action, dated Jul. 9, 2007 of US20050080014.
Response to Restriction Requirement, dated Jul. 10, 2006 of US20050080014.
Response to Restriction Requirement, dated Oct. 19, 2006 of US20050080014.
Restriction Requirement, dated May 26, 2006 of US20050080014.
Restriction Requirement, dated Aug. 26, 2010 of US20050080014.
Restriction Requirement, dated Sep. 26, 2006 of US20050080014.
Office Action, dated Mar. 31, 2010 of US20060189531.
Response to Office Action, dated Sep. 30, 2010 of US20060189531.
Office Action, dated Jun. 24, 2010 of US20090011497.
Final Office Action, dated May 7, 2010 of US20080254020.
Office Action, dated Apr. 30, 2010 of US20090053242.
Final Office Action, dated Aug. 19, 2010 of US20080070840.
International Search Report of WO2003/031589.
International Search Report of WO2007/124090.
International Search Report of WO2007/149529.
International Search Report of WO2007/087428.
International Search Report of WO2006/010057.
Robinson et al., "Optimizing the stability of single-chain proteins by linker length and composition mutagenesis," Proceedings of National Academy of Sciences, May 1998, vol. 95, pp. 5929-5934.
Office Action, dated Jan. 20, 2011 of US20060189531.
Response to Final Office Action, dated Nov. 8, 2010 of US20080254020.
Advisory Action, dated Nov. 16, 2010 of US20080254020.
Response to Office Action, dated Jan. 25, 2011 of US20050080014.
Response and RCE, dated Jan. 26, 2011 of US20080254020.
Crystal R., "Transfer of Genes to Humans: Early Lessons and Obstacles to Success," Science, 1995, vol. 270, pp. 404-410.
Verma et al., "Gene Therapy—Promises, Problem and Prospects," Nature, 1997, vol. 389, p. 239-242.
Anderson, W., "Human Gene Therapy," Nature, 1998, vol. 392, Suppl, pp. 25-30.
Marshall, E., "Gene Therapy's Growing Pains," Science, 1995, vol. 269, pp. 1050-1054.
Rubanyi, G., "The Future of Human Gene Therapy," Mol Aspects Med., 2001, vol. 22, pp. 113-142.
Stewart and Young, Solid Phase Peptide Synthesis (1969)—Table of Contents only.
Syed et al., Nature, 395:5111 (1998).
Ulich et al., Blood 86:971-976 (1995).
Van Zee. K. et al., The Journal of Immunology. 156:2221-2230 (1996).
Vigon, I. et al. Proc. Natl. Acad. Sci. USA 89:5640-5644 (1992).
Wells, J. A., et al., Ann. Rev. Biochem. 65:609-634 (1996).
Wrighton, N.C., et al., Science 273:458-469 (1996).
Wrighton, N.C., et al., Nature Biotechnology 15:1261-1265 (1997).
Zeigler et al., Blood 84:4045-4052 (1994).
Zheng, X., et al., The Journal of Immunology, 154:5590-5600 (1995).
Ngo et al., "Computational complexity, protein structure prediction and the Levinthal Paradox." The Protein Folding Problem and Tertiary Structure Prediction, pp. 443-440 and 492-495 (1994).
Wells. "Additivity of mutational effects in proteins." Biochemistry. 29:8509-8517 (1990).
Abuchowski and Davis, Soluble Ploymer-Enzyme Adducts, Enzymes as Drugs, Hocenberg and Roberts, eds., Wiley-Interscience, New York, NY, (1981), pp. 367-383.
Adjei et al., Pharmaceutical Research 7:565-569 (1990).
Adjei et al., International Journal of Pharmaceutics 61: 135-144 (1990).
Alexander et al., Blood 87:2162-2170 (1996).
Bartley et al., Cell 77:1117-1124 (1994).
Basser et al., Lancet 348:1279-81 (1996).
Braquet et al., Journal of Cardiovascular Pharmacology 13 (suppl.5): s. 143-146 (1989).
Capon et al., Nature 337:525-531 (1989).
Chang et al., Journal of Biological Chemistry 270:511-517 (1995).
Choi et al., Blood 85:402-413 (1995).
Clackson, T. et al., Science 267:383-386 (1995).
Creighton, T.E., Proteins: Structure and Molecule Properties, W.H. Freeman & Co., San Francisco, pp. 70-86 (1983).
Cwirla, S.E. et al., Science 276:1696-1699 (1997).
Davis et al., Biochem. Intl. 10:395-404 (1985).
Debili, N. et al., Blood 85:391-401 (1995).
Debs et al., The Journal of Immunology 140:3482-3488 (1988).
de Sauvage et al., Nature 369:533-538 (1994).
Devlin, J.J. et al., Science 249:404 (1990).
Duncan, Nature, 332:563 (1988).
Ellison, J.W., et al., Nucleic Acids Res. 10:4071-4079 (1982).
Erickson et al., The Proteins, 3rd ed., vol. 2, pp. 257-527 (1976).
Finn et al., THe Proteins, 3rd ed., vol. 2, pp. 105-253 (1976).
Fisher. C. et al., N. Engl. J. Med., 334:1697-1702 (1996).
Gumey et al., Blood 85:981-988 (1995).
Harvill et al., Immunotechnology, 1:95-105 (1995).
Hokom, M.M., et al., Blood 86:4486-4492 (1995).
Hubbard et al., Annals of Internal Medicine, 111:206-212 (1989).
Jefferis et al., Immunology Letters, vol. 44, pp. 111-117 (1995).
Jefferis et al., Molecular Immunology, vol. 27, pp. 1237-1240 (1990).
Johnson et al., Biochemistry, vol. 37, pp. 3699-3710 (1998).
Kaushansky et al., Nature 369:568-571 (1994).
Kato et al., Journal of Biochemistry, 118:229-236 (1995).
Kay et al., Reviews—Research Focus, vol. 3, No. 8, pp. 370-378 (1998).
Kuter et al., Proc. Natl. Acad. Sci. USA 91:11104-11108 (1994).
Livnah, O. et al., Science 273:464-471 (1996).
Lok, S. et al., Nature 369:565-8 (1994).
Marshall, K. Modern Pharmaceutics, Edited by G.S. Banker and C. T. Rhodes Chapter 10, 1979.
Merrifield, in Chem. Polypeptides, pp. 335-361 (Katsoyannis and Panayotis eds. 1973).
Merrifield, J. Am. Chem. Soc. 85:2149 (1963).
Methia et al., Blood 82:1395-1401 (1993).
Newmark, et al., J. Appl. Biochem. 4:185-189 (1982).
Palacios, R. et al., Cell 41:727 (1985).
Rasko et al., Stem Cells 15:33-42 (1997).
Ravin et al., Remington's Pharmaceutical Sciences, 18th Ed., (1990, Mack Publishing Co., Easton, PA 18042) pp. 1435-1712.
Sarmay, Molecule Immunology, vol. 29, No. 5, 633-639 (1992).
Scott, J.K., et al., Science 249:386 (1990).
Sheridan et al., Platelets, vol. 8., pp. 319-332 (1997).
Smith et al., J. Clin. Invest., 84:1145-1146 (1989).
Office Action, dated Nov. 10, 2011 of US20060189531.
Office Action, dated May 31, 2013 of US20060189531.

\* cited by examiner

```
      ATGGACAAAACTCACACATGTCCACCTTGTCCAGCTCCGGAACTCCTGGGGGACCGTCA
1     ------------+---------+---------+---------+---------+---------+ 60
      TACCTGTTTTGAGTGTGTACAGGTGGAACAGGTCGAGGCCTTGAGGACCCCCCTGGCAGT a     M  D  K  T  H  T  C  P  P  C  P  A  P  E  L  L  G  G  P  S  -

GTCTTCCTCTTCCCCCCAAAACCCAAGGACACCCTCATGATCTCCCGGACCCCTGAGGTC
61    ------------+---------+---------+---------+---------+---------+ 120
      CAGAAGGAGAAGGGGGGTTTTGGGTTCCTGTGGGAGTACTAGAGGGCCTGGGGACTCCAG a     V  F  L  F  P  P  K  P  K  D  T  L  M  I  S  R  T  P  E  V  -

ACATGCGTGGTGGTGGACGTGAGCCACGAAGACCCTGAGGTCAAGTTCAACTGGTACGTG
121   ------------+---------+---------+---------+---------+---------+ 180
      TGTACGCACCACCACCTGCACTCGGTGCTTCTGGGACTCCAGTTCAAGTTGACCATGCAC a     T  C  V  V  V  D  V  S  H  E  D  P  E  V  K  F  N  W  Y  V  -

GACGGCGTGGAGGTGCATAATGCCAAGACAAAGCCGCGGGAGGAGCAGTACAACAGCACG
181   ------------+---------+---------+---------+---------+---------+ 240
      CTGCCGCACCTCCACGTATTACGGTTCTGTTTCGGCGCCCTCCTCGTCATGTTGTCGTGC a     D  G  V  E  V  H  N  A  K  T  K  P  R  E  E  Q  Y  N  S  T  -

TACCGTGTGGTCAGCGTCCTCACCGTCCTGCACCAGGACTGGCTGAATGGCAAGGAGTAC
241   ------------+---------+---------+---------+---------+---------+ 300
      ATGGCACACCAGTCGCAGGAGTGGCAGGACGTGGTCCTGACCGACTTACCGTTCCTCATG a     Y  R  V  V  S  V  L  T  V  L  H  Q  D  W  L  N  G  K  E  Y  -

AAGTGCAAGGTCTCCAACAAAGCCCTCCCAGCCCCCATCGAGAAAACCATCTCCAAAGCC
301   ------------+---------+---------+---------+---------+---------+ 360
      TTCACGTTCCAGAGGTTGTTTCGGGAGGGTCGGGGGTAGCTCTTTTGGTAGAGGTTTCGG a     K  C  K  V  S  N  K  A  L  P  A  P  I  E  K  T  I  S  K  A  -

AAAGGGCAGCCCCGAGAACCACAGGTGTACACCCTGCCCCCATCCCGGGATGAGCTGACC
361   ------------+---------+---------+---------+---------+---------+ 420
      TTTCCCGTCGGGGCTCTTGGTGTCCACATGTGGGACGGGGGTAGGGCCCTACTCGACTGG a     K  G  Q  P  R  E  P  Q  V  Y  T  L  P  P  S  R  D  E  L  T  -

AAGAACCAGGTCAGCCTGACCTGCCTGGTCAAAGGCTTCTATCCCAGCGACATCGCCGTG
421   ------------+---------+---------+---------+---------+---------+ 480
      TTCTTGGTCCAGTCGGACTGGACGGACCAGTTTCCGAAGATAGGGTCGCTGTAGCGGCAC a     K  N  Q  V  S  L  T  C  L  V  K  G  F  Y  P  S  D  I  A  V  -

GAGTGGGAGAGCAATGGGCAGCCGGAGAACAACTACAAGACCACGCCTCCCGTGCTGGAC
481   ------------+---------+---------+---------+---------+---------+ 540
      CTCACCCTCTCGTTACCCGTCGGCCTCTTGTTGATGTTCTGGTGCGGAGGGCACGACCTG
```

TCCGACGGCTCCTTCTTCCTCTACAGCAAGCTCACCGTGGACAAGAGCAGGTGGCAGCAG
541  ------+---------+---------+---------+---------+---------+  600
     AGGCTGCCGAGGAAGAAGGAGATGTCGTTCGAGTGGCACCTGTTCTCGTCCACCGTCGTC a    S  D  G  S  F  F  L  Y  S  K  L  T  V  D  K  S  R  W  Q  Q   -

GGGAACGTCTTCTCATGCTCCGTGATGCATGAGGCTCTGCACAACCACTACACGCAGAAG
601  ------+---------+---------+---------+---------+---------+  660
     CCCTTGCAGAAGAGTACGAGGCACTACGTACTCCGAGACGTGTTGGTGATGTGCGTCTTC a    G  N  V  F  S  C  S  V  M  H  E  A  L  H  N  H  Y  T  Q  K   -

AGCCTCTCCCTGTCTCCGGGTAAA
661  ------+---------+----  684
     TCGGAGAGGGACAGAGGCCCATTT a    S  L  S  L  S  P  G  K
```

FIG. 1B

THROMBOPOIETIC COMPOUNDS

This application is a divisional application of U.S. patent application Ser. No. 10/933,133, which was filed Sep. 2, 2004, which is a continuation of U.S. patent application Ser. No. 09/422,838, now issued U.S. Pat. No 6,835,809, which was filed Oct. 22, 1999, which in turn claims benefit under 35 U.S.C. §119 of U.S. Provisional Patent Application Ser. No. 60/105,348, which was filed Oct. 23, 1998, each of which is incorporated herein by reference in its entirety.

REFERENCE TO SEQUENCE LISTING

The present application is being filed along with a Sequence Listing in electronic format. The Sequence Listing is provided as a file entitled A-533-US-DIV2_SeqList.txt, created Jun. 11, 2009, which is 42.1 KB in size. The information in the electronic format of the Sequence Listing is incorporated herein by reference in its entirety.

FIELD OF THE INVENTION

Generally, the invention relates to the field of compounds, especially peptides and polypeptides, that have thrombopoietic activity. The compounds of the invention may be used to increase production of platelets or platelet precursors (e.g., megakaryocytes) in a mammal.

BACKGROUND OF THE INVENTION

This invention relates to compounds, especially peptides, that have the ability to stimulate in vitro and in vivo production of platelets and their precursor cells such as megakaryocytes. Before discussing the nature of the inventive compounds, the following is provided as a background regarding two proteins that have thrombopoietic activity: thrombopoietin (TPO) and megakaryocyte growth and development factor (MGDF).

The cloning of endogenous thrombopoietin (TPO) (Lok et al., Nature 369:568-571 (1994); Bartley et al., Cell 77:1117-1124 (1994); Kuter et al., Proc. Natl. Acad. Sci. USA 91:11104-11108 (1994); de Sauvage et al., Nature 369:533-538 (1994); Kato et al., Journal of Biochemistry 119:229-236 (1995); Chang et al., Journal of Biological Chemistry 270:511-514 (1995)) has rapidly increased our understanding of megakaryopoiesis (megakaryocyte production) and thrombopoiesis (platelet production).

Endogenous human TPO, a 60 to 70 kDa glycosylated protein primarily produced in the liver and kidney, consists of 332 amino acids (Bartley et al., Cell 77:1117-1124 (1994); Chang et al., Journal of Biological Chemistry 270:511-514 (1995)). The protein is highly conserved between different species, and has 23% homology with human erythropoietin (Gurney et al., Blood 85:981-988 (1995)) in the amino terminus (amino acids 1 to 172) (Bartley et al., Cell 77:1117-1124 (1994)). Endogenous TPO has been shown to possess all of the characteristics of the key biological regulator of thrombopoiesis. Its in vitro actions include specific induction of megakaryocyte colonies from both purified murine hematopoietic stem cells (Zeigler et al., Blood 84:4045-4052 (1994)) and human $CD34^+$ cells (Lok et al., Nature 369:568-571 (1994); Rasko et al., Stem Cells 15:33-42 (1997)), the generation of megakaryocytes with increased ploidy (Broudy et al., Blood 85:402-413 (1995)), and the induction of terminal megakaryocyte maturation and platelet production (Zeigler et al., Blood 84:4045-4052 (1994); Choi et al., Blood 85:402-413 (1995)). Conversely, synthetic antisense oligodeoxynucleotides to the TPO receptor (c-Mpl) significantly inhibit the colony-forming ability of megakaryocyte progenitors (Methia et al., Blood 82:1395-1401 (1993)). Moreover, c-Mpl knock-out mice are severely thrombocytopenic and deficient in megakaryocytes (Alexander et al., Blood 87:2162-2170 (1996)).

Recombinant human MGDF (rHuMGDF, Amgen Inc., Thousand Oaks, Calif.) is another thrombopoietic polypeptide related to TPO. It is produced using *E. coli* transformed with a plasmid containing cDNA encoding a truncated protein encompassing the amino-terminal receptor-binding domain of human TPO (Ulich et al., Blood 86:971-976 (1995)). The polypeptide is extracted, refolded, and purified, and a poly[ethylene glycol] (PEG) moiety is covalently attached to the amino terminus. The resulting molecule is referred to herein as PEG-rHuMGDF or MGDF for short.

Various studies using animal models (Ulich, T. R. et al., Blood 86:971-976 (1995); Hokom, M. M. et al., Blood 86:4486-4492 (1995)) have clearly demonstrated the therapeutic efficacies of TPO and MGDF in bone marrow transplantation and in the treatment of thrombocytopenia, a condition that often results from chemotherapy or radiation therapy. Preliminary data in humans have confirmed the utility of MGDF in elevating platelet counts in various settings. (Basser et al., Lancet 348:1279-81 (1996); Kato et al., Journal of Biochemistry 119:229-236 (1995); Ulich et al., Blood 86:971-976 (1995)). MGDF might be used to enhance the platelet donation process, since administration of MGDF increases circulating platelet counts to about three-fold the original value in healthy platelet donors.

TPO and MGDF exert their action through binding to the c-Mpl receptor which is expressed primarily on the surface of certain hematopoietic cells, such as megakaryocytes, platelets, $CD34^+$ cells and primitive progenitor cells (Debili, N. et al., Blood 85:391-401 (1995); de Sauvage, F. J. et al, Nature 369:533-538 (1994); Bartley, T. D., et al., Cell 77:1117-1124 (1994); Lok, S. et al., Nature 369: 565-8 (1994)). Like most receptors for interleukins and protein hormones, c-Mpl belongs to the class I cytokine receptor superfamily (Vigon, I. et al., Proc. Natl. Acad. Sci. USA 89:5640-5644 (1992)). Activation of this class of receptors involves ligand-binding induced receptor homodimerization which in turn triggers the cascade of signal transducing events.

In general, the interaction of a protein ligand with its receptor often takes place at a relatively large interface. However, as demonstrated in the case of human growth hormone bound to its receptor, only a few key residues at the interface actually contribute to most of the binding energy (Clackson, T. et al., Science 267:383-386 (1995)). This and the fact that the bulk of the remaining protein ligand serves only to display the binding epitopes in the right topology makes it possible to find active ligands of much smaller size.

In an effort toward this, the phage peptide library display system has emerged as a powerful technique in identifying small peptide mimetics of large protein ligands (Scott, J. K. et al., Science 249:386 (1990); Devlin, J. J. et al., Science 249: 404 (1990)). By using this technique, small peptide molecules that act as agonists of the c-Mpl receptor were discovered (Cwirla, S. E. et al., Science 276:1696-1699 (1997)).

In such a study, random small peptide sequences displayed as fusions to the coat proteins of filamentous phage were affinity-eluted against the antibody-immobilized extracellular domain of c-Mpl and the retained phages were enriched for a second round of affinity purification. This binding selection and repropagation process was repeated many times to enrich the pool of tighter binders. As a result, two families of c-Mpl-binding peptides, unrelated to each other in their sequences, were first identified. Mutagenesis libraries were then created to further optimize the best binders, which finally led to the isolation of a very active peptide with an $IC_{50}=2$ nM and an $EC_{50}=400$ nM (Cwirla, S. E. et al., Science 276:1696-1699 (1997)). This 14-residue peptide, designated as a TMP (for TPO Mimetic Peptide), has no apparent sequence homology to TPO or MGDF. The structure of this TMP compound is as follows:

SEQ ID NO: 1
Ile Glu Gly Pro Thr Leu Arg Gln Trp Leu Ala Ala
Arg Ala or

SEQ ID NO: 1
IEGPTLRQWLAARA using single letter amino acid abbreviations.

Previously, in a similar study on EPO mimetic peptides, an EPO mimetic peptide (EMP) was discovered using the same technique (Wrighton, N. C. et al., Science 273:458-463 (1996)), and was found to act as a dimer in binding to the EPO receptor (EPOR). The (ligand)$_2$/(receptor)$_2$ complex thus formed had a C2

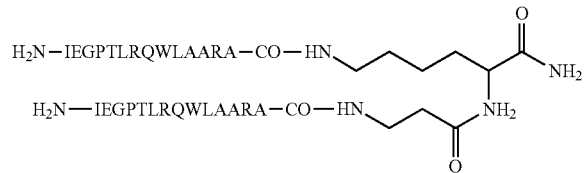

symmetry according to X-ray crystallographic data (Livnah, O. et al., Science 273:464-471 (1996)). Based on this structural information, a covalently linked dimer of EMP in which the C-termini of two EMP monomers were crosslinked with a flexible spacer was designed and found to have greatly enhanced binding as well as in vitro/in vivo bioactivity (Wrighton, N. C., et al., Nature Biotechnology 15:1261-1265 (1997)).

A similar C-terminal dimerization strategy was applied to the TPO mimetic peptide (TMP) (Cwirla, S. E. et al., Science 276:1696-1699 (1997)). It was found that a C-terminally linked dimer (C—C link) of TMP had an improved binding affinity of 0.5 nM and a remarkably increased in vitro activity ($EC_{50}=0.1$ nM) in cell proliferation assays (Cwirla, S. E. et al., Science 276:1696-1699 (1997)). The structure of this TMP C—C dimer is shown below: (SEQ ID NO:2)

In another aspect of the present invention, the tandem dimers may be further attached to one or more moieties that are derived from immunoglobulin proteins, referred to generally as the Fc region of such immunoglobulins. The resulting compounds are referred to as Fc fusions of TMP tandem dimers.

The following is a brief background section relating to the Fc regions of antibodies that are useful in connection with some of the present compounds.

Antibodies comprise two functionally independent parts, a variable domain known as "Fab", which binds antigen, and a constant domain, known as "Fc" which provides the link to effector functions such as complement fixation or phagocytosis. The Fc portion of an immunoglobulin has a long plasma half-life, whereas the Fab is short-lived. (Capon, et al., Nature 337:525-531 (1989)).

Therapeutic protein products have been constructed using the Fc domain to attempt to provide longer half-life or to incorporate functions such as Fc receptor binding, protein A binding, complement fixation, and placental transfer which all reside in the Fc region of immunoglobulins (Capon, et al., Nature 337:525-531 (1989)). For example, the Fc region of an IgG1 antibody has been fused to CD30-L, a molecule which binds CD30 receptors expressed on Hodgkin's Disease tumor cells, anaplastic lymphoma cells, T-cell leukemia cells and other malignant cell types. See, U.S. Pat. No. 5,480,981. IL-10, an anti-inflammatory and antirejection agent has been fused to murine Fcγ2a in order to increase the cytokine's short circulating half-life (Zheng, X. et al., The Journal of Immunology, 154: 5590-5600 (1995)). Studies have also evaluated the use of tumor necrosis factor receptor linked with the Fc protein of human IgG1 to treat patients with septic shock (Fisher, C. et al., N. Engl. J. Med., 334: 1697-1702 (1996); Van Zee, K. et al., The Journal of Immunology, 156: 2221-2230 (1996)). Fc has also been fused with CD4 receptor to produce a therapeutic protein for treatment of AIDS. See, Capon et al., Nature, 337:525-531 (1989). In addition, interleukin 2 has been fused to the Fc portion of IgG1 or IgG3 to overcome the short half life of interleukin 2 and its systemic toxicity. See, Harvill et al., Immunotechnology, 1: 95-105 (1995).

In spite of the availability of TPO and MGDF, there remains a need to provide additional compounds that have a biological activity of stimulating the production of platelets (thrombopoietic activity) and/or platelet precursor cells, especially megakaryocytes (megakaryopoietic activity). The present invention provides new compounds having such activity(ies), and related aspects.

SUMMARY OF THE INVENTION

The present invention provides a group of compounds that are capable of binding to and triggering a transmembrane signal through, i.e., activating, the c-Mpl receptor, which is the same receptor that mediates the activity of endogenous thrombopoietin (TPO). Thus, the inventive compounds have thrombopoietic activity,
i.e., the ability to stimulate, in vivo and in vitro, the production of platelets, and/or megakaryocytopoietic activity, i.e., the ability to stimulate, in vivo and in vitro, the production of platelet precursors.

In a first preferred embodiment, the inventive compounds comprise the following general structure:

$TMP_1$-$(L_1)_n$-$TMP_2$ wherein $TMP_1$ and $TMP_2$ are each independently selected from the group of compounds comprising the core structure:

$X_2$-$X_3$-$X_4$-$X_5$-$X_6$-$X_7$-$X_8$-$X_9$-$X_{10}$, wherein, $X_2$ is selected from the group consisting of Glu, Asp, Lys, and Val;

$X_3$ is selected from the group consisting of Gly and Ala;

$X_4$ is Pro;

$X_5$ is selected from the group consisting of Thr and Ser;

$X_6$ is selected from the group consisting of Leu, Ile, Val, Ala, and Phe;

$X_7$ is selected from the group consisting of Arg and Lys;

$X_8$ is selected from the group consisting of Gln, Asn, and Glu;

$X_9$ is selected from the group consisting of Trp, Tyr, Cys, Ala, and Phe;

$X_{10}$ is selected from the group consisting of Leu, Ile, Val, Ala, Phe, Met, and Lys;

L₁ is a linker as described herein; and
n is 0 or 1;
and physiologically acceptable salts thereof.

In one embodiment, L₁ comprises $(Gly)_n$, wherein n is 1 through 20, and when n is greater than 1, up to half of the Gly residues may be substituted by another amino acid selected from the remaining 19 natural amino acids or a stereoisomer thereof.

In addition to the core structure $X_2$-$X_{10}$ set forth above for TMP₁ and TMP₂, other related structures are also possible wherein one or more of the following is added to the TMP₁ and/or TMP₂ core structure: $X_1$ is attached to the N-terminus and/or $X_{11}$, $X_{12}$, $X_{13}$, and/or $X_{14}$ are attached to the C-terminus, wherein $X_1$, $X_{12}$, $X_{13}$, and $X_{14}$ are as follows:

$X_1$ is selected from the group consisting of Ile, Ala, Val, Leu, Ser, and Arg;

$X_{11}$ is selected from the group consisting of Ala, Ile, Val, Leu, Phe, Ser, Thr, Lys, His, and Glu;

$X_{12}$ is selected from the group consisting of Ala, Ile, Val, Leu, Phe, Gly, Ser, and Gln;

$X_{13}$ is selected from the group consisting of Arg, Lys, Thr, Val, Asn, Gln, and Gly; and $X_{14}$ is selected from the group consisting of Ala, Ile, Val, Leu, Phe, Thr, Arg, Glu, and Gly.

In a second preferred embodiment, the inventive compounds have the general formula:

$$(Fc)_m\text{-}(L_2)_q\text{-}TMP_1\text{-}(L_1)_n\text{-}TMP_2\text{-}(L_3)_r\text{-}(Fc)_p$$

wherein TMP₁, TMP₂ and n are each as described above; L₁, L₂ and L₃ are linker groups which are each independently selected from the linker groups described herein;
Fc is an Fc region of an immunoglobulin (as defined herein below); m, p, q and r are each independently selected from the group consisting of 0 and 1, wherein at least one of m or p is 1, and further wherein if m is 0 then q is 0, and if p is 0, then r is 0; and physiologically acceptable salts thereof. In one embodiment, L₁, L₂, and L₃ independently comprise $(Gly)_n$, wherein n is 1 through 20, and when n is greater than 1, up to half of the Gly residues may be substituted by another amino acid selected from the remaining 19 natural amino acids or a stereoisomer thereof.

Derivatives of the above compounds (described below) are also encompassed by this invention.

The compounds of this invention are preferably peptides, and they may be prepared by standard synthetic methods or any other methods of preparing peptides. The compounds of this invention that encompass non-peptide portions may be synthesized by standard organic chemistry reactions, in addition to standard peptide chemistry reactions when applicable.

The compounds of this invention may be used for therapeutic or prophylactic purposes by incorporating them with appropriate pharmaceutical carrier materials and administering an effective amount to a subject, such as a human (or other mammal). Other related aspects are also included in the instant invention.

BRIEF DESCRIPTION OF THE FIGURES

Numerous other aspects and advantages of the present invention will therefore be apparent upon consideration of the following detailed description thereof, reference being made to the drawings wherein:

FIG. 1 shows exemplary Fc polynucleotide and protein sequences (SEQ ID NO: 3 is the coding strand reading 5'→3', SEQ ID NO: 4 is the complementary strand reading 3'→5'; and SEQ ID NO: 5 is the encoded amino acids sequence) of human IgG1 that may be used in the Fc fusion compounds of this invention.

FIG. 6A shows an Fc fusion compound wherein the Fc moiety is fused at the N-terminus of the TMP dimer, and wherein the Fc portion is a monomeric (single chain) form. FIG. 6B shows an Fc fusion compound wherein the Fc region is fused at the N-terminus of the TMP dimer, and wherein the Fc portion is dimeric, and one Fc monomer is attached to a TMP dimer. FIG. 6C shows an Fc fusion compound wherein the Fc moiety is fused at the N-terminus of the TMP dimer, and wherein the Fc portion is dimeric and each Fc monomer is attached to a TMP dimer.

DETAILED DESCRIPTION OF THE PREFERRED EMBODIMENTS

Figure 2:
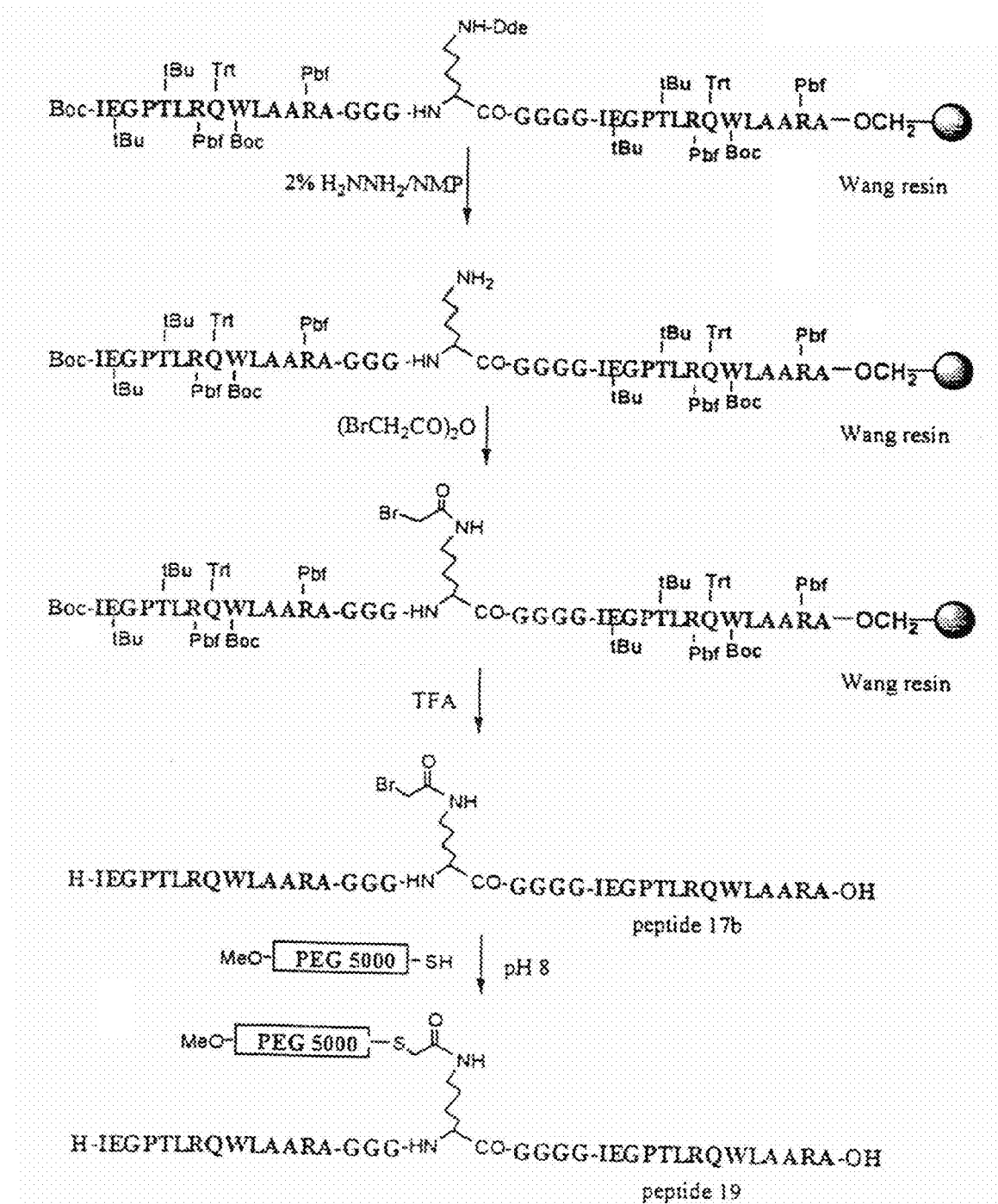
FIG. 2 shows a synthetic scheme for the preparation of pegylated peptide 19 (SEQ ID NO:17).

In an effort to seek small structures as lead compounds in the development of therapeutic agents with more desirable properties, a different type of dimer of TMP and related structures were designed in which the C-terminus of one TMP peptide was linked to the N-terminus of a second TMP peptide, either directly or via a linker and the effects of this dimerization strategy on the bioactivity of the resulting dimeric molecules were then investigated. In some cases, these so-called tandem dimers (C—N link) were designed to have linkers between the two monomers, the linkers being preferably composed of natural amino acids, therefore rendering their synthesis accessible to recombinant technologies.

The present invention is based on the discovery of a group of compounds that have thrombopoietic activity and which are thought to exert their activity by binding to the endogenous TPO receptor, c-Mpl.

Compounds and Derivatives

In a first preferred embodiment, the inventive compounds comprise the following general structure:

$$TMP_1\text{-}(L_1)_n\text{-}TMP_2$$

wherein TMP$_1$ and TMP$_2$ are each independently selected from the group of compounds comprising the core structure:

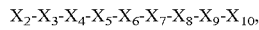

wherein,

X$_2$ is selected from the group consisting of Glu, Asp, Lys, and Val;

X$_3$ is selected from the group consisting of Gly and Ala;

X$_4$ is Pro;

X$_5$ is selected from the group consisting of Thr and Ser;

X$_6$ is selected from the group consisting of Leu, Ile, Val, Ala, and Phe;

X$_7$ is selected from the group consisting of Arg and Lys;

X$_8$ is selected from the group consisting of Gln, Asn, and Glu;

X$_9$ is selected from the group consisting of Trp, Tyr, and Phe;

X$_{10}$ is selected from the group consisting of Leu, Ile, Val, Ala, Phe, Met, and Lys;

L$_1$ is a linker as described herein; and n is 0 or 1;

and physiologically acceptable salts thereof.

In one embodiment, L$_1$, comprises (Gly)$_n$, wherein n is 1 through 20, and when n is greater than 1, up to half of the Gly residues may be substituted by another amino acid selected from the remaining 19 natural amino acids or a stereoisomer thereof.

In addition to the core structure X$_2$-X$_{10}$ set forth above for TMP$_1$ and TMP$_2$, other related structures are also possible wherein one or more of the following is added to the TMP$_1$ and/or TMP$_2$ core structure: X$_1$ is attached to the N-terminus and/or X$_{11}$, X$_{12}$, X$_{13}$, and/or X$_{14}$ are attached to the C-terminus, wherein X$_1$, X$_{11}$, X$_{12}$, X$_{13}$, and X$_{14}$ are as follows:

X$_1$ is selected from the group consisting of Ile, Ala, Val, Leu, Ser, and Arg;

X$_{11}$ is selected from the group consisting of Ala, Ile, Val, Leu, Phe, Ser, Thr, Lys, His, and Glu;

X$_{12}$ is selected from the group consisting of Ala, Ile, Val, Leu, Phe, Gly, Ser, and Gln;

X$_{13}$ is selected from the group consisting of Arg, Lys, Thr, Val, Asn, Gln, and Gly; and X$_{14}$ is selected from the group consisting of Ala, Ile, Val, Leu, Phe, Thr, Arg, Glu, and Gly.

The term "TMP" is used to mean a moiety made up of, i.e., comprising, at least 9 subunits (X$_2$-X$_{10}$), wherein X$_2$-X$_{10}$ comprise the core structure. The X$_2$-X$_{14}$ subunits are preferably amino acids independently selected from among the 20 naturally-occurring amino acids, however, the invention embraces compounds where X$_2$-X$_{14}$ are independently selected from the group of atypical, non-naturally occurring amino acids well known in the art. Specific preferred amino acids are identified for each position. For example, X$_2$ may be Glu, Asp, Lys, or Val. Both three-letter and single letter abbreviations for amino acids are used herein; in each case, the abbreviations are the standard ones used for the 20 naturally-occurring amino acids or well-known variations thereof. These amino acids may have either L or D stereochemistry (except for Gly, which is neither L nor D), and the TMPs may comprise a combination of stereochemistries. However, the L stereochemistry is preferred for all of the amino acids in the TMP chain. The invention also provides reverse TMP molecules wherein the amino terminal to carboxy terminal sequence of the amino acids is reversed. For example, the reverse of a molecule having the normal sequence X$_1$-X$_2$-X$_3$ would be X$_3$-X$_2$-X$_1$. The invention also provides retro-reverse TMP molecules wherein, like a reverse TMP, the amino terminal to carboxy terminal sequence of amino acids is reversed and residues that are normally "L" enatiomers in TMP are altered to the "D" stereoisomer form.

Additionally, physiologically acceptable salts of the TMPs are also encompassed. "Physiologically acceptable salts" means any salts that are known or later discovered to be pharmaceutically acceptable. Some specific preferred examples are: acetate, trifluoroacetate, hydrochloride, hydrobromide, sulfate, citrate, tartrate, glycolate, oxalate.

It is also contemplated that "derivatives" of the TMPs may be substituted for the above-described TMPs. Such derivative TMPs include moieties wherein one or more of the following modifications have been made:

one or more of the peptidyl [—C(O)NR—] linkages (bonds) have been replaced by a non-peptidyl linkage such as a —CH$_2$-carbamate linkage [—CH$_2$—OC(O)NR—]; a phosphonate linkage; a —CH$_2$-sulfonamide [—CH$_2$—S(O)$_2$NR—] linkage; a urea [—NHC(O)NH—] linkage; a —CH$_2$-secondary amine linkage; or an alkylated peptidyl linkage [—C(O)NR$^6$— where R$^6$ is lower alkyl];

peptides wherein the N-terminus is derivatized to a —NRR$^1$ group; to a —NRC(O)R group; to a —NRC(O)OR group; to a —NRS(O)$_2$R group; to a —NHC(O)NHR group, where R and R$^1$ are hydrogen or lower alkyl, with the proviso that R and R$^1$ are not both hydrogen; to a succinimide group; to a benzyloxycarbonyl-NH— (CBZ—NH—) group; or to a benzyloxycarbonyl-NH— group having from 1 to 3 substituents on the phenyl ring selected from the group consisting of lower alkyl, lower alkoxy, chloro, and bromo; and peptides wherein the free C terminus is derivatized to —C(O)R$^2$ where R$^2$ is selected from the group consisting of lower alkoxy and —NR$^3$R$^4$ where R$^3$ and R$^4$ are independently selected from the group consisting of hydrogen and lower alkyl. By "lower" is meant a group having from 1 to 6 carbon atoms.

Additionally, modifications of individual amino acids may be introduced into the TMP molecule by reacting targeted amino acid residues of the peptide with an organic derivatizing agent that is capable of reacting with selected side chains or terminal residues. The following are exemplary:

Lysinyl and amino terminal residues may be reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine guanidino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizole and tetranitromethane may be used to form O-acetyl tyrosyl species and 3-nitro derivatives, respectively.

Carboxyl side groups (aspartyl or glutamyl) may be selectively modified by reaction with carbodiimides (R'—N=C=N—R') such as 1-cyclohexyl-3-(2-morpholinyl-(4-ethyl) carbodiimide or 1-ethyl-3-(4-azonia-4,4- dimethylpentyl)carbodiimide. Furthermore, aspartyl and glutamyl residues may be converted to asparaginyl and glutaminyl residues by reaction with ammonium ions.

Glutaminyl and asparaginyl residues are frequently deamidated to the corresponding glutamyl and aspartyl residues. Alternatively, these residues may be deamidated under mildly acidic conditions. Either form of these residues falls within the scope of this invention.

Derivatization with bifunctional agents is useful for cross-linking the peptides or their functional derivatives to a water-insoluble support matrix or to other macromolecular carriers. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 may be employed for protein immobilization.

Other possible modifications include hydroxylation of proline and lysine, phosphorylation of hydroxyl groups of seryl or threonyl residues, oxidation of the sulfur atom in Cys, methylation of the alpha-amino groups of lysine, arginine, and histidine side chains (Creighton, T. E., Proteins: Structure and Molecule Properties, W. H. Freeman & Co., San Francisco, pp. 79-86 (1983)), acetylation of the N-terminal amine, and, in some instances, amidation of the C-terminal carboxyl groups.

Such derivatized moieties preferably improve one or more characteristics including thrombopoietic activity, solubility, absorption, biological half life, and the like of the inventive compounds. Alternatively, derivatized moieties result in compounds that have the same, or essentially the same, characteristics and/or properties of the compound that is not derivatized. The moieties may alternatively eliminate or attenuate any undesirable side effect of the compounds and the like.

In addition to the core structure set forth above, $X_2$-$X_{10}$, other structures that are specifically contemplated are those in which one or more additional X groups are attached to the core structure. Thus, $X_1$, and/or $X_{11}$, $X_{12}$, $X_{13}$, and $X_{14}$ may be attached to the core structure. Some exemplary additional structures are the following:

$X_2$-$X_3$-$X_4$-$X_5$-$X_6$-$X_7$-$X_8$-$X_9$-$X_{10}$-$X_{11}$;

$X_2$-$X_3$-$X_4$-$X_5$-$X_6$-$X_7$-$X_8$-$X_9$-$X_{10}$-$X_{11}$-$X_{12}$;

$X_2$-$X_3$-$X_4$-$X_5$-$X_6$-$X_7$-$X_8$-$X_9$-$X_{10}$-$X_{11}$-$X_{12}$-$X_{13}$;

$X_2$-$X_3$-$X_4$-$X_5$-$X_6$-$X_7$-$X_8$-$X_9$-$X_{10}$-$X_{11}$-$X_{12}$-$X_{13}$-$X_{14}$;

$X_1$-$X_2$-$X_3$-$X_4$-$X_5$-$X_6$-$X_7$-$X_8$-$X_9$-$X_{10}$;

$X_1$-$X_2$-$X_3$-$X_4$-$X_5$-$X_6$-$X_7$-$X_8$-$X_9$-$X_{10}$-$X_{11}$;

$X_1$-$X_2$-$X_3$-$X_4$-$X_5$-$X_6$-$X_7$-$X_8$-$X_9$-$X_{10}$-$X_{11}$-$X_{12}$;

$X_1$-$X_2$-$X_3$-$X_4$-$X_5$-$X_6$-$X_7$-$X_8$-$X_9$-$X_{10}$-$X_{11}$-$X_{12}$-$X_{13}$;

$X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$;

wherein $X_1$ through $X_{14}$ are as described above. Each of $TMP_1$ and $TMP_2$ may be the same or different in sequence and/or length. In some preferred embodiments, $TMP_1$ and $TMP_2$ are the same.

A particularly preferred TMP is the following:

(SEQ ID NO: 1)
Ile-Glu-Gly-Pro-Thr-Leu-Arg-Gln-Trp-Leu-Ala-Ala-Arg-Ala.

As used herein "comprising" means, inter alia, that a compound may include additional amino acids on either or both of the - or C-termini of the given sequence. However, as long as a structure such as $X_2$ to $X_{10}$, $X_1$ to $X_{14}$, or one of the other exemplary structures is present, the remaining chemical structure is relatively less important. Of course, any structure outside of the core $X_2$ to $X_{10}$ structure, or the $X_1$ to $X_{14}$, structure, should not significantly interfere with thrombopoietic activity of the compound. For example, an N-terminal Met residue is envisioned as falling within this invention. Additionally, although many of the preferred compounds of the invention are tandem dimers in that they possess two TMP moieties, other compounds of this invention are tandem multimers of the TMPs, i.e., compounds of the following exemplary structures:

$TMP_1$-L-$TMP_2$-L-$TMP_3$;

$TMP_1$-L-$TMP_2$-L-$TMP_3$-L-$TMP_4$;

$TMP_1$-L-$TMP_2$-L-$TMP_3$-L-$TMP_4$-L-$TMP_5$;

wherein $TMP_1$, $TMP_2$, $TMP_3$, $TMP_4$, and $TMP_5$ can have the same or different structures, and wherein each TMP and L is defined as set forth herein, and the linkers are each optional. Preferably, the compounds of this invention will have from 2-5 TMP moieties, particularly preferably 2-3, and most preferably 2. The compounds of the first embodiment of this invention will preferably have less than about 60, more preferably less than about 40 amino acids in total (i.e., they will be peptides).

As noted above, the compounds of the first embodiment of this invention are preferably TMP dimers which are either bonded directly or are linked by a linker group. The monomeric TMP moieties are shown in the conventional orientation from N to C terminus reading from left to right. Accordingly, it can be seen that the inventive compounds are all oriented so that the C terminus of $TMP_1$ is attached either directly or through a linker to the N-terminus of $TMP_2$. This orientation is referred to as a tandem orientation, and the inventive compounds may be generally referred to as "tandem dimers". These compounds are referred to as dimers even if $TMP_1$ and $TMP_2$ are structurally distinct. That is, both homodimers and heterodimers are envisioned.

The "linker" group ("$L_1$") is optional. When it is present, it is not critical what its chemical structure is, since it serves primarily as a spacer. The linker should be chosen so as not to interfere with the biological activity of the final compound and also so that immunogenicity of the final compound is not significantly increased. The linker is preferably made up of amino acids linked together by peptide bonds. Thus, in preferred embodiments, the linker comprises $Y_n$, wherein Y is a naturally occurring amino acid or a stereoisomer thereof and "n" is any one of 1 through 20. The linker is therefore made up of from 1 to 20 amino acids linked by peptide bonds, wherein the amino acids are selected from the 20 naturally-occurring amino acids. In a more preferred embodiment, the 1 to 20 amino acids are selected from Gly, Ala, Pro, Asn, Gln, Cys, Lys. Even more preferably, the linker is made up of a majority of amino acids that are sterically un-hindered, such as Gly, Gly-Gly [(Gly)$_2$], Gly-Gly-Gly [(Gly)$_3$] . . . (Gly)$_{20}$, Ala, Gly-Ala, Ala-Gly, Ala-Ala, etc. Other specific examples of linkers are:

(Gly)$_3$Lys(Gly)$_4$; (SEQ ID NO: 6)

(Gly)$_3$AsnGlySer(Gly)$_2$ (SEQ ID NO: 7)

(this structure provides a site for glycosylation, when it is produced recombinantly in a mammalian cell system that is capable of glycosylating such sites);

(Gly)$_3$Cys(Gly)$_4$; (SEQ ID NO: 8)
and

GlyProAsnGly. (SEQ ID NO: 9)

To explain the above nomenclature, for example, (Gly)$_3$Lys (Gly)$_4$ means Gly-Gly-Gly-Lys-Gly-Gly-Gly-Gly. Combinations of Gly and Ala are also preferred.

Non-peptide linkers are also possible. For example, alkyl linkers such as —HN—(CH$_2$)$_s$—CO—, wherein s=2-20 could be used. These alkyl linkers may further be substituted by any non-sterically hindering group such as lower alkyl (e.g., C$_1$-C$_6$), lower acyl, halogen (e.g., Cl, Br), CN, NH$_2$, phenyl, etc.

Another type of non-peptide linker is a polyethylene glycol group, such as:

—HN—CH$_2$—CH$_2$—(O—CH$_2$—CH$_2$)$_n$—O—CH$_2$—CO— wherein n is such that the overall molecular weight of the linker ranges from approximately 101 to 5000, preferably 101 to 500.

In general, it has been discovered that a linker of a length of about 0-14 sub-units (e.g., amino acids) is preferred for the thrombopoietic compounds of the first embodiment of this invention.

The peptide linkers may be altered to form derivatives in the same manner as described above for the TMPs.

The compounds of this first group may further be linear or cyclic. By "cyclic" is meant that at least two separated, i.e., non-contiguous, portions of the molecule are linked to each other. For example, the amino and carboxy terminus of the ends of the molecule could be covalently linked to form a cyclic molecule. Alternatively, the molecule could contain two or more Cys residues (e.g., in the linker), which could cyclize via disulfide bond formation. It is further contemplated that more than one tandem peptide dimer can link to form a dimer of dimers. Thus, for example, a tandem dimer containing a Cys residue can form an intermolecular disulfide bond with a Cys of another such dimer. See, for example, the compound of SEQ ID NO: 20, below.

The compounds of the invention may also be covalently or noncovalently associated with a carrier molecule, such as a linear polymer (e.g., polyethylene glycol, polylysine, dextran, etc.), a branched-chain polymer (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published 28 Oct. 1993); a lipid; a cholesterol group (such as a steroid); or a carbohydrate or oligosaccharide. Other possible carriers include one or more water soluble polymer attachments such as polyoxyethylene glycol, or polypropylene glycol as described U.S. Pat. Nos: 4,640,835, 4,496,689, 4,301,144, 4,670,417, 4,791,192 and 4,179,337. Still other useful polymers known in the art include monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide copolymer, polyoxyethylated polyols (e.g., glycerol) and polyvinyl alcohol, as well as mixtures of these polymers.

A preferred such carrier is polyethylene glycol (PEG). The PEG group may be of any convenient molecular weight and may be straight chain or branched. The average molecular weight of the PEG will preferably range from about 2 kDa to about 100 kDa, more preferably from about 5 kDa to about 50 kDa, most preferably from about 5 kDa to about 10 kDa.

The PEG groups will generally be attached to the compounds of the invention via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group).

Carbohydrate (oligosaccharide) groups may conveniently be attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids not counting proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). However, such sites may further be glycosylated by synthetic or semi-synthetic procedures known in the art.

Some exemplary peptides of this invention are shown below. Single letter amino acid abbreviations are used, and the linker is shown separated by dashes for clarity. Additional abbreviations: BrAc means bromoacetyl (BrCH$_2$C(O)) and PEG is polyethylene glycol.

IEGPTLRQWLAARA-GPNG-IEGPTLRQWLAARA (SEQ ID NO: 10)

IEGPTLRQCLAARA-GGGGGGGG-IEGPTLRQCLAARA (cyclic) (SEQ ID NO: 11)
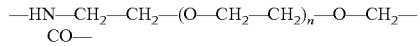

IEGPTLRQCLAARA-GGGGGGGG-IEGPTLRQCLAARA (linear) (SEQ ID NO: 12)

```
IEGPTLRQALAARA-GGGGGGGG-IEGPTLRQALAARA        (SEQ ID NO: 13)

IEGPTLRQWLAARA-GGGKGGGG-IEGPTLRQWLAARA        (SEQ ID NO: 14)

IEGPTLRQWLAARA-GGGK(BrAc)GGGG-IEGPTLRQWLAARA  (SEQ ID NO: 15)

IEGPTLRQWLAARA-GGGCGGGG-IEGPTLRQWLAARA        (SEQ ID NO: 16)

IEGPTLRQWLAARA-GGGK(PEG)GGGG-IEGPTLRQWLAARA   (SEQ ID NO: 17)

IEGPTLRQWLAARA-GGGC(PEG)GGGG-IEGPTLRQWLAARA   (SEQ ID NO: 18)

IEGPTLRQWLAARA-GGGNGSGG-IEGPTLRQWLAARA        (SEQ ID NO: 19)

IEGPTLRQWLAARA-GGGCGGGG-IEGPTLRQWLAARA
                  |
IEGPTLRQWLAARA-GGGCGGGG-IEGPTLRQWLAARA        (SEQ ID NO: 20)

IEGPTLRQWLAARA-GGGGGGGG-IEGPTLRQWLAARA        (SEQ ID NO: 21)
```

In each of the above compounds, an N-terminal Met (or M residue, using the one-letter code) is contemplated as well. Multimers (e.g., tandem and non-tandem, covalently bonded and non-covalently bonded) of the above compounds are also contemplated.

In a second embodiment of this invention, the compounds described above may further be fused to one or more Fc groups, either directly or through linker groups. In general, the formula of this second group of compounds is:

$$(Fc)_m\text{-}(L_2)_q\text{-}TMP_1\text{-}(L_1)_n\text{-}TMP_2\text{-}(L_3)_r\text{-}(Fc)_p$$

wherein $TMP_1$, $TMP_2$ and n are each as described above; $L_1$, $L_2$ and $L_3$ are linker groups which are each independently selected from the linker groups described above; Fc is an Fc region of an immunoglobulin; m, p, q and r are each independently selected from the group consisting of 0 and 1, wherein at least one of m or p is 1, and further wherein if m is 0 then q is 0, and if p is 0, then r is 0; and physiologically acceptable salts thereof.

Accordingly, the compounds of this second group have structures as defined for the first group of compounds as described above, but these compounds are further fused to at least one Fc group either directly or through one or more linker groups.

The Fc sequence of the above compounds may be selected from the human immunoglobulin IgG-1 heavy chain, see Ellison, J. W. et al., Nucleic Acids Res. 10:4071-4079 (1982), or any other Fc sequence known in the art (e.g. other IgG classes including but not limited to IgG-2, IgG-3 and IgG-4, or other immunoglobulins).

It is well known that Fc regions of antibodies are made up of monomeric polypeptide segments that may be linked into dimeric or multimeric forms by disulfide bonds or by non-covalent association. The number of intermolecular disulfide bonds between monomeric subunits of native Fc molecules ranges from 1 to 4 depending on the class (e.g., IgG, IgA, IgE) or subclass (e.g., IgG1, IgG2, IgG3, IgA1, IgA2) of antibody involved. The term "Fc" as used herein is generic to the monomeric, dimeric, and multimeric forms of Fc molecules. It should be noted that Fc monomers will spontaneously dimerize when the appropriate Cys residues are present unless particular conditions are present that prevent dimerization through disulfide bond formation. Even if the Cys residues that normally form disulfide bonds in the Fc dimer are removed or replaced by other residues, the monomeric chains will generally dimerize through non-covalent interactions. The term "Fc" herein is used to mean any of these forms: the native monomer, the native dimer (disulfide bond linked), modified dimers (disulfide and/or non-covalently linked), and modified monomers (i.e., derivatives).

Variants, analogs or derivatives of the Fc portion may be constructed by, for example, making various substitutions of residues or sequences.

Variant (or analog) polypeptides include insertion variants, wherein one or more amino acid residues supplement an Fc amino acid sequence. Insertions may be located at either or both termini of the protein, or may be positioned within internal regions of the Fc amino acid sequence. Insertional variants with additional residues at either or both termini can include for example, fusion proteins and proteins including amino acid tags or labels. For example, the Fc molecule may optionally contain an N-terminal Met, especially when the molecule is expressed recombinantly in a bacterial cell such as E. coli.

In Fc deletion variants, one or more amino acid residues in an Fc polypeptide are removed. Deletions can be effected at one or both termini of the Fc polypeptide, or with removal of one or more residues within the Fc amino acid sequence. Deletion variants, therefore, include all fragments of an Fc polypeptide sequence.

In Fc substitution variants, one or more amino acid residues of an Fc polypeptide are removed and replaced with alternative residues. In one aspect, the substitutions are conservative in nature, however, the invention embraces substitutions that ore also non-conservative.

For example, cysteine residues can be deleted or replaced with other amino acids to prevent formation of some or all disulfide crosslinks of the Fc sequences. In particular, the amino acids at positions 7 and 10 of SEQ ID NO:5 are cysteine residues. One may remove each of these cysteine residues or substitute one or more such cysteine residues with other amino acids, such as Ala or Ser. As another example, modifications may also be made to introduce amino acid substitutions to (1) ablate the Fc receptor binding site; (2) ablate the complement (Clq) binding site; and/or to (3) ablate the antibody dependent cell-mediated cytotoxicity (ADCC) site. Such sites are known in the art, and any known substitutions are within the scope of Fc as used herein. For example, see *Molecular Immunology*, Vol. 29, No. 5, 633-639 (1992) with regards to ADCC sites in IgG1.

Likewise, one or more tyrosine residues can be replaced by phenylalanine residues as well. In addition, other variant amino acid insertions, deletions (e.g., from 1-25 amino acids) and/or substitutions are also contemplated and are within the scope of the present invention. Conservative amino acid substitutions will generally be preferred. Furthermore, alterations may be in the form of altered amino acids, such as peptidomimetics or D-amino acids.

Fc sequences of the TMP compound may also be derivatized, i.e., bearing modifications other than insertion, deletion, or substitution of amino acid residues. Preferably, the modifications are covalent in nature, and include for example, chemical bonding with polymers, lipids, other organic, and inorganic moieties. Derivatives of the invention may be prepared to increase circulating half-life, or may be designed to improve targeting capacity for the polypeptide to desired cells, tissues, or organs.

It is also possible to use the salvage receptor binding domain of the intact Fc molecule as the Fc part of the inventive compounds, such as described in WO 96/32478, entitled "Altered Polypeptides with Increased Half-Life". Additional members of the class of molecules designated as Fc herein are those that are described in WO 97/34631, entitled "Immunoglobulin-Like Domains with Increased Half-Lives". Both of the published PCT applications cited in this paragraph are hereby incorporated by reference.

The Fc fusions may be at the N or C terminus of $TMP_1$ or $TMP_2$ or at both the N and C termini of the TMPs. It has been surprisingly discovered that peptides in which an Fc moiety is ligated to the N terminus of the TMP group is more bioactive than the other possibilities, so the fusion having an Fc domain at the N terminus of $TMP_1$ (i.e., r and p are both 0 and m and q are both 1 in general formula) is preferred. When the Fc chain is fused at the N-terminus of the TMP or linker, such fusion will generally occur at the C-terminus of the Fc chain, and vice versa.

Figure 6A:
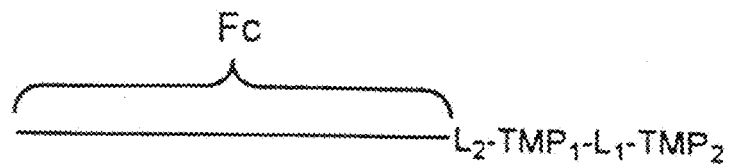
FIGS. 6A, 6B, and 6C show schematic diagrams of preferred compounds of the present invention.
Figure 6B:
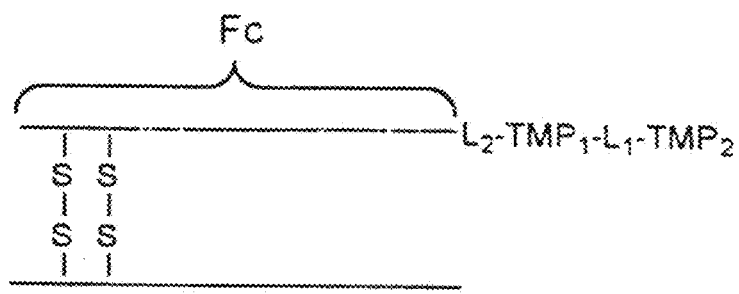
Figure 6C:
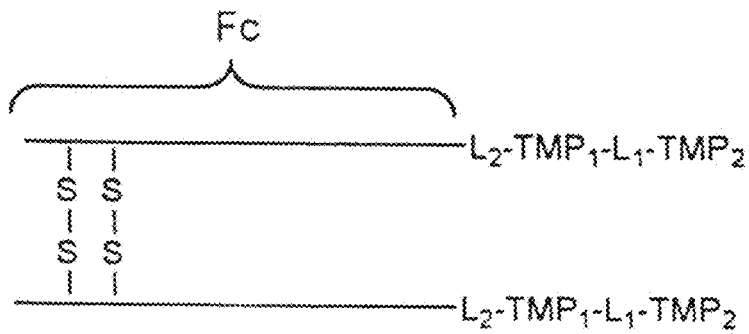

Also preferred are compounds that are dimers (e.g., tandem and non-tandem) of the compounds set forth in the general formula as set out above. In such cases, each Fc chain will be linked to a tandem dimer of TMP peptides. A schematic example of such a compound is shown in FIG. 6C. A preferred example of this type of compound is based on FIG. 6C, wherein Fc is a dimer of the compound of SEQ ID NO: 5, each $L_2$ is $(Gly)_5$, $TMP_1$ and $TMP_2$ are each the compound of SEQ ID NO: 1, and each $L_1$ is $(Gly)_8$. This compound is also referred to herein as "Fc-$TMP_1$-L-$TMP_2$". It is also represented as a dimer (through the Fc portion) of SEQ ID NO: 34.

The analogous compound wherein the Fc group is attached through a linker to the C-terminus of the $TMP_2$ groups in FIG. 6C is also contemplated and is referred to herein as $TMP_1$-L-$TMP_2$-Fc.

Some specific examples of compounds from the second group are provided as follows:

In each of the above compounds, an additional N-terminal Met (or M residue, using the one-letter code) is contemplated as well. The Met residue may be attached at the N-terminus of the Fc group in those cases wherein there is an Fc group attached to the N-terminus of the TMP. In those cases wherein the Fc group is attached at the C-terminus of the TMP, the Met residues could be attached to the N-terminus of the TMP group.

In each of the above cases Fc is preferably the Fc region of the human immunoglobulin IgG1 heavy chain or a biologically active fragment, derivative, or dimer thereof, see Ellison, J. W. et al., Nucleic Acids Res. 10:4071-4079 (1982). The Fc sequence shown in SEQ ID NO: 5 is the most preferred Fc for the above compounds. Also preferred are the above compounds in which the Fc is a dimeric form of the sequence of SEQ ID NO: 5 and each Fc chain is attached to a TMP tandem dimer.

Additionally, although many of the preferred compounds of the second embodiment include one or more tandem dimers in that they possess two linked TMP moieties, other compounds of this invention include tandem multimers of the TMPs, i.e., compounds of the following exemplary structures:

Fc-$TMP_1$-L-$TMP_2$-L-$TMP_3$;

Fc-$TMP_1$-L-$TMP_2$-L-$TMP_3$-L-$TMP_4$;

Fc-$TMP_1$-L-$TMP_2$-L-$TMP_3$-L-$TMP_4$-L-$TMP_5$;

$TMP_1$-L-$TMP_2$-L-$TMP_3$-L-Fc;

$TMP_1$-L-$TMP_2$-L-$TMP_3$-L-$TMP_4$-L-Fc;

$TMP_1$-L-$TMP_2$-L-$TMP_3$-L-$TMP_4$-L-$TMP_{\_5}$-L-Fc;

wherein $TMP_1$, $TMP_2$, $TMP_3$, $TMP_4$, and $TMP_5$ can have the same or different structures, and wherein Fc and each TMP and L is defined as set forth above, and the linkers are each optional. In each case above, the Fc group can be monomeric or dimeric, and in cases where the Fc is dimeric, one or more TMP multimer can be attached to each Fc chains. Also contemplated are other examples wherein the TMP dimers or multimers are attached to both the N and C-termini of one or both Fc chains, including the case wherein TMP dimers or multimers are attached to all four termini of two Fc chains.

```
Fc-IEGPTLRQWLAARA-GPNG-IEGPTLRQWLAARA              (SEQ ID NO: 22)

Fc-IEGPTLRQWLAARA-GPNG-IEGPTLRQWLAARA-Fc           (SEQ ID NO: 23)

IEGPTLRQWLAARA-GGGGGGGG-IEGPTLRQWLAARA-Fc          (SEQ ID NO: 24)
Fc-GG-IEGPTLRQWLAARA-GPNG-IEGPTLRQWLAARA           (SEQ ID NO: 25)

Fc-IEGPTLRQWLAARA-GGGGGGGG-IEGPTLRQWLAARA          (SEQ ID NO: 26)

Fc-IEGPTLRQCLAARA-GGGGGGGG-IEGPTLRQCLAARA (cyclic) (SEQ ID NO: 27)
              |_____|

Fc-IEGPTLRQCLAARA-GGGGGGGG-IEGPTLRQCLAARA (linear) (SEQ ID NO: 28)

Fc-IEGPTLRQALAARA-GGGGGGGG-IEGPTLRQALAARA          (SEQ ID NO: 29)

Fc-IEGPTLRQWLAARA-GGGKGGGG-IEGPTLRQWLAARA          (SEQ ID NO: 30)
Fc-IEGPTLRQWLAARA-GGGCGGGG-IEGPTLRQWLAARA          (SEQ ID NO: 31)

Fc-IEGPTLRQWLAARA-GGGNGSGG-IEGPTLRQWLAARA          (SEQ ID NO: 32)
Fc-IEGPTLRQWLAARA-GGGCGGGG-IEGPTLRQWLAARA
                        |
Fc-IEGPTLRQWLAARA-GGGCGGGG-IEGPTLRQWLAARA          (SEQ ID NO: 33)

Fc-GGGGG-IEGPTLRQWLAARA-GGGGGGGG-IEGPTLRQWLAARA    (SEQ ID NO: 34)
```

Preferably, the compounds of this second embodiment of the invention will have from about 200 to 400 amino acids in total (i.e., they will be polypeptides).

Methods of Making

The compounds of this invention may be made in a variety of ways. Since many of the compounds will be peptides, or will include a peptide, methods for synthesizing peptides are of particular relevance here. For example, solid phase synthesis techniques may be used. Suitable techniques are well known in the art, and include those described in Merrifield, in Chem. Polypeptides, pp. 335-61 (Katsoyannis and Panayotis eds. 1973); Merrifield, J. Am. Chem. Soc. 85:2149 (1963); Davis et al., Biochem. Intl. 10:394-414 (1985); Stewart and Young, Solid Phase Peptide Synthesis (1969); U.S. Pat. No. 3,941,763; Finn et al., The Proteins, 3rd ed., vol. 2, pp. 105-253 (1976); and Erickson et al., The Proteins, 3rd ed., vol. 2, pp. 257-527 (1976). Solid phase synthesis is the preferred technique of making individual peptides since it is the most cost-effective method of making small peptides.

The peptides may also be made in transformed host cells using recombinant DNA techniques. To do so, a recombinant DNA molecule coding for the peptide is prepared. Methods of preparing such DNA and/or RNA molecules are well known in the art. For instance, sequences coding for the peptides could be excised from DNA using suitable restriction enzymes. The relevant sequences can be created using the polymerase chain reaction (PCR) with the inclusion of useful restriction sites for subsequent cloning. Alternatively, the DNA/RNA molecule could be synthesized using chemical synthesis techniques, such as the phosphoramidite method. Also, a combination of these techniques could be used.

The invention also includes a vector encoding the peptides in an appropriate host. The vector comprises the DNA molecule that encodes the peptides operatively linked to appropriate expression control sequences. Methods of effecting this operative linking, either before or after the peptide-encoding DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

The resulting vector comprising the peptide-encoding DNA molecule is used to transform an appropriate host. This transformation may be performed using methods well known in the art.

Any of a large number of available and well-known host cells may be used in the practice of this invention. The selection of a particular host is dependent upon a number of factors recognized by the art. These factors include, for example, compatibility with the chosen expression vector, toxicity to the host cell of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence.

Within these general guidelines, useful microbial hosts include bacteria (such as *E. coli*), yeast (such as *Saccharomyces* sp. and *Pichia pastoris*) and other fungi, insects, plants, mammalian (including human) cells in culture, or other hosts known in the art.

Next, the transformed host is cultured under conventional fermentation conditions so that the desired peptides are expressed. Such fermentation conditions are well known in the art.

Finally, the peptides are purified from the fermentation culture or from the host cells in which they are expressed. These purification methods are also well known in the art.

Compounds that contain derivatized peptides or which contain non-peptide groups may be synthesized by well-known organic chemistry techniques.

Uses of the Compounds

The compounds of this invention have the ability to bind to and activate the c-Mpl receptor, and/or have the ability to stimulate the production (both in vivo and in vitro) of platelets ("thrombopoietic activity") and platelet precursors ("megakaryocytopoietic activity"). To measure the activity (-ies) of these compounds, one can utilize standard assays, such as those described in WO95/26746 entitled "Compositions and Methods for Stimulating Megakaryocyte Growth and Differentiation". In vivo assays are further described in the Examples section herein.

The conditions to be treated by the methods and compositions of the present invention are generally those which involve an existing megakaryocyte/platelet deficiency or an expected or anticipated megakaryocyte/platelet deficiency in the future (e.g., because of planned surgery or platelet donation). Such conditions may be the result of a deficiency (temporary or permanent) of active Mpl ligand in vivo. The generic term for platelet deficiency is thrombocytopenia, and hence the methods and compositions of the present invention are generally available for prophylactically or therapeutically treating thrombocytopenia in patients in need thereof.

The World Health Organization has classified the degree of thrombocytopenia on the number of circulating platelets in the individual (Miller, et al., Cancer 47:210-211 (1981)). For example, an individual showing no signs of thrombocytopenia (Grade 0) will generally have at least 100,000 platelets/$mm^3$. Mild thrombocytopenia (Grade 1) indicates a circulating level of platelets between 79,000 and 99,000/$mm^3$. Moderate thrombocytopenia (Grade 2) shows between 50,000 and 74,000 platelets/$mm^3$ and severe thrombocytopenia is characterized by between 25,000 and 49,000 platelets/$mm^3$. Life-threatening or debilitating thrombocytopenia is characterized by a circulating concentration of platelets of less than 25,000/$mm^3$.

Thrombocytopenia (platelet deficiencies) may be present for various reasons, including chemotherapy and other therapy with a variety of drugs, radiation therapy, surgery, accidental blood loss, and other specific disease conditions. Exemplary specific disease conditions that involve thrombocytopenia and may be treated in accordance with this invention are: aplastic anemia; idiopathic or immune thrombocytopenia (ITP), including idiopathic thrombocytopenic purpura associated with breast cancer; HIV associated ITP and HIV-related thrombotic thrombocytopenic purpura; metastatic tumors which result in thrombocytopenia; systemic lupus erythematosus; including neonatal lupus syndrome splenomegaly; Fanconi's syndrome; vitamin B12 deficiency; folic acid deficiency; May-Hegglin anomaly; Wiskott-Aldrich syndrome; chronic liver disease; myelodysplastic syndrome associated with thrombocytopenia; paroxysmal nocturnal hemoglobinuria; acute profound thrombocytopenia following C7E3 Fab (Abciximab) therapy; alloimmune thrombocytopenia, including maternal alloimmune thrombocytopenia; thrombocytopenia associated with antiphospholipid antibodies and thrombosis; autoimmune thrombocytopenia; drug-induced immune thrombocytopenia, including carboplatin-induced thrombocytopenia, heparin-induced thrombocytopenia; fetal thrombocytopenia; gestational thrombocytopenia; Hughes' syndrome; lupoid thrombocytopenia; accidental and/or massive blood loss;

myeloproliferative disorders; thrombocytopenia in patients with malignancies; thrombotic thrombocytopenia purpura, including thrombotic microangiopathy manifesting as thrombotic thrombocytopenic purpura/hemolytic uremic syndrome in cancer patients; autoimmune hemolytic anemia; occult jejunal diverticulum perforation; pure red cell aplasia; autoimmune thrombocytopenia; nephropathia epidemica; rifampicin-associated acute renal failure; Paris-Trousseau thrombocytopenia; neonatal alloimmune thrombocytopenia; paroxysmal nocturnal hemoglobinuria; hematologic changes in stomach cancer; hemolytic uremic syndromes in childhood; hematologic manifestations related to viral infection including hepatitis A virus and CMV-associated thrombocytopenia. Also, certain treatments for AIDS result in thrombocytopenia (e.g., AZT). Certain wound healing disorders might also benefit from an increase in platelet numbers.

With regard to anticipated platelet deficiencies, e.g., due to future surgery, a compound of the present invention could be administered several days to several hours prior to the need for platelets. With regard to acute situations, e.g., accidental and massive blood loss, a compound of this invention could be administered along with blood or purified platelets.

The compounds of this invention may also be useful in stimulating certain cell types other than megakaryocytes if such cells are found to express Mpl receptor. Conditions associated with such cells that express the Mpl receptor, which are responsive to stimulation by the Mpl ligand, are also within the scope of this invention.

The compounds of this invention may be used in any situation in which production of platelets or platelet precursor cells is desired, or in which stimulation of the c-Mpl receptor is desired. Thus, for example, the compounds of this invention may be used to treat any condition in a mammal wherein there is a need of platelets, megakaryocytes, and the like. Such conditions are described in detail in the following exemplary sources: WO95/26746; WO95/21919; WO95/18858; WO95/21920 and are incorporated herein.

The compounds of this invention may also be useful in maintaining the viability or storage life of platelets and/or megakaryocytes and related cells. Accordingly, it could be useful to include an effective amount of one or more such compounds in a composition containing such cells.

By "mammal" is meant any mammal, including humans, domestic animals including dogs and cats; exotic and/or zoo animals including monkeys; laboratory animals including mice, rats, and guinea pigs; farm animals including horses, cattle, sheep, goats, and pigs; and the like. The preferred mammal is human.

Pharmaceutical Compositions

The present invention also provides methods of using pharmaceutical compositions of the inventive compounds. Such pharmaceutical compositions may be for administration for injection, or for oral, nasal, transdermal or other forms of administration, including, e.g., by intravenous, intradermal, intramuscular, intramammary, intraperitoneal, intrathecal, intraocular, retrobulbar, intrapulmonary (e.g., aerosolized drugs) or subcutaneous injection (including depot administration for long term release); by sublingual, anal, vaginal, or by surgical implantation, e.g., embedded under the splenic capsule, brain, or in the cornea. The treatment may consist of a single dose or a plurality of doses over a period of time. In general, comprehended by the invention are pharmaceutical compositions comprising effective amounts of a compound of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used, and this may have the effect of promoting sustained duration in the circulation. The pharmaceutical compositions optionally may include still other pharmaceutically acceptable liquid, semisolid, or solid diluents that serve as pharmaceutical vehicles, excipients, or media, including but are not limited to, polyoxyethylene sorbitan monolaurate, magnesium stearate, methyl- and propylhydroxybenzoate, starches, sucrose, dextrose, gum acacia, calcium phosphate, mineral oil, cocoa butter, and oil of theobroma. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder, such as lyophilized form. Implantable sustained release formulations are also contemplated, as are transdermal formulations.

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K., Modern Pharmaceutics, Edited by G. S. Banker and C. T. Rhodes Chapter 10, 1979, herein incorporated by reference. In general, the formulation will include the inventive compound, and inert ingredients which allow for protection against the stomach environment, and release of the biologically active material in the intestine.

Also specifically contemplated are oral dosage forms of the above inventive compounds. If necessary, the compounds may be chemically modified so that oral delivery is efficacious. Generally, the chemical modification contemplated is the attachment of at least one moiety to the compound molecule itself, where said moiety permits (a) inhibition of proteolysis; and (b) uptake into the blood stream from the stomach or intestine. Also desired is the increase in overall stability of the compound and increase in circulation time in the body. Examples of such moieties include: Polyethylene glycol, copolymers of ethylene glycol and propylene glycol, carboxymethyl cellulose, dextran, polyvinyl alcohol, polyvinyl pyrrolidone and polyproline (Abuchowski and Davis, Soluble Polymer-Enzyme Adducts, Enzymes as Drugs, Hocenberg and Roberts, eds., Wiley-Interscience, New York, N.Y., (1981), pp 367-383; Newmark, et al., J. Appl. Biochem. 4:185-189 (1982)). Other polymers that could be used are poly-1,3-dioxolane and poly-1,3,6-tioxocane. Preferred for pharmaceutical usage, as indicated above, are polyethylene glycol moieties.

For the oral delivery dosage forms, it is also possible to use a salt of a modified aliphatic amino acid, such as sodium N-(8-[2-hydroxybenzoyl]amino)caprylate (SNAC), as a carrier to enhance absorption of the therapeutic compounds of this invention. The clinical efficacy of a heparin formulation using SNAC has been demonstrated in a Phase II trial conducted by Emisphere Technologies. See U.S. Pat. No. 5,792,451, "Oral drug delivery composition and methods".

The therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment, a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethonium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the compound are for instance the fatty acids oleic acid, linoleic acid and linolenic acid.

Controlled release formulation may be desirable. The drug could be incorporated into an inert matrix which permits release by either diffusion or leaching mechanisms e.g., gums. Slowly degenerating matrices may also be incorporated into the formulation, e.g., alginates, polysaccharides. Another form of a controlled release of this therapeutic is by a method based on the Oros therapeutic system (Alza Corp.), i.e., the drug is enclosed in a semipermeable membrane which allows water to enter and push drug out through a single small opening due to osmotic effects. Some enteric coatings also have a delayed release effect.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Also contemplated herein is pulmonary delivery of the present protein (or derivatives thereof). The protein (or derivative) is delivered to the lungs of a mammal while inhaling and traverses across the lung epithelial lining to the blood stream. (Other reports of this include Adjei et al., Pharmaceutical Research 7:565-569 (1990); Adjei et al., International Journal of Pharmaceutics 63:135-144 (1990)(leuprolide acetate); Braquet et al., Journal of Cardiovascular Pharmacology 13 (suppl.5): s.143-146 (1989)(endothelin-1); Hubbard et al., Annals of Internal Medicine 3:206-212 (1989)(α1-antitrypsin); Smith et al., J. Clin. Invest. 84:1145-1146 (1989) (α1-proteinase); Oswein et al., "Aerosolization of Proteins", Proceedings of Symposium on Respiratory Drug Delivery II, Keystone, Colo., March, 1990 (recombinant human growth hormone); Debs et al., The Journal of Immunology 140:3482-3488 (1988)(interferon-γ and tumor necrosis factor α) and Platz et al., U.S. Pat. No. 5,284,656 (granulocyte colony stimulating factor).

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the inventive compound. Typically, each formulation is specific to the type of device employed and may involve the use of an appropriate propellant material, in addition to diluents, adjuvants and/or carriers useful in therapy.

The inventive compound should most advantageously be prepared in particulate form with an average particle size of less than 10μm (or microns), most preferably 0.5 to 5μm, for most effective delivery to the distal lung.

Carriers include carbohydrates such as trehalose, mannitol, xylitol, sucrose, lactose, and sorbitol. Other ingredients for use in formulations may include DPPC, DOPE, DSPC and DOPC. Natural or synthetic surfactants may be used. Polyethylene glycol may be used (even apart from its use in derivatizing the protein or analog). Dextrans, such as cyclodextran, may be used. Bile salts and other related enhancers may be used. Cellulose and cellulose derivatives may be used. Amino acids may be used, such as use in a buffer formulation.

Also, the use of liposomes, microcapsules or microspheres, inclusion complexes, or other types of carriers is contemplated.

Formulations suitable for use with a nebulizer, either jet or ultrasonic, will typically comprise the inventive compound dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the inventive compound suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the inventive compound and may also include a bulking agent, such as lactose, sorbitol, sucrose, mannitol, trehalose, or xylitol in amounts which facilitate dispersal of the powder from the device, e.g., 50 to 90% by weight of the formulation.

Nasal delivery of the inventive compound is also contemplated. Nasal delivery allows the passage of the protein to the blood stream directly after administering the therapeutic product to the nose, without the necessity for deposition of the product in the lung. Formulations for nasal delivery include those with dextran or cyclodextran. Delivery via transport across other mucous membranes is also contemplated.

Dosages

The dosage regimen involved in a method for treating the above-described conditions will be determined by the attending physician, considering various factors which modify the action of drugs, e.g. the age, condition, body weight, sex and diet of the patient, the severity of any infection, time of administration and other clinical factors. Generally, the dose should be in the range of 0.1 μg to 100 mg of the inventive compound per kilogram of body weight per day, preferably 0.1 to 1000 μg/kg; and more preferably 0.1 to 150 μg/kg, given in daily doses or in equivalent doses at longer or shorter intervals, e.g., every other day, twice weekly, weekly, or twice or three times daily.

The inventive compound may be administered by an initial bolus followed by a continuous infusion to maintain therapeutic circulating levels of drug product. As another example, the inventive compound may be administered as a one-time dose. Those of ordinary skill in the art will readily optimize effective dosages and administration regimens as determined by good medical practice and the clinical condition of the individual patient. The frequency of dosing will depend on the pharmacokinetic parameters of the agents and the route of administration. The optimal pharmaceutical formulation will be determined by one skilled in the art depending upon the route of administration and desired dosage. See for example, Remington's Pharmaceutical Sciences, 18th Ed. (1990, Mack Publishing Co., Easton, Pa. 18042) pages 1435-1712, the disclosure of which is hereby incorporated by reference. Such formulations may influence the physical state, stability, rate of in vivo release, and rate of in vivo clearance of the administered agents. Depending on the route of administration, a suitable dose may be calculated according to body weight, body surface area or organ size. Further refinement of the calculations necessary to determine the appropriate dosage for treatment involving each of the above mentioned formulations is routinely made by those of ordinary skill in the art without undue experimentation, especially in light of the dosage information and assays disclosed herein, as well as the pharmacokinetic data observed in the human clinical trials discussed above. Appropriate dosages may be ascertained through use of established assays for determining blood levels dosages in conjunction with appropriate dose-response data. The final dosage regimen will be determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. As studies are conducted, further information will emerge regarding the appropriate dosage levels and duration of treatment for various diseases and conditions.

The therapeutic methods, compositions and compounds of the present invention may also be employed, alone or in combination with other cytokines, soluble Mpl receptor, hematopoietic factors, interleukins, growth factors or antibodies in the treatment of disease states characterized by other symptoms as well as platelet deficiencies. It is anticipated that the inventive compound will prove useful in treating some forms of thrombocytopenia in combination with general stimulators of hematopoiesis, such as IL-3 or GM-CSF. Other megakaryocytic stimulatory factors, i.e., meg-CSF, stem cell factor (SCF), leukemia inhibitory factor (LIF), oncostatin M (OSM), or other molecules with megakaryocyte stimulating activity may also be employed with Mpl ligand. Additional exemplary cytokines or hematopoietic factors for such co-administration include IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IL-7, IL-8, IL-9, IL-10, IL-12, IL-13, IL-14, IL-15, IL-16, IL-17, IL-18, thrombopoietin (TPO), angiopoietins, for example Ang-1, Ang-2, Ang-4, Ang-Y, the human angiopoietin-like polypeptide, vascular endothelial growth factor (VEGF), angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor α, cytokine-induced neutrophil chemotactic factor 1, cytokine-induced neutrophil, chemotactic factor 2 α, cytokine-induced neutrophil chemotactic factor 2 β, β endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor α 1, glial cell line-derived neutrophic factor receptor α 2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor a, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor receptor, TNF, including TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, vascular endothelial growth factor, and chimeric proteins and biologically or immunologically active fragments thereof. It may further be useful to administer, either simultaneously or sequentially, an effective amount of a soluble mammalian Mpl receptor, which appears to have an effect of causing megakaryocytes to fragment into platelets once the megakaryocytes have reached mature form. Thus, administration of an inventive compound (to enhance the number of mature megakaryocytes) followed by administration of the soluble Mpl receptor (to inactivate the ligand and allow the mature megakaryocytes to produce platelets) is expected to be a particularly effective means of stimulating platelet production. The dosage recited above would be adjusted to compensate for such additional components in the therapeutic composition. Progress of the treated patient can be monitored by conventional methods.

In cases where the inventive compounds are added to compositions of platelets and/or megakaryocytes and related cells, the amount to be included will generally be ascertained experimentally by techniques and assays known in the art. An exemplary range of amounts is 0.1 µg-1 mg inventive compound per $10^6$ cells.

It is understood that the application of the teachings of the present invention to a specific problem or situation will be within the capabilities of one having ordinary skill in the art in light of the teachings contained herein. Examples of the products of the present invention and representative processes for their isolation, use, and manufacture appear below.

EXAMPLES

I. The following sets forth exemplary methods for making some of the compounds of the first group disclosed herein.

A. Materials and Methods

Figure 3:
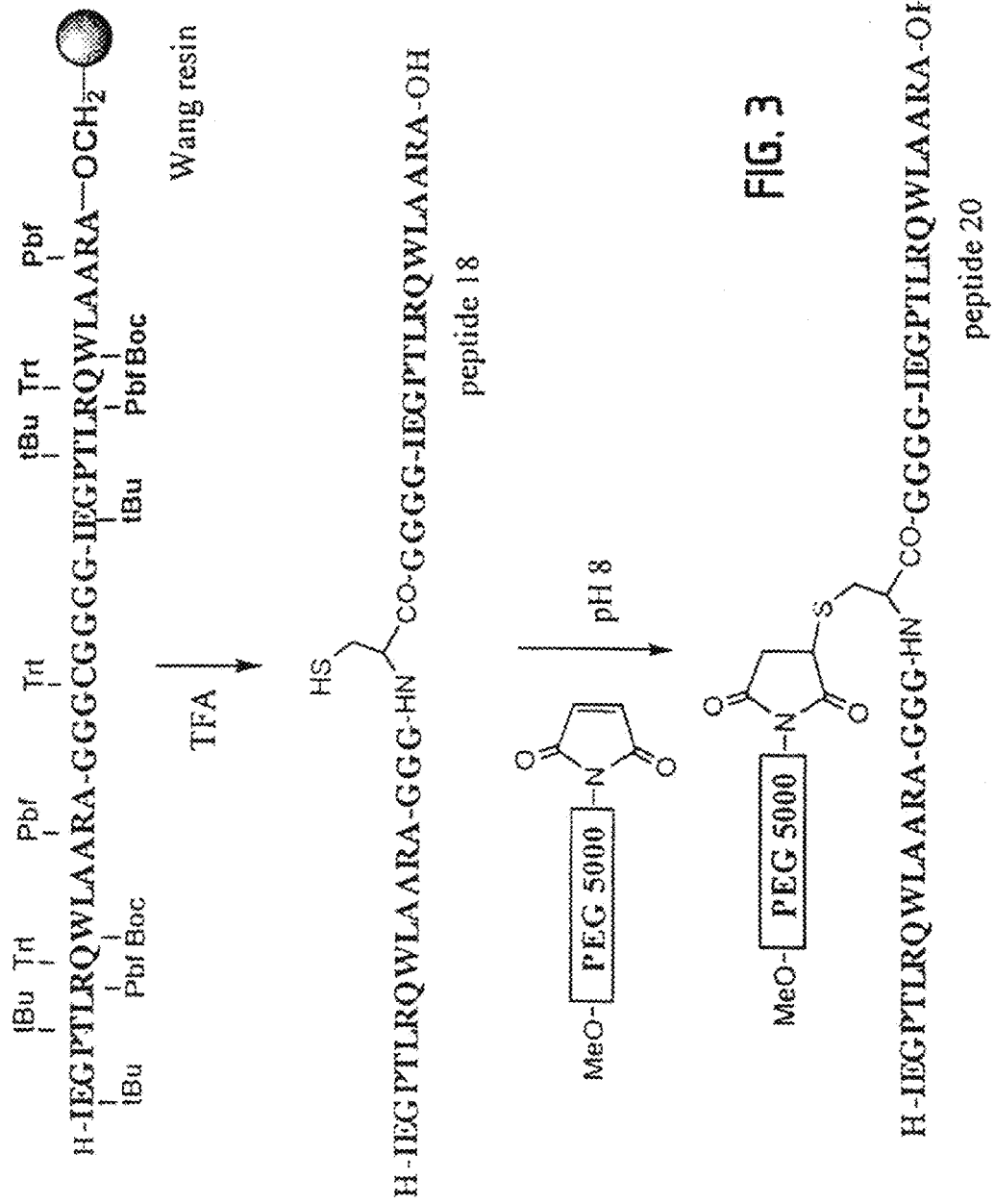
FIG. 3 shows a synthetic scheme for the preparation of pegylated peptide 20 (SEQ ID NO:18).

All amino acid derivatives (all of L-configurations) and resins used in peptide synthesis were purchased from Novabiochem. Peptide synthesis reagents (DCC, HOBt, etc.) were purchased in the solution forms from Applied Biosystems, Inc. The two PEG derivatives were from Shearwater Polymers, Inc. All solvents (dichloromethane, N-methylpyrrolidinone, methanol, acetonitrile) were from EM Sciences. Analytical HPLC was run on a Beckman system with a Vydac column (0.46 cm×25 cm, C18 reversed phase, 5 mm), at a flow rate of 1 ml/min and with dual UV detection at 220 and 280 nm. Linear gradients were used for all HPLC operations with two mobile phases: Buffer A—$H_2O$ (0.1% TFA) and Buffer B—acetonitrile (0.1% TFA). The numbered peptides referred to herein, e.g., 17b, 18, 19, and 20, are numbered in reference to Table 1, and some of them are further illustrated in FIGS. 2 and 3.

Peptide synthesis. All peptides were prepared by the well established stepwise solid phase synthesis method. Solid-phase synthesis with Fmoc chemistry was carried out using an ABI Peptide Synthesizer. Typically, peptide synthesis began with a preloaded Wang resin on a 0.1 mmol scale. Fmoc deprotection was carried out with the standard piperidine protocol. The coupling was effected using DCC/HOBt. Side-chain protecting groups were: Glu(O-t-Bu), Thr(t-Bu), Arg (Pbf), Gln(Trt), Trp(t-Boc) and Cys(Trt). For the first peptide precursor for pegylation, Dde was used for side chain protection of the Lys on the linker and Boc-Ile-OH was used for the last coupling. Dde was removed by using anhydrous hydrazine (2% in NMP, 3×2min), followed by coupling with bromoacetic anhydride preformed by the action of DCC. For peptide 18, the cysteine side chain in the linker was protected by a trityl group. The final deprotection and cleavage of all peptidyl-resins was effected at RT for 4 hr, using trifluoroacetic acid (TFA) containing 2.5% $H_2O$, 5% phenol, 2.5% triisopropylsilane and 2.5% thioanisole. After removal of TFA, the cleaved peptide was precipitated with cold anhydrous ether. Disulfide formation of the cyclic peptide was performed directly on the crude material by using 15% DMSO in $H_2O$ (pH 7.5). All crude peptides were purified by preparative reverse phase HPLC and the structures were confirmed by ESI-MS and amino acid analysis.

Alternatively, all peptides described above could also be prepared by using the t-Boc chemistry. In this case, the starting resins would be the classic Merrifield or Pam resin, and side chain protecting groups would be: Glu(OBzl), Thr(Bzl), Arg(Tos), Trp(CHO), Cys(p-MeBzl). Hydrogen fluoride (HF) would be used for the final cleavage of the peptidyl resins.

All the tandem dimeric peptides described in this study that have linkers composed of natural amino acids can also be prepared by recombinant DNA technology.

PEGylation. A novel, convergent strategy for the pegylation of synthetic peptides was developed which consists of combining, through forming a conjugate linkage in solution, a peptide and a PEG moiety, each bearing a special functionality that is mutually reactive toward the other. The precursor peptides can be easily prepared with the conventional solid phase synthesis as described above. As described below, these peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The pegylated peptides can be easily purified by preparative HPLC and characterized by analytical HPLC, amino acid analysis and laser desorption mass spectrometry.

Preparation of peptide 19. Peptide 17b (12 mg) and MeO-PEG-SH 5000 (30 mg, 2 equiv.) were dissolved in 1 ml aqueous buffer (pH 8). The mixture was incubated at RT for about 30 min and the reaction was checked by analytical HPLC which showed a >80% completion of the reaction. The pegylated material was isolated by preparative HPLC.

Preparation of peptide 20. Peptide 18 (14 mg) and MeO-PEG-maleimide (25 mg) were dissolved in about 1.5 ml aqueous buffer (pH 8). The mixture was incubated at RT for about 30 min, at which time ~70% transformation was complete as monitored with analytical HPLC by applying an aliquot of sample to the HPLC column. The pegylated material was purified by preparative HPLC.

Bioactivity assay. The TPO in vitro bioassay is a mitogenic assay utilizing an IL-3 dependent clone of murine 32D cells that have been transfected with human mpl receptor. This assay is described in greater detail in WO 95/26746. Cells are maintained in MEM medium containing 10% Fetal Clone II and 1 ng/ml mIL-3. Prior to sample addition, cells are prepared by rinsing twice with growth medium lacking mIL-3. An extended twelve point TPO standard curve is prepared, ranging from 3333 to 39 pg/ml. Four dilutions, estimated to fall within the linear portion of the standard curve, (1000 to 125 pg/ml), are prepared for each sample and run in triplicate. A volume of 100 µl of each dilution of sample or standard is added to appropriate wells of a 96 well microtiter plate containing 10,000 cells/well. After forty-four hours at 37° C. and 10% $CO_2$, MTS (a tetrazolium compound which is bioreduced by cells to a formazan) is added to each well. Approximately six hours later, the optical density is read on a plate reader at 490 nm. A dose response curve (log TPO concentration vs. O.D.-Background) is generated and linear regression analysis of points which fall in the linear portion of the standard curve is performed. Concentrations of unknown test samples are determined using the resulting linear equation and a correction for the dilution factor.

Abbreviations. HPLC: high performance liquid chromatography; ESI-MS: Electron spray ionization mass spectrometry; MALDI-MS: Matrix-assisted laser desorption ionization mass spectrometry; PEG: Poly(ethylene glycol). All amino acids are represented in the standard three-letter or single-letter codes. t-Boc: tert-Butoxycarbonyl; tBu: tert-Butyl; Bzl: Benzyl; DCC: Dicylcohexylcarbodiimide; HOBt: 1-Hydroxybenzotriazole; NMP: N-methyl-2-pyrrolidinone; Pbf: 2,2,4,6,7-pendamethyldihydro-benzofuran-5-sulfonyl; Trt: trityl; Dde: 1-(4,4-dimethyl-2,6-dioxo-cyclohexylidene) ethyl.

B. Results

TMP tandem dimers with polyglycine linkers. The design of sequentially linked TMP dimers was based on the assumption that a dimeric form of TMP was required for its effective interaction with c-Mpl (the TPO receptor) and that depending on how they were wound up against each other in the receptor context, the two TMP molecules could be tethered together in the C- to N-terminus configuration in a way that would not perturb the global dimeric conformation. Clearly, the activity of the tandem linked dimers may also depend on proper selection of the length and composition of the linker that joins the C- and -termini of the two sequentially aligned TMP monomers. Since no structural information of the TMP bound to c-Mpl was available, a series of dimeric peptides with linkers composed of 0 to 10 and 14 glycine residues (Table 1) were synthesized. Glycine was chosen because of its simplicity and flexibility. It was reasoned that a flexible polyglycine peptide chain might allow for the free folding of the two tethered TMP repeats into the required conformation, while more sterically hindered amino acid sequences may adopt undesired secondary structures whose rigidity might disrupt the correct packing of the dimeric peptide in the receptor context.

The resulting peptides are readily accessible by conventional solid phase peptide synthesis methods (Merrifiled, R. B., Journal of the American Chemical Society 85:2149 (1963)) with either Fmoc or t-Boc chemistry. Unlike the synthesis of the C-terminally linked parallel dimer (SEQ ID NO: 2) which required the use of an orthogonally protected lysine residue as the initial branch point to build the two peptide chains in a pseudosymmetrical way (Cwirla, S. E. et al., Science 276:1696-1699 (1997)), the synthesis of our tandem dimers was a straightforward, stepwise assembly of the continuous peptide chains from the C- to N-terminus. Since dimerization of TMP had a more dramatic effect on the proliferative activity than binding affinity as shown for the C-terminal dimer (Cwirla, S. E. et al., Science 276:1696-1699 (1997)), the synthetic peptides were tested directly for biological activity in a TPO-dependent cell-proliferation assay using an IL-3 dependent clone of murine 32D cells transfected with the full-length c-Mpl (Palacios, R. et al., Cell 41:727 (1985)). As the test results showed (see Table 1 below), all of the polyglycine linked tandem dimers demonstrated >1000 fold increases in potency as compared to the monomer, and were even more potent than the C-terminal dimer in this cell proliferation assay. The absolute activity of the C-terminal dimer in our assay was lower than that of the native TPO protein, which is different from the previously reported findings in which the C-terminal dimer was found to be as active as the natural ligand (Cwirla, S. E. et al., Science 276:1696-1699 (1997)). This might be due to differences in the conditions used in the two assays. Nevertheless, the difference in activity between tandem dimers© terminal of first monomer linked to N terminal of second monomer) and parallel dimers© terminal of first monomer linked to C terminal of second monomer) in the same assay clearly demonstrated the superiority of tandem dimerized product compared to parallel dimer products. It is interesting to note that a wide range of length is tolerated by the linker. The optimal linker with the selected TMP monomers (SEQ ID NO: 1) apparently is composed of 8 glycines.

Other tandem dimers. Subsequent to this first series of TMP tandem dimers, several other molecules were designed either with different linkers or containing modifications within the monomer itself. The first of these molecules, peptide 13, has a linker composed of GPNG, a sequence known to have a high propensity to form a β-turn-type secondary structure. Although still about 100-fold more potent than the monomer, this peptide was found to be >10-fold less active than the GGGG-linked analog. Thus, introduction of a relatively rigid β-turn at the linker region seemed to cause a slight distortion of the optimal agonist conformation in this short linker form.

The Trp9 in the TMP sequence is a highly conserved residue among the active peptides isolated from random peptide libraries. There is also a highly conserved Trp in the consensus sequences of EPO mimetic peptides and this Trp residue was found to be involved in the formation of a hydrophobic core between the two EPO Mimetic Peptides (EMPs) and contributed to hydrophobic interactions with the EPO receptor (Livnah, O. et al., Science 273:464-471 (1996)). By analogy, it was thought that the Trp9 residue in TMP might have a similar function in dimerization of the peptide ligand, and in an attempt to modulate and estimate the effects of noncovalent hydrophobic forces exerted by the two indole rings, several analogs were constructed resulting from mutations at the Trp. So in peptide 14, the Trp residue in each of the two TMP monomers was replaced with a Cys, and an intramolecular disulfide bond was formed between the two cysteines by oxidation which was envisioned to mimic the hydrophobic interactions between the two Trp residues in peptide dimerization. Peptide 15 is the reduced form of peptide 14. In peptide 16, the two Trp residues were replaced by Ala. As the assay data show, all three analogs were inactive. These data further demonstrated that Trp is important for the activity of the TPO mimetic peptide, not just for dimer formation.

The next two peptides (peptide 17a, and 18) each contain in their 8-amino acid linker a Lys or Cys residue. These two compounds are precursors to the two pegylated peptides (peptide 19 and 20) in which the side chain of the Lys or Cys is modified by a polyethylene glycol (PEG) moiety. It was decided to introduce a PEG moiety in the middle of a relatively long linker, so that the large PEG component (5 kDa) is far enough away from the important binding sites in the peptide molecule. PEG is a known biocompatible polymer which is increasingly used as a covalent modifier to improve the pharmacokinetic profiles of peptide- and protein-based therapeutics.

A modular, solution based method was devised for convenient pegylation of synthetic or recombinant peptides. The method is based on the now well established chemoselective ligation strategy which utilizes the specific reaction between a pair of mutually reactive functionalities. So, for pegylated peptide 19, the lysine side chain was preactivated with a bromoacetyl group to give peptide 17b to accommodate reaction with a thiol-derivatized PEG. To do that, an orthogonal protecting group, Dde, was employed for the protection of the lysine ε-amine. Once the whole peptide chain was assembled, the N-terminal amine was reprotected with t-Boc. Dde was then removed to allow for the bromoacetylation. This strategy gave a high quality crude peptide which was easily purified using conventional reverse phase HPLC. Ligation of the peptide with the thiol-modified PEG took place in aqueous buffer at pH 8 and the reaction completed within 30 min. MALDI-MS analysis of the purified, pegylated material revealed a characteristic, bell-shaped spectrum with an increment of 44 Da between the adjacent peaks. For PEG-peptide 20, a cysteine residue was placed in the linker region and its side chain thiol group would serve as an attachment site for a maleimide-containing PEG. Similar conditions were used for the pegylation of this peptide. As the assay data revealed, these two pegylated peptides had even higher in vitro bioactivity as compared to their unpegylated counterparts.

Peptide 21 has in its 8-amino acid linker a potential glycosylation motif, NGS. Since the exemplary tandem dimers are made up of natural amino acids linked by peptide bonds, expression of such a molecule in an appropriate eukaryotic cell system should produce a glycopeptide with the carbohydrate moiety added on the side chain carboxyamide of Asn. Glycosylation is a common post-translational modification process which can have many positive impacts on the biological activity of a given protein by increasing its aqueous solubility and in vivo stability. As the assay data show, incorporation of this glycosylation motif into the linker maintained high bioactivity. The synthetic precursor of the potential glycopeptide had in effect an activity comparable to that of the -(Gly)$_8$-linked analog. Once glycosylated, this peptide is expected to have the same order of activity as the pegylated peptides, because of the similar chemophysical properties exhibited by a PEG and a carbohydrate moiety.

The last peptide is a dimer of a dimer. It was prepared by oxidizing peptide 18, which formed an intermolecular disulfide bond between the two cysteine residues located at the linker This peptide was designed to address the possibility that TMP was active as a tetramer. The assay data showed that this peptide was not more active than an average tandem dimer on an adjusted molar basis, which indirectly supports the idea that the active form of TMP is indeed a dimer, otherwise dimerization of a tandem dimer would have a further impact on the bioactivity.

The following Table I summarizes relative activities of the above-described compounds in terms of the EC50 based on in vitro assays as described above.

TABLE I

| Compound | | Relative Potency |
|---|---|---|
| TPO | | 4.0 |
| TMP monomer (SEQ ID NO: 1) | | 1.0 |
| TMP C-C dimer (SEQ ID NO: 2) | | 3.5 |
| TMP-(Gly)$_n$-TMP: | | |
| 1 | n = 0 | 4.5 |
| 2 | n = 1 | 4.0 |
| 3 | n = 2 | 4.0 |
| 4 | n = 3 | 4.0 |
| 5 | n = 4 | 4.0 |
| 6 | n = 5 | 4.0 |
| 7 | n = 6 | 4.0 |
| 8 | n = 7 | 4.0 |
| 9 | n = 8 | 4.5 |
| 10 | n = 9 | 4.0 |
| 11 | n = 10 | 4.0 |
| 12 | n = 14 | 4.0 |
| 13 | TMP-GPNG-TMP (SEQ ID NO. 10) | 3.0 |
| 14 | IEGPTLRQCLAARA-GGGGGGGG-IEGPTLRQCLAARA (SEQ ID NO. 11) | 0.5 |
| 15 | IEGPTLRQCLAARA-GGGGGGGG-IEGPTLRQCLAARA (SEQ ID NO. 12) | 0.5 |
| 16 | IEGPTLRQALAARA-GGGGGGGG-IEGPTLRQALAARA (SEQ ID NO. 13) | 0.5 |
| 17a | TMP-GGGKGGGG-TMP (SEQ ID NO. 14) | 4.0 |
| 17b | TMP-GGGK(BrAc)GGGG-TMP (SEQ ID NO. 15) | ND |
| 18 | TMP-GGGCGGGG-TMP (SEQ ID NO. 16) | 4.0 |
| 19 | TMP-GGGK(PEG)GGGG-TMP (SEQ ID NO. 17) | 5.0 |
| 20 | TMP-GGGC(PEG)GGGG-TMP (SEQ ID NO. 18) | 5.0 |
| 21 | TMP-GGGNGSGG-TMP (SEQ ID NO. 19) | 4.0 |
| 22 | TMP-GGGCGGGG-TMP (SEQ ID NO. 20) TMP-GGGCGGGG-TMP | 4.0 |

NOTE:
In Table 1, numerals indicate approximately 1 log of activity, so that the difference in activity between "1" and "4" is approximately 1000-fold. An increment of 0.5 is an intermediate point, so that the difference in activity between "1" and "3.5" is approximately 500-fold. "ND" means not determined.

II. The following sets forth exemplary methods for making some of the compounds of the second group disclosed herein.
A. Preparation of an Fc Fusion Compound of the Type Shown in FIG. 6C.

A DNA sequence coding for the Fc region of human IgG1 fused in-frame to a dimer of the TPO-mimetic peptide (SEQ ID NO: 34) was placed under control of the luxPR promoter in the plasmid expression vector pAMG21 as follows.

The fusion gene was constructed using standard PCR technology. Templates for PCR reactions were the fusion vector containing the Fc sequence and a synthetic gene encoding the remainder of the compound of SEQ ID NO: 34. The synthetic gene was constructed from the 4 overlapping oligonucleotides shown below:

```
1830-52
                                       (SEQ ID NO: 35)
AAA GGT GGA GGT GGT GGT ATC GAA GGT CCG

ACT CTG CGT CAG TGG CTG GCT GCT CGT GCT 1830-53
                                       (SEQ ID NO: 36)
ACC TCC ACC ACC AGC ACG AGC AGC CAG

CCA CTG ACG CAG AGT CGG ACC 1830-54
                                       (SEQ ID NO: 37)
GGT GGT GGA GGT GGC GGC GGA GGT ATT GAG

GGC CCA ACC CTT CGC CAA TGG CTT GCA GCA

CGC GCA 1830-55
                                       (SEQ ID NO: 38)
AAA AAA AGG ATC CTC GAG ATT ATG CGC GTG

CTG CAA GCC ATT GGC GAA GGG TTG GGC CCT

CAA TAC CTC CGC CGC C
```

The 4 oligonucleotides were annealed to form the duplex shown below:

```
AAAGGTGGAGGTGGTGGTATCGAAGGTCCGACTCTGCGTCAGTGGCTGGCTGCTCGTGCT
1--------+---------+---------+---------+---------+---------+   60
                              CCAGGCTGAGACGCAGTCACCGACCGACGAGCACGA
 K  G  G  G  G  I  E  G  P  T  L  R  Q  W  L  A  A  R  A

GGTGGTGGAGGTGGCGGCGGAGGTATTGAGGGCCCAACCCTTCGCCAATGGCTTGCAGCA
---------+---------+---------+---------+---------+---------+ 120
CCACCACCTCCACCGCCGCCTCCATAACTCCCGGGTTGGGAAGCGGTTACCGAACGTCGT
 G  G  G  G  G  G  I  E  G  P  T  R  Q  W  L  L  A  A

CGCGCA
------------------------                                     148
GCGCGTATTAGAGCTCCTAGGAAAAAAA
 R  A  *
```

SEQ ID NO: 39 [co-linear oligonucleotides 1830-52 and 1830-54]

SEQ ID NO: 40 [co-linear oligonucleotides 1830-53 and 1830-55]
and SEQ ID NO: 41 [the encoded amino acid sequence]
This duplex was amplified in a PCR reaction using 1830-52 and 1830-55 as the sense and antisense primers.

The Fc portion of the molecule was generated in a PCR reaction with Fc DNA using the primers

```
1216-52
                                       (SEQ ID NO: 42)
AAC ATA AGT ACC TGT AGG ATC G 1830-51
                                       (SEQ ID NO: 43)
TTCGATACCACCACCTCCACCTTTACCCGGAG-

ACAGGGAGAGGCTCTTCTGC
```

The oligonucleotides 1830-51 and 1830-52 contain an overlap of 24 nucleotides, allowing the two genes to be fused together in the correct reading frame by combining the above PCR products in a third reaction using the outside primers, 1216-52 and 1830-55

The final PCR gene product (the full length fusion gene) was digested with restriction endonucleases XbaI and BamHI, and then ligated into the vector pAMG21 (see below), also digested with XbaI and BamHI. Ligated DNA was transformed into competent host cells of *E. coli* strain 2596 (GM221, described below). Clones were screened for the ability to produce the recombinant protein product and to possess the gene fusion having the correct nucleotide sequence. Protein expression levels were determined from 50 ml shaker flask studies. Whole cell lysates were analyzed for expression of the fusion via Coomassie stained PAGE gels.

The amino acid sequence of the fusion protein is shown below the corresponding nucleotide sequence:

```
    XbaI
     |
     TCTAGATTTGTTTTAACTAATTAAAGGAGGAATAACATATGGACAAAACTCACACATGTC
  1  ---------+---------+---------+---------+---------+---------+   60
     AGATCTAAACAAAATTGATTAATTTCCTCCTTATTGTATACCTGTTTTGAGTGTGTACAG
                                            M  D  K  T  H  T  C  P

CACCTTGTCCAGCTCCGGAACTCCTGGGGGACCGTCAGTCTTCCTCTTCCCCCCAAAAC
 61  ---------+---------+---------+---------+---------+---------+  120
     GTGGAACAGGTCGAGGCCTTGAGGACCCCCCTGGCAGTCAGAAGGAGAAGGGGGGTTTTG
      P  C  P  A  P  E  L  L  G  G  P  S  V  F  L  F  P  P  K  P

CCAAGGACACCCTCATGATCTCCCGGACCCCTGAGGTCACATGCGTGGTGGTGGACGTGA
121  ---------+---------+---------+---------+---------+---------+  180
     GGTTCCTGTGGGAGTACTAGAGGGCCTGGGGACTCCAGTGTACGCACCACCACCTGCACT
      K  D  T  L  M  I  S  R  T  P  E  V  T  C  V  V  V  D  V  S

GCCACGAAGACCCTGAGGTCAAGTTCAACTGGTACGTGGACGGCGTGGAGGTGCATAATG
181  ---------+---------+---------+---------+---------+---------+  240
     CGGTGCTTCTGGGACTCCAGTTCAAGTTGACCATGCACCTGCCGCACCTCCACGTATTAC
      H  E  D  P  E  V  K  F  N  W  Y  V  D  G  V  E  V  H  N  A
```

-continued

```
      CCAAGACAAAGCCGCGGGAGGAGCAGTACAACAGCACGTACCGTGTGGTCAGCGTCCTCA
241   ---------+---------+---------+---------+---------+---------+ 300
      GGTTCTGTTTCGGCGCCCTCCTCGTCATGTTGTCGTGCATGGCACACCAGTCGCAGGAGT
         K  T  K  P  R  E  E  Q  Y  N  S  T  Y  R  V  V  S  V  L  T

CCGTCCTGCACCAGGACTGGCTGAATGGCAAGGAGTACAAGTGCAAGGTCTCCAACAAAG
301   ---------+---------+---------+---------+---------+---------+ 360
      GGCAGGACGTGGTCCTGACCGACTTACCGTTCCTCATGTTCACGTTCCAGAGGTTGTTTC
         V  L  H  Q  D  W  L  N  G  K  E  Y  K  C  K  V  S  N  K  A

CCCTCCCAGCCCCCATCGAGAAAACCATCTCCAAAGCCAAAGGGCAGCCCCGAGAACCAC
361   ---------+---------+---------+---------+---------+---------+ 420
      GGGAGGGTCGGGGGTAGCTCTTTTGGTAGAGGTTTCGGTTTCCCGTCGGGGCTCTTGGTG
         L  P  A  P  I  E  K  T  I  S  K  A  K  G  Q  P  R  E  P  Q

AGGTGTACACCCTGCCCCCATCCCGGGATGAGCTGACCAAGAACCAGGTCAGCCTGACCT
421   ---------+---------+---------+---------+---------+---------+ 480
      TCCACATGTGGGACGGGGGTAGGGCCCTACTCGACTGGTTCTTGGTCCAGTCGGACTGGA
         V  Y  T  L  P  P  S  R  D  E  L  T  K  N  Q  V  S  L  T  C

GCCTGGTCAAAGGCTTCTATCCCAGCGACATCGCCGTGGAGTGGGAGAGCAATGGGCAGC
481   ---------+---------+---------+---------+---------+---------+ 540
      CGGACCAGTTTCCGAAGATAGGGTCGCTGTAGCGGCACCTCACCCTCTCGTTACCCGTCG
         L  V  K  G  F  Y  P  S  D  I  A  V  E  W  E  S  N  G  Q  P

CGGAGAACAACTACAAGACCACGCCTCCCGTGCTGGACTCCGACGGCTCCTTCTTCCTCT
541   ---------+---------+---------+---------+---------+---------+ 600
      GCCTCTTGTTGATGTTCTGGTGCGGAGGGCACGACCTGAGGCTGCCGAGGAAGAAGGAGA
         E  N  N  Y  K  T  T  P  P  V  L  D  S  D  G  S  F  F  L  Y

ACAGCAAGCTCACCGTGGACAAGAGCAGGTGGCAGCAGGGGAACGTCTTCTCATGCTCCG
601   ---------+---------+---------+---------+---------+---------+ 660
      TGTCGTTCGAGTGGCACCTGTTCTCGTCCACCGTCGTCCCCTTGCAGAAGAGTACGAGGC
         S  K  L  T  V  D  K  S  R  W  Q  Q  G  N  V  F  S  C  S  V

TGATGCATGAGGCTCTGCACAACCACTACACGCAGAAGAGCCTCTCCCTGTCTCCGGGTA
661   ---------+---------+---------+---------+---------+---------+ 720
      ACTACGTACTCCGAGACGTGTTGGTGATGTGCGTCTTCTCGGAGAGGGACAGAGGCCCAT
         M  H  E  A  L  H  N  H  Y  T  Q  K  S  L  S  L  S  P  G  K

AAGGTGGAGGTGGTGGTATCGAAGGTCCGACTCTGCGTCAGTGGCTGGCTGCTCGTGCTG
721   ---------+---------+---------+---------+---------+---------+ 780
      TTCCACCTCCACCACCATAGCTTCCAGGCTGAGACGCAGTCACCGACCGACGAGCACGAC
         G  G  G  G  I  E  G  P  T  L  R  Q  W  L  A  A  R  A  G

GTGGTGGAGGTGGCGGCGGAGGTATTGAGGGCCCAACCCTTCGCCAATGGCTTGCAGCAC
781   ---------+---------+---------+---------+---------+---------+ 840
      CACCACCTCCACCGCCGCCTCCATAACTCCCGGGTTGGGAAGCGGTTACCGAACGTCGTG
         G  G  G  G  G  G  I  E  G  P  T  L  R  Q  W  L  A  A  R

BamHI
               |
      GCGCATAATCTCGAGGATCCG
841   ---------+---------+- 861
      CGCGTATTAGAGCTCCTAGGC
         A
```

SEQ ID NO: 44 [single strand reading 5'→3' above],
SEQ ID NO: 45 [single strand reading 3'→5' above] and
SEQ ID NO: 46 [the encoded amino acid sequence]
pAMG21

The expression plasmid pAMG21 is available from the ATCC under accession number 98113, which was deposited on Jul. 24, 1996, at the American Type Culture Collection, 12301 Parklawn Drive, Rockville, Md. 20852.

The Amgen host strain #2596 is an *E.coli* K-12 strain that has been modified to contain both the temperature sensitive lambda repressor cI857s7 in the early ebg region and the lacI$^Q$ repressor in the late ebg region (68 minutes). The presence of these two repressor genes allows the use of this host with a variety of expression systems, however both of these repressors are irrelevant to the expression from luxP$_R$. The untransformed host has no antibiotic resistances.

The ribosome binding site of the cI857s7 gene has been modified to include an enhanced RBS. It has been inserted into the ebg operon between nucleotide position 1170 and 1411 as numbered in Genbank accession number M64441Gb_Ba with deletion of the intervening ebg sequence.

The construct was delivered to the chromosome using a recombinant phage called MMebg-cI857s7 enhanced RBS #4 into F'tet/393. After recombination and resolution only the chromosomal insert described above remains in the cell. It was renamed F'tet/GM101.

F'tet/GM101 was then modified by the delivery of a lacI$^Q$ construct into the ebg operon between nucleotide position 2493 and 2937 as numbered in the Genbank accession number M64441Gb_Ba with the deletion of the intervening ebg sequence.

The construct was delivered to the chromosome using a recombinant phage called AGebg-LacIQ#5 into F'tet/GM101. After recombination and resolution only the chromosomal insert described above remains in the cell. It was renamed F'tet/GM221. The F'tet episome was cured from the strain using acridine orange at a concentration of 25 ug/ml in LB. The cured strain was identified as tetracyline sensitive and was stored as GM221.

The Fc fusion construct contained in plasmid pAMG21 (referred to herein as pAMG21-Fc-TMP-TMP), which in turn is contained in the host strain GM221 has been deposited at the ATCC under accession number 98957, with a deposit date of October 22, 1998.

Expression. Cultures of pAMG21-Fc-TMP-TMP in *E. coli* GM221 in Luria Broth medium containing 50 μg/ml kanamycin were incubated at 37°C. prior to induction. Induction of Fc-TMP-TMP gene product expression from the luxPR promoter was achieved following the addition of the synthetic autoinducer N-(3-oxohexanoyl)-DL-homoserine lactone to the culture media to a final concentration of 20 ng/ml and cultures were incubated at 37° C. for a further 3 hours. After 3 hours, the bacterial cultures were examined by microscopy for the presence of inclusion bodies and were then collected by centrifugation. Refractile inclusion bodies were observed in induced cultures indicating that the Fc-TMP-TMP was most likely produced in the insoluble fraction in E. coli. Cell pellets were lysed directly by resuspension in Laemmli sample buffer containing 10% β-mercaptoethanol and were analyzed by SDS-PAGE. An intense Coomassie stained band of approximately 30 kDa was observed on an SDS-PAGE gel. The expected gene product would be 269 amino acids in length and have an expected molecular weight of about 29.5 kDa. Fermentation was also carried out under standard batch conditions at the 10 L scale, resulting in similar expression levels of the Fc-TMP-TMP to those obtained at bench scale.

Purification of Fc-TMP-TMP.

Cells were broken in water (1/10) by high pressure homogenization (2 passes at 14,000 PSI) and inclusion bodies were harvested by centrifugation (4200 RPM in J-6B for 1 hour). Inclusion bodies were solubilized in 6 M guanidine, 50 mM Tris, 8 mM DTT, pH 8.7 for 1 hour at a 1/10 ratio. The solubilized mixture was diluted 20 times into 2 M urea, 50 mM Tris, 160 mM arginine, 3 mM cysteine, pH 8.5. The mixture was stirred overnight in the cold. At this point in the procedure the Fc-TMP-TMP monomer subunits dimerize to form the disulfide-linked compound having the structure shown in FIG. 6C. and then concentrated about 10 fold by ultafiltration. It was then diluted 3 fold with 10 mM Tris, 1.5 M urea, pH 9. The pH of this mixture was then adjusted to pH 5 with acetic acid. The precipitate was removed by centrifugation and the supernatant was loaded onto a SP-Sepharose Fast Flow column equilibrated in 20 mM NaAc, 100 mM NaCl, pH 5 (10 mg/ml protein load, room temperature). The protein was eluted off using a 20 column volume gradient in the same buffer ranging from 100 mM NaCl to 500 mM NaCl. The pool from the column was diluted 3 fold and loaded onto a SP-Sepharose HP column in 20 mM NaAc, 150 mM NaCl, pH 5 (10 mg/ml protein load, room temperature). The protein was eluted off using a 20 column volume gradient in the same buffer ranging from 150 mM NaCl to 400 mM NaCl. The peak was pooled and filtered.

III. The following is a summary of in vivo data in mice with various compounds of this invention.

Mice. Normal female BDF1 approximately 10-12 weeks of age.

Bleed schedule. Ten mice per group treated on day 0, two groups started 4 days apart for a total of 20 mice per group. Five mice bled at each time point, mice were bled a minimum of three times a week. Mice were anesthetized with isoflurane and a total volume of 140-160 µl of blood was obtained by puncture of the orbital sinus. Blood was counted on a Technicon H1E blood analyzer running software for murine blood. Parameters measured were white blood cells, red blood cells, hematocrit, hemoglobin, platelets, neutrophils.

Treatments. Mice were either injected subcutaneously for a bolus treatment or implanted with 7 day micro-osmotic pumps for continuous delivery.

Subcutaneous injections were delivered in a volume of 0.2 ml. Osmotic pumps were inserted into a subcutaneous incision made in the skin between the scapulae of anesthetized mice. Compounds were diluted in PBS with 0.1% BSA. All experiments included one control group, labeled "carrier" that were treated with this diluent only. The concentration of the test articles in the pumps was adjusted so that the calibrated flow rate from the pumps gave the treatment levels indicated in the graphs.

Compounds. A dose titration of the compound was delivered to mice in 7 day micro-osmotic pumps. Mice were treated with various compounds at a single dose of 100 ug/kg in 7 day osmotic pumps. Some of the same compounds were then given to mice as a single bolus injection.

Figure 4:
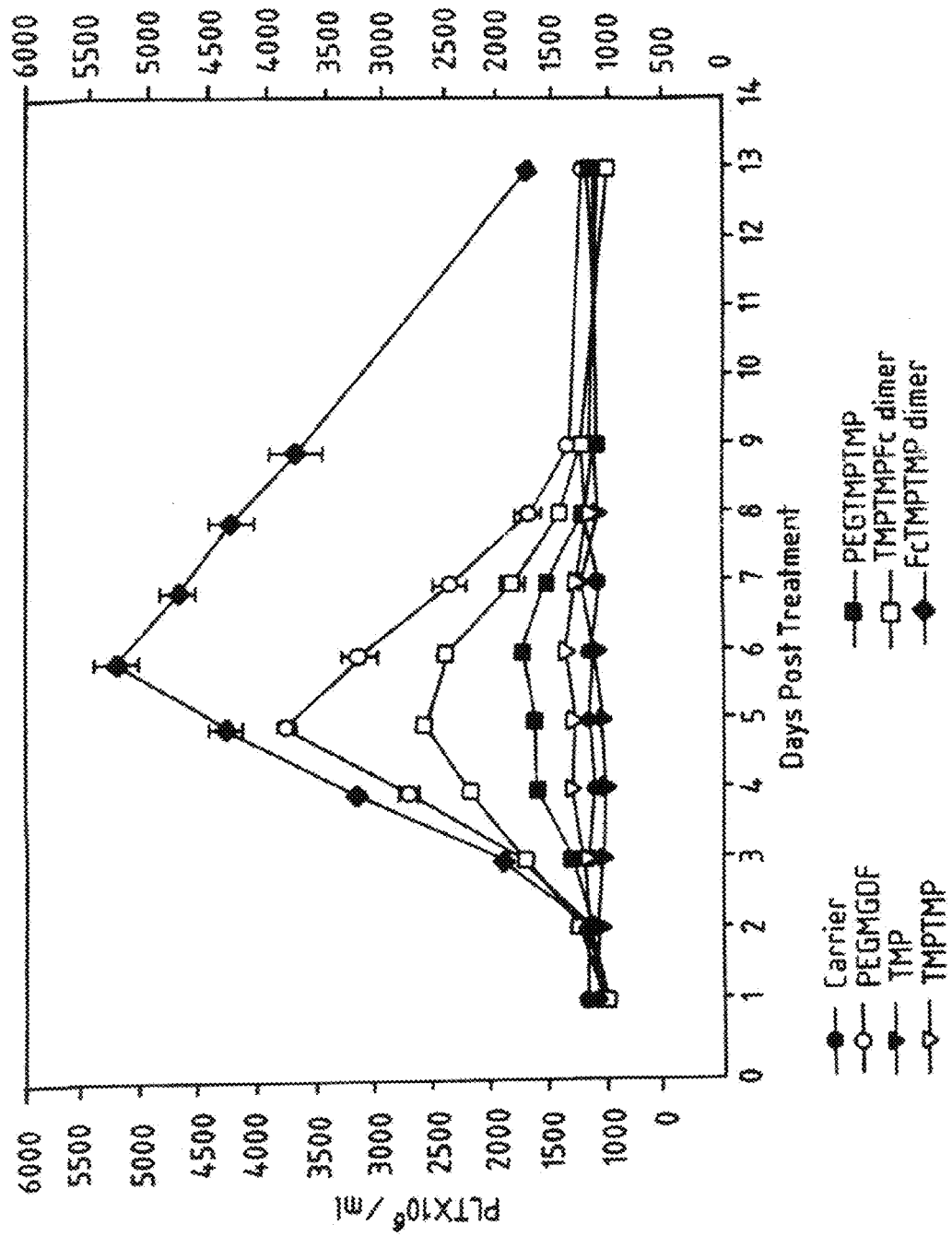
FIG. 4 shows the number of platelets generated in vivo in normal female BDF1 mice treated with one 100 µg/kg bolus injection of various compounds, as follows: PEG-MGDF means 20 kD average molecular weight PEG attached to the N-terminal amino group by reductive amination of amino acids 1-163 of native human TPO, which is expressed in E. coli (so that it is not glycosylated) (See WO 95/26746 entitled "Compositions and Methods for Stimulating Megakaryocyte Growth and Differentiation"); TMP means the compound of SEQ ID NO: 1; TMP-TMP means the compound of SEQ ID NO: 21; PEG-TMP-TMP means the compound of SEQ ID NO: 18, wherein the PEG group is a 5 kD average molecular weight PEG attached as shown in FIG. 3; TMP-TMP-Fc is defined herein below and Fc-TMP-TMP is the same as TMP-TMP-Fc except that the Fc group is attached at the N-terminal end rather than the C-terminal end of the TMP-TMP peptide.
Figure 5:
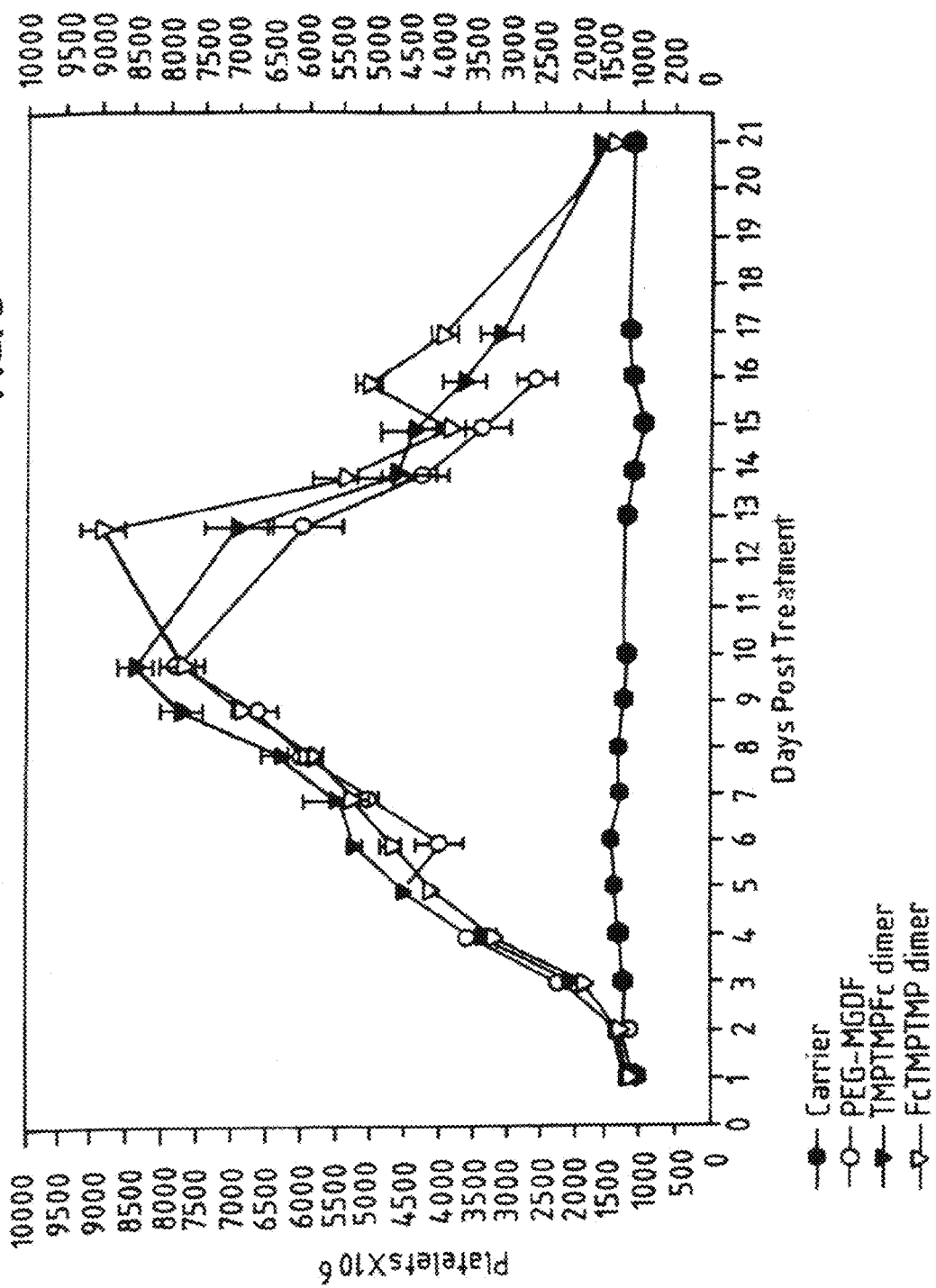
FIG. 5 shows the number of platelets generated in vivo in normal BDF1 mice treated with various compounds delivered via implanted osmotic pumps over a 7-day period. The compounds are defined in the same manner as set forth above for FIG. 4.

Activity test results. The results of the activity experiments are shown in FIGS. 4 and 5. In dose response assays using 7-day micro-osmotic pumps (data not shown) the maximum effect was seen with the compound of SEQ ID NO: 18 was at 100 µg/kg/day; the 10 µg/kg/day dose was about 50% maximally active and 1 µg/kg/day was the lowest dose at which activity could be seen in this assay system. The compound at 10 µg/kg/day dose was about equally active as 100 µg/kg/day unpegylated rHu-MGDF in the same experiment.

IV. Discussion

It is well accepted that MGDF acts in a way similar to human growth hormone (hGH), i.e., one molecule of the protein ligand binds two molecules of the receptor for its activation (Wells, J. A. et al., Ann. Rev. Biochem. 65:609-634 (1996))). This interaction is mimicked by the action of the much smaller TMP peptide. However, the present studies suggest that this mimicry requires the concerted action of two TMP molecules, as covalent dimerization of TMP in either a C—C parallel or C—N sequential fashion increased the in vitro biological potency of the original monomer by a factor of greater than $10^3$. The relatively low biopotency of the monomer is probably due to inefficient formation of the non-covalent dimer. A preformed covalent dimer has the ability to eliminate the entropy barrier for the formation of a noncovalent dimer which is exclusively driven by weak, noncovalent interactions between two molecules of the small, 14-residue peptide.

It is interesting to note that most of the tandem dimers are more potent than the C-terminal parallel dimers. Tandem dimerization seems to give the molecule a better fit conformation than does the C—C parallel dimerization. The seemingly unsymmetric feature of a tandem dimer might have brought it closer to the natural ligand which, as an unsymmetric molecule, uses two different sites to bind two identical receptor molecules.

Introduction of the PEG moiety was envisaged to enhance the in vivo activity of the modified peptide by providing it a protection against proteolytic degradation and by slowing down its clearance through renal filtration. It was unexpected that pegylation could further increase the in vitro bioactivity of a tandem dimerized TMP peptide in the cell-based proliferation assay.

V. The following is a summary of in vivo data in monkeys with various compounds of this invention.

In order to evaluate hematological parameters in female rhesus monkeys associated with administration of AMP2 via subcutaneous administration, the following protocol was designed and carried out. Five groups of three monkeys each were assembled. Group 1 served as control and received acetate buffer (20 mM sodium acetate, 0.25 M sodium chloride, pH 5) containing neither AMP2 nor pegylated, recombinant human MGDF (PEG-rHuMGDF). Group 2 received one or more dosage of AMP2 at intervals indicated below; Group 3 received 1000 µg/kg AMP2 at intervals indicated below; Group 4 received 5000 µg/kg AMP2 at intervals indicated below; and Group 5 received 100 µg/kg PEG-rHuMGDF at intervals indicated below.

The day on which the first single dose was administered was designated as Day 0 of Cycle 1. In Cycle 2, doses were administered on Days 21, 23, 25, 28, 30 and 32. During Cycle 3, a single dose was administered on Day 84, and in Cycle 4, a single dose was administration on Day 123. Animals were observed for clinical signs once daily during the acclimation period, three times daily (prior to dosing, immediately to 30 minutes following dosing, and 2 to 3 hours following dosing) on the dosing days, and once daily on the non-dosing days. Food consumption was calculated daily based on the number of food pieces given and the number left over for each animal from 7 days prior to the initiation of the dosing period to the end of the recovery period. Body weight for each animal was measured twice prior to the dosing regimen and twice during the dosing and recovery periods. Blood samples for hematology were prepared once prior to the initiation of dosing and once on Days 1, 3, 5, 7, 9, 11, 13, 15, 20, 22, 24, 26, 29, 31, 33, 35, 37, 39, 41, 43, 45, 47, 49, 55, 62, 69, 76, 83, 85, 87, 89, 91, 93, 95, 97, 99, 101, 103, 105, 111, 122, 124, 126, 128, 130, 132, 134, 136, 138, 140, 142, 144, 150. For pharmacokinetic analysis. 0.5 ml serum samples were collected once prior to dosing and once at 1, 4 and 24 hours after dosing. Samples were collected on Days 0, 21, 32, 84, and 123 and stored at approximately −70° C. until analysis. For antibody analysis, 2 ml blood samples were collected one week prior to the single dose and once on Days 0 (prior to dosing), 6, 13, 20, 27, 34, 41, 48, 55, 62, 69, 76, 83, 90, 97, 104, 111, 118, 129, 136, 143 and 150. Samples were stored at −70° C. until analysis.

Results indicated that platelet values increased in all treated groups with the largest increases seen in the PEG-rHuMGDF and high dose AMP2 groups. In Cycle 1, peak platelet values increased approximately 3.3-fold and 3.1-fold in the PEG-rHuMGDF group (Day 9) and 5000 µg/kg AMP2 group ((Day 9), respectively, compared to the mean platelet count in the control group. The low dose AMP2 platelet values increased approximately 1.5-fold higher than control on the same specified study days. Similar responses were noted in all other cycles.

However, in Cycle 4, the PEG-rHuMGDF group did not demonstrate as large of an increased platelet count as in the previous cycles. The PEG-rHuMGDF group has increased platelet counts of approximately 2-fold that in the control group 9 days after the dose of this cycle. For comparison, the mean platelet count in the highest dose AMP2 group in Cycle 4 was 3.3-fold higher than the control group. Additionally, PEG-rHuMGDF animals has a mean platelet count 53% lower than the control group mean platelet count at the start of Cycle 4 (per dose) and the mean platelet count for the group at the end of Cycle 4 *(27 days post dose) was 79% lower than that of the control group. For all AMP2 animals, the mean platelet counts at the start and end of Cycle 4 were ±15% of the platelet count in the control group.

In Cycle 1 and 2, a trend toward a decrease in red blood cell (RBC) counts was noted in all treated groups as compared to control. The decrease was most evident by Days 41 to 43 and the largest decrease in RBC was noted in the PEG-rHuMGDF group. The counts began returning to normal levels (as compared to control) as early as Day 47. The white blood cell (WBC) levels during Cycles 1 and 2 were dramatically increased (2.6-fold) as compared to control on Day 35. A slight increase was noted in the 5000 µg/kg AMP2 group on Day 33. Values headed toward normal (control) levels beginning on Day 37. A similar response was seen in Cycle 3 with no apparent change in WBC in Cycle 4 in any of the treated groups.

During Cycle 3, RBC counts were slightly decreased by Day 13 (following the single Cycle 3 dose) in all treated groups except for the 500 µg/kg AMP2 group. RBC values began returning to normal levels (as compared to control) by Day 17.

In Cycle 4, RBC counts decreased in all treated groups as compared to control except in the 500 µg/kg AMP2 group. Unlike the other cycles, there was more than one nadir present in this cycle. These decreases appeared from Day 1-9 post dose and began to recover as early as Day 11.

The results indicated that an increase in platelet counts, above that of control animals could be detected 7 to 9 days following dosing in all treated animals in all cycles tested. It appeared that the repeated dose phase caused a higher response in platelet production as compared to the single dose phases. By Cycle 4, the platelet response elicited by the PEG-rHuMGDF group was lower compared to the previous cycles and compared to that of the high dose AMP2 response. Decreases in RBC counts were noted in Cycles 1, 2, 3 and 4 in most treated groups at some point during each cycle of the study, however, all hematology parameters returned to normal levels (as compared to control) after dosing cessation.

Overall, these results indicated that treatment with AMP2 was well tolerated in the rhesus monkeys and that AMP2 resulted in increased platelet counts after various cycles of treatment. It did not appear, based on the platelet count results, that there was a biologically significant immune-mediated response to AMP2. In contrast, treatment in the various cycles with PEG-rHuMGDF did show an inhibition in platelet response by Cycle 4, suggesting that antibodies to PEG-rHuMGDF have been generated and these anti-MGDF antibodies may be crossreacting with endogenous rhesus TPO.

The invention now being fully described, it will be apparent to one of ordinary skill in the art that many changes and modifications can be made thereto, without departing from the spirit and scope of the invention as set forth herein.

SEQUENCE LISTING

<160> NUMBER OF SEQ ID NOS: 58

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide

<400> SEQUENCE: 1

Ile Glu Gly Pro Thr Leu Arg Gln Trp Leu Ala Ala Arg Ala
 1               5                   10

```
<210> SEQ ID NO 2
<211> LENGTH: 14
<212> TYPE: PRT
<213> ORGANISM: Artificial Sequence
<220> FEATURE:
<223> OTHER INFORMATION: Synthetic peptide
<220> FEATURE:
<223> OTHER INFORMATION: Peptide is a subunit of a homodimer: Subunits
      in the dimer are covalently bonded at each carboxy
      terminus through peptide linkage with
      NH2-CH2-CH2-CH2-CH2-CH(CONH2)-NH-CO-CH2-CH2-NH2

<400> SEQUENCE: 2

Ile Glu Gly Pro Thr Leu Arg Gln Trp Leu Ala Ala Arg Ala
 1               5                  10

<210> SEQ ID NO 3
<211> LENGTH: 684
<212> TYPE: DNA
<213> ORGANISM: Homo sapiens

<400> SEQUENCE: 3
atggacaaaa ctcacacatg tccaccttgt ccagctccgg aactcctggg gggaccgtca      60
gtcttcctct tccccccaaa acccaaggac accctcatga tctcccggac ccctgaggtc     120
acatgcgtgg tggtggacgt gagccacgaa gaccctgagg tcaagttcaa ctggtacgtg     180
gacggcgtgg aggtgcataa tgccaagaca aagccgcggg aggagcagta caacagcacg     240
taccgtgtgg tcagcgtcct caccgtcctg caccaggact ggctgaatgg caaggagtac     300
aagtgcaagg tctccaacaa agccctccca gcccccatcg agaaaaccat ctccaaagcc     360
aaagggcagc cccgagaacc acaggtgtac accctgcccc catcccggga tgagctgacc     420
aagaaccagg tcagcctgac ctgcctggtc aaaggcttct atcccagcga catcgccgtg     480
gagtgggaga gcaatgggca gccggagaac aactacaaga ccacgcctcc cgtgctggac     540
tccgacggct ccttcttcct ctacagcaag ctcaccgtgg acaagagcag gtggcagcag     600
gggaacgtct tctcatgctc cgtgatgcat gaggctctgc acaaccacta cacgcagaag     660
agcctctccc tgtctccggg taaa                                            684

<210> SEQ ID NO 4
<211> LENGTH: 684
<212> TYPE: DNA
<213> ORGANISM: Homo sapiens

<400> SEQUENCE: 4
tacctgtttt gagtgtgtac aggtggaaca ggtcgaggcc ttgaggaccc ccctggcagt      60
cagaaggaga agggggggttt tgggttcctg tgggagtact agagggcctg ggactccag     120 tgtacgcacc accacctgca ctcggtgctt ctggactcc agttcaagtt gaccatgcac     180
ctgccgcacc tccacgtatt acggttctgt tcctcgcgccc tcctcgtcat gttgtcgtgc    240
atggcacacc agtcgcagga gtggcaggac gtggtcctga ccgacttacc gttcctcatg    300
ttcacgttcc agaggttgtt tcgggagggt cgggggtagc tcttttggta gaggtttcgg    360
tttcccgtcg gggctcttgg tgtccacatg tgggacgggg gtaggccct actcgactgg     420 ttcttggtcc agtcggactg gacggaccag tttccgaaga tagggtcgct gtagcggcac    480
ctcaccctct cgttacccgt cggcctcttg ttgatgttct ggtgcggagg gcacgacctg    540
aggctgccga ggaagaagga gatgtcgttc gagtggcacc tgttctcgtc caccgtcgtc    600
cccttgcaga agagtacgag gcactacgta ctccgagacg tgttggtgat gtgcgtcttc    660
tcggagaggg acagaggccc attt                                           684
```

```
<210> SEQ ID NO 5
<211> LENGTH: 228
<212> TYPE: PRT
<213> ORGANISM: Artificial Sequence
<220> FEATURE:
<223> OTHER INFORMATION: Synthetic peptide

<400> SEQUENCE: 5

Met Asp Lys Thr His Thr Cys Pro Pro Cys Pro Ala Pro Glu Leu Leu
 1               5                  10                  15

Gly Gly Pro Ser Val Phe Leu Phe Pro Pro Lys Pro Lys Asp Thr Leu
             20                  25                  30

Met Ile Ser Arg Thr Pro Glu Val Thr Cys Val Val Val Asp Val Ser
         35                  40                  45

His Glu Asp Pro Glu Val Lys Phe Asn Trp Tyr Val Asp Gly Val Glu
     50                  55                  60

Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide

<400> SEQUENCE: 6

Gly Gly Gly Lys Gly Gly Gly Gly
 1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide

<400> SEQUENCE: 7

Gly Gly Gly Asn Gly Ser Gly Gly
```

<210> SEQ ID NO 8
<211> LENGTH: 8
<212> TYPE: PRT
<213> ORGANISM: Artificial Sequence
<220> FEATURE:
<223> OTHER INFORMATION: Synthetic peptide

<400> SEQUENCE: 8

Gly Gly Gly Cys Gly Gly Gly Gly
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic peptide

<400> SEQUENCE: 9

Gly Pro Asn Gly
1

<210> SEQ ID NO 10
<211> LENGTH: 32
<212> TYPE: PRT
<213> ORGANISM: Artificial Sequence
<220> FEATURE:
<223> OTHER INFORMATION: Synthetic peptide

<400> SEQUENCE: 10

Ile Glu Gly Pro Thr Leu Arg Gln Trp Leu Ala Ala Arg Ala Gly Pro
1               5                   10                  15

Asn Gly Ile Glu Gly Pro Thr Leu Arg Gln Trp Leu Ala Ala Arg Ala
            20                  25                  30

<210> SEQ ID NO 11
<211> LENGTH: 36
<212> TYPE: PRT
<213> ORGANISM: Artificial Sequence
<220> FEATURE:
<223> OTHER INFORMATION: Synthetic peptide
<220> FEATURE:
<223> OTHER INFORMATION: Cyclic peptide; Secondary structure is
      maintained by disulfide bond between intramolecular Cys
      residues at positions 9 and 31

<400> SEQUENCE: 11

Ile Glu Gly Pro Thr Leu Arg Gln Cys Leu Ala Ala Arg Ala Gly Gly
1               5                   10                  15

Gly Gly Gly Gly Gly Gly Ile Glu Gly Pro Thr Leu Arg Gln Cys Leu
            20                  25                  30

Ala Ala Arg Ala
        35

<210> SEQ ID NO 12
<211> LENGTH: 36
<212> TYPE: PRT
<213> ORGANISM: Artificial Sequence
<220> FEATURE:
<223> OTHER INFORMATION: Synthetic peptide

<400> SEQUENCE: 12

Ile Glu Gly Pro Thr Leu Arg Gln Cys Leu Ala Ala Arg Ala Gly Gly
1               5                   10                  15

```
Gly Gly Gly Gly Gly Gly Ile Glu Gly Pro Thr Arg Leu Gln Cys Leu
            20                  25                  30

Ala Ala Arg Ala
        35

<210> SEQ ID NO 13
<211> LENGTH: 36
<212> TYPE: PRT
<213> ORGANISM: Artificial Sequence
<220> FEATURE:
<223> OTHER INFORMATION: Synthetic peptide

<400> SEQUENCE: 13

Ile Glu Gly Pro Thr Leu Arg Gln Ala Leu Ala Ala Arg Ala Gly Gly
 1               5                  10                  15

Gly Gly Gly Gly Gly Gly Ile Glu Gly Pro Thr Leu Arg Gln Ala Leu
            20                  25                  30

Ala Ala Arg Ala
        35

<210> SEQ ID NO 14
<211> LENGTH: 36
<212> TYPE: PRT
<213> ORGANISM: Artificial Sequence
<220> FEATURE:
<223> OTHER INFORMATION: Synthetic peptide

<400> SEQUENCE: 14

Ile Glu Gly Pro Thr Leu Arg Gln Trp Leu Ala Ala Arg Ala Gly Gly
 1               5                  10                  15

Gly Lys Gly Gly Gly Gly Ile Glu Gly Pro Thr Leu Arg Gln Trp Leu
            20                  25                  30

Ala Ala Arg Ala
        35

<210> SEQ ID NO 15
<211> LENGTH: 36
<212> TYPE: PRT
<213> ORGANISM: Artificial Sequence
<220> FEATURE:
<223> OTHER INFORMATION: Lys residue at position 18 is Bromoacetylated
<220> FEATURE:
<223> OTHER INFORMATION: Synthetic peptide

<400> SEQUENCE: 15

Ile Glu Gly Pro Thr Leu Arg Gln Trp Leu Ala Ala Arg Ala Gly Gly
 1               5                  10                  15

Gly Lys Gly Gly Gly Gly Ile Glu Gly Pro Thr Leu Arg Gln Trp Leu
            20                  25                  30

Ala Ala Arg Ala
        35

<210> SEQ ID NO 16
<211> LENGTH: 36
<212> TYPE: PRT
<213> ORGANISM: Artificial Sequence
<220> FEATURE:
<223> OTHER INFORMATION: Synthetic peptide

<400> SEQUENCE: 16

Ile Glu Gly Pro Thr Leu Arg Gln Trp Leu Ala Ala Arg Ala Gly Gly
 1               5                  10                  15

Gly Cys Gly Gly Gly Gly Ile Glu Gly Pro Thr Leu Arg Gln Trp Leu
            20                  25                  30
```

Ala Ala Arg Ala
        35

<210> SEQ ID NO 17
<211> LENGTH: 36
<212> TYPE: PRT
<213> ORGANISM: Artificial Sequence
<220> FEATURE:
<223> OTHER INFORMATION: Lys at position 18 is pegylated
<220> FEATURE:
<223> OTHER INFORMATION: Synthetic peptide

<400> SEQUENCE: 17

Ile Glu Gly Pro Thr Leu Arg Gln Trp Leu Ala Ala Arg Ala Gly Gly
 1               5                  10                  15

Gly Lys Gly Gly Gly Gly Ile Glu Gly Pro Thr Leu Arg Gln Trp Leu
            20                  25                  30

Ala Ala Arg Ala
        35

<210> SEQ ID NO 18
<211> LENGTH: 36
<212> TYPE: PRT
<213> ORGANISM: Artificial Sequence
<220> FEATURE:
<223> OTHER INFORMATION: Cys at position 18 is pegylated
<220> FEATURE:
<223> OTHER INFORMATION: Synthetic peptide

<400> SEQUENCE: 18

Ile Glu Gly Pro Thr Leu Arg Gln Trp Leu Ala Ala Arg Ala Gly Gly
 1               5                  10                  15

Gly Cys Gly Gly Gly Gly Ile Glu Gly Pro Thr Leu Arg Gln Trp Leu
            20                  25                  30

Ala Ala Arg Ala
        35

<210> SEQ ID NO 19
<211> LENGTH: 36
<212> TYPE: PRT
<213> ORGANISM: Artificial Sequence
<220> FEATURE:
<223> OTHER INFORMATION: Synthetic peptide

<400> SEQUENCE: 19

Ile Glu Gly Pro Thr Leu Arg Gln Trp Leu Ala Ala Arg Ala Gly Gly
 1               5                  10                  15

Gly Asn Gly Ser Gly Gly Ile Glu Gly Pro Thr Leu Arg Gln Trp Leu
            20                  25                  30

Ala Ala Arg Ala
        35

<210> SEQ ID NO 20
<211> LENGTH: 36
<212> TYPE: PRT
<213> ORGANISM: Artificial Sequence
<220> FEATURE:
<223> OTHER INFORMATION: Monomeric subunit of a homodimer; Subunits in
      the homodimer are bonded by a disulfide bond between
      Cys residues at position 18 on each subunit
<220> FEATURE:
<223> OTHER INFORMATION: Synthetic peptide

<400> SEQUENCE: 20

Ile Glu Gly Pro Thr Leu Arg Gln Trp Leu Ala Ala Arg Ala Gly Gly

```
Gly Cys Gly Gly Gly Gly Ile Glu Gly Pro Thr Leu Arg Gln Trp Leu
            20                  25                  30

Ala Ala Arg Ala
        35

<210> SEQ ID NO 21
<211> LENGTH: 36
<212> TYPE: PRT
<213> ORGANISM: Artificial Sequence
<220> FEATURE:
<223> OTHER INFORMATION: Synthetic peptide

<400> SEQUENCE: 21

Ile Glu Gly Pro Thr Leu Arg Gln Trp Leu Ala Ala Arg Ala Gly Gly
1               5                   10                  15

Gly Gly Gly Gly Gly Gly Ile Glu Gly Pro Thr Leu Arg Gln Trp Leu
            20                  25                  30

Ala Ala Arg Ala
        35

<210> SEQ ID NO 22
<211> LENGTH: 32
<212> TYPE: PRT
<213> ORGANISM: Artificial Sequence
<220> FEATURE:
<223> OTHER INFORMATION: Peptide is derivatized at the amino teminus
      with a covalently bonded immunoglobulin Fc region
<220> FEATURE:
<223> OTHER INFORMATION: Synthetic peptide

<400> SEQUENCE: 22

Ile Glu Gly Pro Thr Leu Arg Gln Trp Leu Ala Ala Arg Ala Gly Pro
1               5                   10                  15

Asn Gly Ile Glu Gly Pro Thr Leu Arg Gln Trp Leu Ala Ala Arg Ala
            20                  25                  30

<210> SEQ ID NO 23
<211> LENGTH: 32
<212> TYPE: PRT
<213> ORGANISM: Artificial Sequence
<220> FEATURE:
<223> OTHER INFORMATION: Peptide is covalently bonded at the animo and
      carboxy termini to an immunoglobulin Fc region
<220> FEATURE:
<223> OTHER INFORMATION: Synthetic peptide

<400> SEQUENCE: 23

Ile Glu Gly Pro Thr Leu Arg Gln Trp Leu Ala Ala Arg Ala Gly Pro
1               5                   10                  15

Asn Gly Ile Glu Gly Pro Thr Leu Arg Gln Trp Leu Ala Ala Arg Ala
            20                  25                  30

<210> SEQ ID NO 24
<211> LENGTH: 36
<212> TYPE: PRT
<213> ORGANISM: Artificial Sequence
<220> FEATURE:
<223> OTHER INFORMATION: Peptide is copvalently bonded at the carboxy
      terminus to an immunoglobulin Fc region
<220> FEATURE:
<223> OTHER INFORMATION: Synthetic peptide

<400> SEQUENCE: 24

Ile Glu Gly Pro Thr Leu Arg Gln Trp Leu Ala Ala Arg Ala Gly Gly
1               5                   10                  15
```

```
Gly Gly Gly Gly Gly Gly Ile Glu Gly Pro Thr Leu Arg Gln Trp Leu
            20                  25                  30

Ala Ala Arg Ala
        35

<210> SEQ ID NO 25
<211> LENGTH: 34
<212> TYPE: PRT
<213> ORGANISM: Artificial Sequence
<220> FEATURE:
<223> OTHER INFORMATION: Peptide is covalently bonded at the amino
      terminus to an immunoglobulin Fc region
<220> FEATURE:
<223> OTHER INFORMATION: Synthetic peptide

<400> SEQUENCE: 25

Gly Gly Ile Glu Gly Pro Thr Leu Arg Gln Trp Leu Ala Ala Arg Ala
1               5                   10                  15

Gly Pro Asn Gly Ile Glu Gly Pro Thr Leu Arg Gln Trp Leu Ala Ala
            20                  25                  30

Arg Ala

<210> SEQ ID NO 26
<211> LENGTH: 36
<212> TYPE: PRT
<213> ORGANISM: Artificial Sequence
<220> FEATURE:
<223> OTHER INFORMATION: Peptide is covalently bonded at the amino
      terminus to an immunoglobulin Fc region
<220> FEATURE:
<223> OTHER INFORMATION: Synthetic peptide

<400> SEQUENCE: 26

Ile Glu Gly Pro Thr Leu Arg Gln Trp Leu Ala Ala Arg Ala Gly Gly
1               5                   10                  15

Gly Gly Gly Gly Gly Gly Ile Glu Gly Pro Thr Leu Arg Gln Trp Leu
            20                  25                  30

Ala Ala Arg Ala
        35

<210> SEQ ID NO 27
<211> LENGTH: 36
<212> TYPE: PRT
<213> ORGANISM: Artificial Sequence
<220> FEATURE:
<223> OTHER INFORMATION: Peptide is covalently bonded at the amino
      terminus to an immunoglobulin Fc region
<220> FEATURE:
<223> OTHER INFORMATION: Cyclic peptide; Secondary structure is
      maintained by disulfide linkage between intramolecular Cys
      residues at positions 9 and 31
<220> FEATURE:
<223> OTHER INFORMATION: Synthetic peptide

<400> SEQUENCE: 27

Ile Glu Gly Pro Thr Leu Arg Gln Cys Leu Ala Ala Arg Ala Gly Gly
1               5                   10                  15

Gly Gly Gly Gly Gly Gly Ile Glu Gly Pro Thr Leu Arg Gln Cys Leu
            20                  25                  30

Ala Ala Arg Ala
        35

<210> SEQ ID NO 28
<211> LENGTH: 36
<212> TYPE: PRT
```

```
<213> ORGANISM: Artificial Sequence
<220> FEATURE:
<223> OTHER INFORMATION: Peptide is covalently bonded at the amino
      terminus to an immunoglobulin Fc region
<220> FEATURE:
<223> OTHER INFORMATION: Synthetic peptide

<400> SEQUENCE: 28

Ile Glu Gly Pro Thr Leu Arg Gln Cys Leu Ala Ala Arg Ala Gly Gly
 1               5                  10                  15

Gly Gly Gly Gly Gly Gly Ile Glu Gly Pro Thr Leu Arg Gln Cys Leu
                20                  25                  30

Ala Ala Arg Ala
        35

<210> SEQ ID NO 29
<211> LENGTH: 36
<212> TYPE: PRT
<213> ORGANISM: Artificial Sequence
<220> FEATURE:
<223> OTHER INFORMATION: Synthetic peptide
<220> FEATURE:
<223> OTHER INFORMATION: Peptide is covalently bonded at the amino
      terminus to an immunoglobulin Fc region

<400> SEQUENCE: 29

Ile Glu Gly Pro Thr Leu Arg Gln Ala Leu Ala Ala Arg Ala Gly Gly
 1               5                  10                  15

Gly Gly Gly Gly Gly Gly Ile Glu Gly Pro Thr Leu Arg Gln Ala Leu
                20                  25                  30

Ala Ala Arg Ala
        35

<210> SEQ ID NO 30
<211> LENGTH: 36
<212> TYPE: PRT
<213> ORGANISM: Artificial Sequence
<220> FEATURE:
<223> OTHER INFORMATION: Peptide is covalently bonded at the amino
      terminus to an immunoglobulin Fc region
<220> FEATURE:
<223> OTHER INFORMATION: Synthetic peptide

<400> SEQUENCE: 30

Ile Glu Gly Pro Thr Leu Arg Gln Trp Leu Ala Ala Arg Ala Gly Gly
 1               5                  10                  15

Gly Lys Gly Gly Gly Gly Ile Glu Gly Pro Thr Leu Arg Gln Trp Leu
                20                  25                  30

Ala Ala Arg Ala
        35

<210> SEQ ID NO 31
<211> LENGTH: 36
<212> TYPE: PRT
<213> ORGANISM: Artificial Sequence
<220> FEATURE:
<223> OTHER INFORMATION: Peptide is covalently bonded at the amino
      terminus to an immunoglobulin Fc region
<220> FEATURE:
<223> OTHER INFORMATION: Synthetic peptide

<400> SEQUENCE: 31

Ile Glu Gly Pro Thr Leu Arg Gln Trp Leu Ala Ala Arg Ala Gly Gly
 1               5                  10                  15

Gly Cys Gly Gly Gly Gly Ile Glu Gly Pro Thr Leu Arg Gln Trp Leu
                20                  25                  30
```

Ala Ala Arg Ala
        35

<210> SEQ ID NO 32
<211> LENGTH: 36
<212> TYPE: PRT
<213> ORGANISM: Artificial Sequence
<220> FEATURE:
<223> OTHER INFORMATION: Synthetic peptide
<220> FEATURE:
<223> OTHER INFORMATION: Peptide is covalently bonded at the amino
      terminus to an immunoglobulin Fc region

<400> SEQUENCE: 32

Ile Glu Gly Pro Thr Leu Arg Gln Trp Leu Ala Ala Arg Ala Gly Gly
 1               5                  10                  15

Gly Asn Gly Ser Gly Gly Ile Glu Gly Pro Thr Leu Arg Gln Trp Leu
            20                  25                  30

Ala Ala Arg Ala
        35

<210> SEQ ID NO 33
<211> LENGTH: 36
<212> TYPE: PRT
<213> ORGANISM: Artificial Sequence
<220> FEATURE:
<223> OTHER INFORMATION: Synthetic peptide
<220> FEATURE:
<223> OTHER INFORMATION: Peptide is a subunit of a homodimer; Subunits
      in the homodimer are colvantly bonded through a
      disulfide bond between Cys residues at position 18
      of each subunit
<220> FEATURE:
<223> OTHER INFORMATION: Peptide is covalently bonded at the amino
      terminus to an immunoglobulin Fc region

<400> SEQUENCE: 33

Ile Glu Gly Pro Thr Leu Arg Gln Trp Leu Ala Ala Arg Ala Gly Gly
 1               5                  10                  15

Gly Cys Gly Gly Gly Gly Ile Glu Gly Pro Thr Leu Arg Gln Trp Leu
            20                  25                  30

Ala Ala Arg Ala
        35

<210> SEQ ID NO 34
<211> LENGTH: 41
<212> TYPE: PRT
<213> ORGANISM: Artificial Sequence
<220> FEATURE:
<223> OTHER INFORMATION: Synthetic peptide
<220> FEATURE:
<223> OTHER INFORMATION: Peptide is covalently bonded at the amino
      terminus to an immunoglobulin Fc region

<400> SEQUENCE: 34

Gly Gly Gly Gly Gly Ile Glu Gly Pro Thr Leu Arg Gln Trp Leu Ala
 1               5                  10                  15

Ala Arg Ala Gly Gly Gly Gly Gly Gly Gly Ile Glu Gly Pro Thr
            20                  25                  30

Leu Arg Gln Trp Leu Ala Ala Arg Ala
        35                  40

<210> SEQ ID NO 35
<211> LENGTH: 60
<212> TYPE: DNA
<213> ORGANISM: Artificial Sequence
<220> FEATURE:
<223> OTHER INFORMATION: Synthetic primer

<400> SEQUENCE: 35
aaaggtggag gtggtggtat cgaaggtccg actctgcgtc agtggctggc tgctcgtgct    60

<210> SEQ ID NO 36
<211> LENGTH: 48
<212> TYPE: DNA
<213> ORGANISM: Artificial Sequence
<220> FEATURE:
<223> OTHER INFORMATION: Synthetic primer

<400> SEQUENCE: 36
acctccacca ccagcacgag cagccagcca ctgacgcaga gtcggacc    48

<210> SEQ ID NO 37
<211> LENGTH: 66
<212> TYPE: DNA
<213> ORGANISM: Artificial Sequence
<220> FEATURE:
<223> OTHER INFORMATION: Synthetic primer

<400> SEQUENCE: 37
ggtggtggag gtggcggcgg aggtattgag ggcccaaccc ttcgccaatg gcttgcagca    60
cgcgca    66

<210> SEQ ID NO 38
<211> LENGTH: 76
<212> TYPE: DNA
<213> ORGANISM: Artificial Sequence
<220> FEATURE:
<223> OTHER INFORMATION: Synthetic primer

<400> SEQUENCE: 38
aaaaaaagga tcctcgagat tatgcgcgtg ctgcaagcca ttggcgaagg gttgggccct    60
caatacctcc gccgcc    76

<210> SEQ ID NO 39
<211> LENGTH: 126
<212> TYPE: DNA
<213> ORGANISM: Artificial Sequence
<220> FEATURE:
<223> OTHER INFORMATION: Synthetic primer

<400> SEQUENCE: 39
aaaggtggag gtggtggtat cgaaggtccg actctgcgtc agtggctggc tgctcgtgct    60
ggtggtggag gtggcggcgg aggtattgag ggcccaaccc ttcgccaatg gcttgcagca   120
cgcgca   126

<210> SEQ ID NO 40
<211> LENGTH: 124
<212> TYPE: DNA
<213> ORGANISM: Artificial Sequence
<220> FEATURE:
<223> OTHER INFORMATION: Synthetic primer

<400> SEQUENCE: 40
ccaggctgag acgcagtcac cgaccgacga gcacgaccac cacctccacc gccgcctcca    60
taactcccgg gttgggaagc ggttaccgaa cgtcgtgcgc gtattagagc tcctaggaaa   120
aaaa   124

```
<210> SEQ ID NO 41
<211> LENGTH: 42
<212> TYPE: PRT
<213> ORGANISM: Artificial Sequence
<220> FEATURE:
<223> OTHER INFORMATION: Synthetic peptide

<400> SEQUENCE: 41

Lys Gly Gly Gly Gly Gly Ile Glu Gly Pro Thr Leu Arg Gln Trp Leu
 1               5                  10                  15

Ala Ala Arg Ala Gly Gly Gly Gly Gly Gly Ile Glu Gly Pro
            20                  25                  30

Thr Leu Arg Gln Trp Leu Ala Ala Arg Ala
        35                  40

<210> SEQ ID NO 42
<211> LENGTH: 22
<212> TYPE: DNA
<213> ORGANISM: Artificial Sequence
<220> FEATURE:
<223> OTHER INFORMATION: Synthetic primer

<400> SEQUENCE: 42
aacataagta cctgtaggat cg                                           22

<210> SEQ ID NO 43
<211> LENGTH: 52
<212> TYPE: DNA
<213> ORGANISM: Artificial Sequence
<220> FEATURE:
<223> OTHER INFORMATION: Synthetic primer

<400> SEQUENCE: 43
ttcgatacca ccacctccac ctttacccgg agacagggag aggctcttct gc          52

<210> SEQ ID NO 44
<211> LENGTH: 861
<212> TYPE: DNA
<213> ORGANISM: Homo sapiens

<400> SEQUENCE: 44
tctagatttg ttttaactaa ttaaaggagg aataacatat ggacaaaact cacacatgtc   60
caccttgtcc agctccggaa ctcctggggg gaccgtcagt cttcctcttc ccccaaaac   120 ccaaggacac cctcatgatc tcccggaccc ctgaggtcac atgcgtggtg gtggacgtga  180
gccacgaaga ccctgaggtc aagttcaact ggtacgtgga cggcgtggag gtgcataatg  240
ccaagacaaa gccgcgggag gagcagtaca acagcacgta ccgtgtggtc agcgtcctca  300
ccgtcctgca ccaggactgg ctgaatggca aggagtacaa gtgcaaggtc tccaacaaag  360
ccctcccagc ccccatcgag aaaaccatct ccaaagccaa agggcagccc cgagaaccac  420
aggtgtacac cctgccccca tcccgggatg agctgaccaa gaaccaggtc agcctgacct  480
gcctggtcaa aggcttctat cccagcgaca tcgccgtgga gtgggagagc aatgggcagc  540
cggagaacaa ctacaagacc acgcctcccg tgctggactc cgacggctcc ttcttcctct  600
acagcaagct caccgtggac aagagcaggt ggcagcaggg gaacgtcttc tcatgctccg  660
tgatgcatga ggctctgcac aaccactaca cgcagaagag cctctccctg tctccgggta  720
aaggtggagg tggtggtatc gaaggtccga ctctgcgtca gtggctggct gctcgtgctg  780
gtggtggagg tggcggcgga ggtattgagg gcccaaccct tcgccaatgg cttgcagcac  840
gcgcataatc tcgaggatcc g                                            861
```

<210> SEQ ID NO 45
<211> LENGTH: 861
<212> TYPE: DNA
<213> ORGANISM: Homo sapiens

<400> SEQUENCE: 45

```
agatctaaac aaaattgatt aatttcctcc ttattgtata cctgttttga gtgtgtacag    60
gtggaacagg tcgaggcctt gaggaccccc ctggcagtca aaggagaag ggggttttg    120
ggttcctgtg ggagtactag agggcctggg gactccagtg tacgcaccac cacctgcact   180
cggtgcttct gggactccag ttcaagttga ccatgcacct gccgcacctc cacgtattac   240
ggttctgttt cggcgccctc ctcgtcatgt tgtcgtgcat ggcacaccag tcgcaggagt   300
ggcaggacgt ggtcctgacc gacttaccgt tcctcatgtt cacgttccag aggttgtttc   360
gggagggtcg ggggtagctc ttttggtaga ggtttcggtt tcccgtcggg gctcttggtg   420
tccacatgtg gacgggggt agggccctac tcgactggtt cttggtccag tcggactgga   480
cggaccagtt tccgaagata gggtcgctgt agcggcacct caccctctcg ttacccgtcg   540
gcctcttgtt gatgttctgg tgcggagggc acgacctgag gctgccgagg aagaaggaga   600
tgtcgttcga gtggcacctg ttctcgtcca ccgtcgtccc cttgcagaag agtacgaggc   660
actacgtact ccgagacgtg ttggtgatgt gcgtcttctc ggagagggac agaggcccat   720
ttccacctcc accaccatag cttccaggct gagacgcagt caccgaccga cgagcacgac   780
caccacctcc accgccgcct ccataactcc cgggttggga agcggttacc gaacgtcgtg   840
cgcgtattag agctcctagg c                                              861
```

<210> SEQ ID NO 46
<211> LENGTH: 269
<212> TYPE: PRT
<213> ORGANISM: Artificial Sequence
<220> FEATURE:
<223> OTHER INFORMATION: Synthetic peptide

<400> SEQUENCE: 46

```
Met Asp Lys Thr His Thr Cys Pro Pro Cys Pro Ala Pro Glu Leu Leu
 1               5                  10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175
```

```
Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Gly Gly Gly Ile Glu Gly Pro Thr Leu Arg
225                 230                 235                 240

Gln Trp Leu Ala Ala Arg Ala Gly Gly Gly Gly Gly Gly Ile
                245                 250                 255

Glu Gly Pro Thr Leu Arg Gln Trp Leu Ala Ala Arg Ala
            260                 265

<210> SEQ ID NO 47
<211> LENGTH: 9
<212> TYPE: PRT
<213> ORGANISM: Artificial Sequence
<220> FEATURE:
<223> OTHER INFORMATION: Synthetic peptide

<400> SEQUENCE: 47

Glu Gly Pro Thr Leu Arg Gln Trp Leu
 1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is selected from the group consisting of
      Glu, Asp, Lys, and Val
<220> FEATURE:
<221> NAME/KEY: MISC_FEATURE
<222> LOCATION: (2)..(2)
<223> OTHER INFORMATION: Xaa is selected from the group consisting of
      Gly and Ala
<220> FEATURE:
<221> NAME/KEY: MISC_FEATURE
<222> LOCATION: (3)..(3)
<223> OTHER INFORMATION: Xaa is Pro
<220> FEATURE:
<221> NAME/KEY: MISC_FEATURE
<222> LOCATION: (4)..(4)
<223> OTHER INFORMATION: Xaa is selected from the group consisting of
      Thr and Ser
<220> FEATURE:
<221> NAME/KEY: MISC_FEATURE
<222> LOCATION: (5)..(5)
<223> OTHER INFORMATION: Xaa is selected from the group consisting of
      Leu, Ile, Val, Ala, and Phe
<220> FEATURE:
<221> NAME/KEY: MISC_FEATURE
<222> LOCATION: (6)..(6)
<223> OTHER INFORMATION: Xaa is selected from the group consisting of
      Arg and Lys
<220> FEATURE:
<221> NAME/KEY: MISC_FEATURE
<222> LOCATION: (7)..(7)
<223> OTHER INFORMATION: Xaa is selected from the group consisting of
      Gln, Asn, Glu
<220> FEATURE:
<221> NAME/KEY: MISC_FEATURE
<222> LOCATION: (8)..(8)
<223> OTHER INFORMATION: Xaa is selected from the group consisting of
      Trp, Tyr, and Phe
<220> FEATURE:
<221> NAME/KEY: MISC_FEATURE
```

```
<222> LOCATION: (9)..(9)
<223> OTHER INFORMATION: Xaa is selected from the group consisting of
      Leu, Ile, Val, Ala, Phe, Met and Lys

<400> SEQUENCE: 48

Xaa Xaa Xaa Xaa Xaa Xaa Xaa Xaa Xaa
 1               5

<210> SEQ ID NO 49
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is selected from the group consisting of
      Ile, Ala, Val, Leu, Ser and Arg
<220> FEATURE:
<221> NAME/KEY: MISC_FEATURE
<222> LOCATION: (2)..(2)
<223> OTHER INFORMATION: Xaa is selected from the group consisting of
      Glu, Asp, Lys, and Val
<220> FEATURE:
<221> NAME/KEY: MISC_FEATURE
<222> LOCATION: (3)..(3)
<223> OTHER INFORMATION: Xaa is selected from the group consisting of
      Gly and Ala
<220> FEATURE:
<221> NAME/KEY: MISC_FEATURE
<222> LOCATION: (4)..(4)
<223> OTHER INFORMATION: Xaa is Pro
<220> FEATURE:
<221> NAME/KEY: MISC_FEATURE
<222> LOCATION: (5)..(5)
<223> OTHER INFORMATION: Xaa is selected from the group consisting of
      Thr and Ser
<220> FEATURE:
<221> NAME/KEY: MISC_FEATURE
<222> LOCATION: (6)..(6)
<223> OTHER INFORMATION: Xaa is selected from the group consisting of
      Leu, Ile, Val, Ala and Phe
<220> FEATURE:
<221> NAME/KEY: MISC_FEATURE
<222> LOCATION: (7)..(7)
<223> OTHER INFORMATION: Xaa is selected from the group consisting of
      Arg and Lys
<220> FEATURE:
<221> NAME/KEY: MISC_FEATURE
<222> LOCATION: (8)..(8)
<223> OTHER INFORMATION: Xaa is selected from the group consisting of
      Gln, Asn and Glu
<220> FEATURE:
<221> NAME/KEY: MISC_FEATURE
<222> LOCATION: (9)..(9)
<223> OTHER INFORMATION: Xaa is selected from the group consisting of
      Trp, Tyr and Phe
<220> FEATURE:
<221> NAME/KEY: MISC_FEATURE
<222> LOCATION: (10)..(10)
<223> OTHER INFORMATION: Xaa is selected from the group consisting of
      Leu, Ile, Val, Ala, Phe, Met and Lys
<220> FEATURE:
<221> NAME/KEY: MISC_FEATURE
<222> LOCATION: (11)..(11)
<223> OTHER INFORMATION: Xaa is selected from the group consisting of
      Ala, Ile, Val, Leu, Phe, Ser, Thr, Lys, His and Glu
<220> FEATURE:
<221> NAME/KEY: MISC_FEATURE
<222> LOCATION: (12)..(12)
<223> OTHER INFORMATION: Xaa is selected from the group consisting of
      Ala, Ile, Val, Leu, Phe, Gly, Ser and Gln
<220> FEATURE:
<221> NAME/KEY: MISC_FEATURE
<222> LOCATION: (13)..(13)
<223> OTHER INFORMATION: Xaa is selected from the group consisting of
      Arg, Lys, Thr, Val, Asn, Gln and Gly
```

```
<220> FEATURE:
<221> NAME/KEY: MISC_FEATURE
<222> LOCATION: (14)..(14)
<223> OTHER INFORMATION: Xaa is selected from the group consisting of
      Ala, Ile, Val, Leu, Phe, Thr, Arg, Glu and Gly

<400> SEQUENCE: 49

Xaa Xaa Xaa Xaa Xaa Xaa Xaa Xaa Xaa Xaa Xaa Xaa Xaa Xaa
 1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Xaa is selected from the group consisting of
      Glu, Asp, Lys, and Val
<220> FEATURE:
<221> NAME/KEY: MOD_RES
<222> LOCATION: (2)..(2)
<223> OTHER INFORMATION: Xaa is selected from the group consisting of
      Gly and Ala
<220> FEATURE:
<221> NAME/KEY: MOD_RES
<222> LOCATION: (3)..(3)
<223> OTHER INFORMATION: Xaa is Pro
<220> FEATURE:
<221> NAME/KEY: MOD_RES
<222> LOCATION: (4)..(4)
<223> OTHER INFORMATION: Xaa is selected from the group consisting of
      Thr and Ser
<220> FEATURE:
<221> NAME/KEY: MOD_RES
<222> LOCATION: (5)..(5)
<223> OTHER INFORMATION: Xaa is selected from the group consisting of
      Leu, Ile, Val, Ala and Phe
<220> FEATURE:
<221> NAME/KEY: MOD_RES
<222> LOCATION: (6)..(6)
<223> OTHER INFORMATION: Xaa is selected from the group consisting of
      Arg and Lys
<220> FEATURE:
<221> NAME/KEY: MOD_RES
<222> LOCATION: (7)..(7)
<223> OTHER INFORMATION: Xaa is selected from the group consisting of
      Gln, Asn and Glu
<220> FEATURE:
<221> NAME/KEY: MOD_RES
<222> LOCATION: (8)..(8)
<223> OTHER INFORMATION: Xaa is selected from the group consisting of
      Trp, Tyr and Phe
<220> FEATURE:
<221> NAME/KEY: MOD_RES
<222> LOCATION: (9)..(9)
<223> OTHER INFORMATION: Xaa is selected from the group consisting of
      Leu, Ile, Val, Ala, Phe, Met and Lys
<220> FEATURE:
<221> NAME/KEY: MOD_RES
<222> LOCATION: (10)..(10)
<223> OTHER INFORMATION: Xaa is selected from the group consisting of
      Ala, Ile, Val, Leu, Phe, Ser, Thr, Lys, His and Glu

<400> SEQUENCE: 50

Xaa Xaa Xaa Xaa Xaa Xaa Xaa Xaa Xaa Xaa
 1               5                   10

<210> SEQ ID NO 51
<211> LENGTH: 11
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: MOD_RES
<222> LOCATION: (1)..(1)
<223> OTHER INFORMATION: Xaa is selected from the group consisting of
      Glu, Asp, Lys, and Val
<220> FEATURE:
<221> NAME/KEY: MOD_RES
<222> LOCATION: (2)..(2)
<223> OTHER INFORMATION: Xaa is selected from the group consisting of
      Gly and Ala
<220> FEATURE:
<221> NAME/KEY: MOD_RES
<222> LOCATION: (3)..(3)
<223> OTHER INFORMATION: Xaa is Pro
<220> FEATURE:
<221> NAME/KEY: MOD_RES
<222> LOCATION: (4)..(4)
<223> OTHER INFORMATION: Xaa is selected from the group consisting of
      Thr and Ser
<220> FEATURE:
<221> NAME/KEY: MOD_RES
<222> LOCATION: (5)..(5)
<223> OTHER INFORMATION: Xaa is selected from the group consisting of
      Leu, Ile, Val, Ala and Phe
<220> FEATURE:
<221> NAME/KEY: MOD_RES
<222> LOCATION: (6)..(6)
<223> OTHER INFORMATION: Xaa is selected from the group consisting of
      Arg and Lys
<220> FEATURE:
<221> NAME/KEY: MOD_RES
<222> LOCATION: (7)..(7)
<223> OTHER INFORMATION: Xaa is selected from the group consisting of
      Gln, Asn and Glu
<220> FEATURE:
<221> NAME/KEY: MOD_RES
<222> LOCATION: (8)..(8)
<223> OTHER INFORMATION: Xaa is selected from the group consisting of
      Trp, Tyr and Phe
<220> FEATURE:
<221> NAME/KEY: MOD_RES
<222> LOCATION: (9)..(9)
<223> OTHER INFORMATION: Xaa is selected from the group consisting of
      Leu, Ile, Val, Ala, Phe, Met and Lys
<220> FEATURE:
<221> NAME/KEY: MOD_RES
<222> LOCATION: (10)..(10)
<223> OTHER INFORMATION: Xaa is selected from the group consisting of
      Ala, Ile, Val, Leu, Phe, Ser, Thr, Lys, His and Glu
<220> FEATURE:
<221> NAME/KEY: MOD_RES
<222> LOCATION: (11)..(11)
<223> OTHER INFORMATION: Xaa is selected from the group consisting of
      Ala, Ile, Val, Leu, Phe, Gly, Ser and Gln

<400> SEQUENCE: 51

Xaa Xaa Xaa Xaa Xaa Xaa Xaa Xaa Xaa Xaa Xaa
 1               5                  10

<210> SEQ ID NO 52
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Xaa is selected from the group consisting of
      Glu, Asp, Lys, and Val
<220> FEATURE:
<221> NAME/KEY: MOD_RES
<222> LOCATION: (2)..(2)
<223> OTHER INFORMATION: Xaa is selected from the group consisting of
      Gly and Ala
<220> FEATURE:
<221> NAME/KEY: MOD_RES
<222> LOCATION: (3)..(3)
```

```
<223> OTHER INFORMATION: Xaa is Pro
<220> FEATURE:
<221> NAME/KEY: MOD_RES
<222> LOCATION: (4)..(4)
<223> OTHER INFORMATION: Xaa is selected from the group consisting of
      Thr and Ser
<220> FEATURE:
<221> NAME/KEY: MOD_RES
<222> LOCATION: (5)..(5)
<223> OTHER INFORMATION: Xaa is selected from the group consisting of
      Leu, Ile, Val, Ala and Phe
<220> FEATURE:
<221> NAME/KEY: MOD_RES
<222> LOCATION: (6)..(6)
<223> OTHER INFORMATION: Xaa is selected from the group consisting of
      Arg and Lys
<220> FEATURE:
<221> NAME/KEY: MOD_RES
<222> LOCATION: (7)..(7)
<223> OTHER INFORMATION: Xaa is selected from the group consisting of
      Gln, Asn and Glu
<220> FEATURE:
<221> NAME/KEY: MOD_RES
<222> LOCATION: (8)..(8)
<223> OTHER INFORMATION: Xaa is selected from the group consisting of
      Trp, Tyr and Phe
<220> FEATURE:
<221> NAME/KEY: MOD_RES
<222> LOCATION: (9)..(9)
<223> OTHER INFORMATION: Xaa is selected from the group consisting of
      Leu, Ile, Val, Ala, Phe, Met and Lys
<220> FEATURE:
<221> NAME/KEY: MOD_RES
<222> LOCATION: (10)..(10)
<223> OTHER INFORMATION: Xaa is selected from the group consisting of
      Ala, Ile, Val, Leu, Phe, Ser, Thr, Lys, His and Glu
<220> FEATURE:
<221> NAME/KEY: MOD_RES
<222> LOCATION: (11)..(11)
<223> OTHER INFORMATION: Xaa is selected from the group consisting of
      Ala, Ile, Val, Leu, Phe, Gly, Ser and Gln
<220> FEATURE:
<221> NAME/KEY: misc_feature
<222> LOCATION: (12)..(12)
<223> OTHER INFORMATION: Xaa can be any naturally occurring amino acid

<400> SEQUENCE: 52

Xaa Xaa Xaa Xaa Xaa Xaa Xaa Xaa Xaa Xaa Xaa Xaa
 1               5                  10

<210> SEQ ID NO 53
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Xaa is selected from the group consisting of
      Glu, Asp, Lys, and Val
<220> FEATURE:
<221> NAME/KEY: MOD_RES
<222> LOCATION: (2)..(2)
<223> OTHER INFORMATION: Xaa is selected from the group consisting of
      Gly and Ala
<220> FEATURE:
<221> NAME/KEY: MOD_RES
<222> LOCATION: (3)..(3)
<223> OTHER INFORMATION: Xaa is Pro
<220> FEATURE:
<221> NAME/KEY: MOD_RES
<222> LOCATION: (4)..(4)
<223> OTHER INFORMATION: Xaa is selected from the group consisting of
      Thr and Ser
<220> FEATURE:
<221> NAME/KEY: MOD_RES
<222> LOCATION: (5)..(5)
```

<223> OTHER INFORMATION: Xaa is selected from the group consisting of
      Leu, Ile, Val, Ala and Phe
<220> FEATURE:
<221> NAME/KEY: MOD_RES
<222> LOCATION: (6)..(6)
<223> OTHER INFORMATION: Xaa is selected from the group consisting of
      Arg and Lys
<220> FEATURE:
<221> NAME/KEY: MOD_RES
<222> LOCATION: (7)..(7)
<223> OTHER INFORMATION: Xaa is selected from the group consisting of
      Gln, Asn and Glu
<220> FEATURE:
<221> NAME/KEY: MOD_RES
<222> LOCATION: (8)..(8)
<223> OTHER INFORMATION: Xaa is selected from the group consisting of
      Trp, Tyr and Phe
<220> FEATURE:
<221> NAME/KEY: MOD_RES
<222> LOCATION: (9)..(9)
<223> OTHER INFORMATION: Xaa is selected from the group consisting of
      Leu, Ile, Val, Ala, Phe, Met and Lys
<220> FEATURE:
<221> NAME/KEY: MOD_RES
<222> LOCATION: (10)..(10)
<223> OTHER INFORMATION: Xaa is selected from the group consisting of
      Ala, Ile, Val, Leu, Phe, Ser, Thr, Lys, His and Glu
<220> FEATURE:
<221> NAME/KEY: MOD_RES
<222> LOCATION: (11)..(11)
<223> OTHER INFORMATION: Xaa is selected from the group consisting of
      Ala, Ile, Val, Leu, Phe, Gly, Ser and Gln
<220> FEATURE:
<221> NAME/KEY: MOD_RES
<222> LOCATION: (12)..(12)
<223> OTHER INFORMATION: Xaa is selected from the group consisting of
      Arg, Lys, Thr, Val, Asn, Gln and Gly
<220> FEATURE:
<221> NAME/KEY: MOD_RES
<222> LOCATION: (13)..(13)
<223> OTHER INFORMATION: Xaa is selected from the group consisting of
      Ala, Ile, Val, Leu, Phe, Thr, Arg, Glu and Gly

<400> SEQUENCE: 53

Xaa Xaa Xaa Xaa Xaa Xaa Xaa Xaa Xaa Xaa Xaa Xaa Xaa
 1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Xaa is selected from the group consisting of
      Ile, Ala, Val, Leu, Ser and Arg
<220> FEATURE:
<221> NAME/KEY: MOD_RES
<222> LOCATION: (2)..(2)
<223> OTHER INFORMATION: Xaa is selected from the group consisting of
      Glu, Asp, Lys, and Val
<220> FEATURE:
<221> NAME/KEY: MOD_RES
<222> LOCATION: (3)..(3)
<223> OTHER INFORMATION: Xaa is selected from the group consisting of
      Gly and Ala
<220> FEATURE:
<221> NAME/KEY: MOD_RES
<222> LOCATION: (4)..(4)
<223> OTHER INFORMATION: Xaa is Pro
<220> FEATURE:
<221> NAME/KEY: MOD_RES
<222> LOCATION: (5)..(5)
<223> OTHER INFORMATION: Xaa is selected from the group consisting of
      Thr and Ser
<220> FEATURE:

```
<221> NAME/KEY: MOD_RES
<222> LOCATION: (6)..(6)
<223> OTHER INFORMATION: Xaa is selected from the group consisting of
      Leu, Ile, Val, Ala and Phe
<220> FEATURE:
<221> NAME/KEY: MOD_RES
<222> LOCATION: (7)..(7)
<223> OTHER INFORMATION: Xaa is selected from the group consisting of
      Arg and Lys
<220> FEATURE:
<221> NAME/KEY: MOD_RES
<222> LOCATION: (8)..(8)
<223> OTHER INFORMATION: Xaa is selected from the group consisting of
      Gln, Asn and Glu
<220> FEATURE:
<221> NAME/KEY: MOD_RES
<222> LOCATION: (9)..(9)
<223> OTHER INFORMATION: Xaa is selected from the group consisting of
      Trp, Tyr and Phe
<220> FEATURE:
<221> NAME/KEY: MOD_RES
<222> LOCATION: (10)..(10)
<223> OTHER INFORMATION: Xaa is selected from the group consisting of
      Leu, Ile, Val, Ala, Phe, Met and Lys

<400> SEQUENCE: 54

Xaa Xaa Xaa Xaa Xaa Xaa Xaa Xaa Xaa Xaa
 1               5                  10

<210> SEQ ID NO 55
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Xaa is selected from the group consisting of
      Ile, Ala, Val, Leu, Ser and Arg
<220> FEATURE:
<221> NAME/KEY: MOD_RES
<222> LOCATION: (2)..(2)
<223> OTHER INFORMATION: Xaa is selected from the group consisting of
      Glu, Asp, Lys, and Val
<220> FEATURE:
<221> NAME/KEY: MOD_RES
<222> LOCATION: (3)..(3)
<223> OTHER INFORMATION: Xaa is selected from the group consisting of
      Gly and Ala
<220> FEATURE:
<221> NAME/KEY: MOD_RES
<222> LOCATION: (4)..(4)
<223> OTHER INFORMATION: Xaa is Pro
<220> FEATURE:
<221> NAME/KEY: MOD_RES
<222> LOCATION: (5)..(5)
<223> OTHER INFORMATION: Xaa is selected from the group consisting of
      Thr and Ser
<220> FEATURE:
<221> NAME/KEY: MOD_RES
<222> LOCATION: (6)..(6)
<223> OTHER INFORMATION: Xaa is selected from the group consisting of
      Leu, Ile, Val, Ala and Phe
<220> FEATURE:
<221> NAME/KEY: MOD_RES
<222> LOCATION: (7)..(7)
<223> OTHER INFORMATION: Xaa is selected from the group consisting of
      Arg and Lys
<220> FEATURE:
<221> NAME/KEY: MOD_RES
<222> LOCATION: (8)..(8)
<223> OTHER INFORMATION: Xaa is selected from the group consisting of
      Gln, Asn and Glu
<220> FEATURE:
<221> NAME/KEY: MOD_RES
<222> LOCATION: (9)..(9)
<223> OTHER INFORMATION: Xaa is selected from the group consisting of
```

```
      Trp, Tyr and Phe
<220> FEATURE:
<221> NAME/KEY: MOD_RES
<222> LOCATION: (10)..(10)
<223> OTHER INFORMATION: Xaa is selected from the group consisting of
      Leu, Ile, Val, Ala, Phe, Met and Lys
<220> FEATURE:
<221> NAME/KEY: MOD_RES
<222> LOCATION: (11)..(11)
<223> OTHER INFORMATION: Xaa is selected from the group consisting of
      Ala, Ile, Val, Leu, Phe, Ser, Thr, Lys, His and Glu

<400> SEQUENCE: 55

Xaa Xaa Xaa Xaa Xaa Xaa Xaa Xaa Xaa Xaa Xaa
 1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Xaa is selected from the group consisting of
      Ile, Ala, Val, Leu, Ser and Arg
<220> FEATURE:
<221> NAME/KEY: MOD_RES
<222> LOCATION: (2)..(2)
<223> OTHER INFORMATION: Xaa is selected from the group consisting of
      Glu, Asp, Lys, and Val
<220> FEATURE:
<221> NAME/KEY: MOD_RES
<222> LOCATION: (3)..(3)
<223> OTHER INFORMATION: Xaa is selected from the group consisting of
      Gly and Ala
<220> FEATURE:
<221> NAME/KEY: MOD_RES
<222> LOCATION: (4)..(4)
<223> OTHER INFORMATION: Xaa is Pro
<220> FEATURE:
<221> NAME/KEY: MOD_RES
<222> LOCATION: (5)..(5)
<223> OTHER INFORMATION: Xaa is selected from the group consisting of
      Thr and Ser
<220> FEATURE:
<221> NAME/KEY: MOD_RES
<222> LOCATION: (6)..(6)
<223> OTHER INFORMATION: Xaa is selected from the group consisting of
      Leu, Ile, Val, Ala and Phe
<220> FEATURE:
<221> NAME/KEY: MOD_RES
<222> LOCATION: (7)..(7)
<223> OTHER INFORMATION: Xaa is selected from the group consisting of
      Arg and Lys
<220> FEATURE:
<221> NAME/KEY: MOD_RES
<222> LOCATION: (8)..(8)
<223> OTHER INFORMATION: Xaa is selected from the group consisting of
      Gln, Asn and Glu
<220> FEATURE:
<221> NAME/KEY: MOD_RES
<222> LOCATION: (9)..(9)
<223> OTHER INFORMATION: Xaa is selected from the group consisting of
      Trp, Tyr and Phe
<220> FEATURE:
<221> NAME/KEY: MOD_RES
<222> LOCATION: (10)..(10)
<223> OTHER INFORMATION: Xaa is selected from the group consisting of
      Leu, Ile, Val, Ala, Phe, Met and Lys
<220> FEATURE:
<221> NAME/KEY: MOD_RES
<222> LOCATION: (11)..(11)
<223> OTHER INFORMATION: Xaa is selected from the group consisting of
      Ala, Ile, Val, Leu, Phe, Ser, Thr, Lys, His and Glu
<220> FEATURE:
<221> NAME/KEY: MOD_RES
```

```
<222> LOCATION: (12)..(12)
<223> OTHER INFORMATION: Xaa is selected from the group consisting of
      Ala, Ile, Val, Leu, Phe, Gly, Ser and Gln

<400> SEQUENCE: 56

Xaa Xaa Xaa Xaa Xaa Xaa Xaa Xaa Xaa Xaa Xaa Xaa
 1               5                  10

<210> SEQ ID NO 57
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Xaa is selected from the group consisting of
      Ile, Ala, Val, Leu, Ser and Arg
<220> FEATURE:
<221> NAME/KEY: MOD_RES
<222> LOCATION: (2)..(2)
<223> OTHER INFORMATION: Xaa is selected from the group consisting of
      Glu, Asp, Lys, and Val
<220> FEATURE:
<221> NAME/KEY: MOD_RES
<222> LOCATION: (3)..(3)
<223> OTHER INFORMATION: Xaa is selected from the group consisting of
      Gly and Ala
<220> FEATURE:
<221> NAME/KEY: MOD_RES
<222> LOCATION: (4)..(4)
<223> OTHER INFORMATION: Xaa is Pro
<220> FEATURE:
<221> NAME/KEY: MOD_RES
<222> LOCATION: (5)..(5)
<223> OTHER INFORMATION: Xaa is selected from the group consisting of
      Thr and Ser
<220> FEATURE:
<221> NAME/KEY: MOD_RES
<222> LOCATION: (6)..(6)
<223> OTHER INFORMATION: Xaa is selected from the group consisting of
      Leu, Ile, Val, Ala and Phe
<220> FEATURE:
<221> NAME/KEY: MOD_RES
<222> LOCATION: (7)..(7)
<223> OTHER INFORMATION: Xaa is selected from the group consisting of
      Arg and Lys
<220> FEATURE:
<221> NAME/KEY: MOD_RES
<222> LOCATION: (8)..(8)
<223> OTHER INFORMATION: Xaa is selected from the group consisting of
      Gln, Asn and Glu
<220> FEATURE:
<221> NAME/KEY: MOD_RES
<222> LOCATION: (9)..(9)
<223> OTHER INFORMATION: Xaa is selected from the group consisting of
      Trp, Tyr and Phe
<220> FEATURE:
<221> NAME/KEY: MOD_RES
<222> LOCATION: (10)..(10)
<223> OTHER INFORMATION: Xaa is selected from the group consisting of
      Leu, Ile, Val, Ala, Phe, Met and Lys
<220> FEATURE:
<221> NAME/KEY: MOD_RES
<222> LOCATION: (11)..(11)
<223> OTHER INFORMATION: Xaa is selected from the group consisting of
      Ala, Ile, Val, Leu, Phe, Ser, Thr, Lys, His and Glu
<220> FEATURE:
<221> NAME/KEY: MOD_RES
<222> LOCATION: (12)..(12)
<223> OTHER INFORMATION: Xaa is selected from the group consisting of
      Ala, Ile, Val, Leu, Phe, Gly, Ser and Gln
<220> FEATURE:
<221> NAME/KEY: MOD_RES
<222> LOCATION: (13)..(13)
<223> OTHER INFORMATION: Xaa is selected from the group consisting of
      Arg, Lys, Thr, Val, Asn, Gln and Gly
```

```
<400> SEQUENCE: 57

Xaa Xaa Xaa Xaa Xaa Xaa Xaa Xaa Xaa Xaa Xaa Xaa Xaa
 1               5                  10

<210> SEQ ID NO 58
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 58

Gly Gly Gly Gly Gly Gly Gly Gly
 1               5
```

The embodiments of the invention in which an exclusive property or privilege is claimed are defined as follows:

1. A method of producing a compound comprising growing a host cell comprising a polynucleotide that encodes said compound in a suitable nutrient medium and isolating said compound from said cell or nutrient medium, wherein said compound binds to an mpl receptor and comprises the structure $$TMP_1\text{-}(L_1)_n\text{-}TMP_2$$

wherein the C-terminus of the $TMP_1$ peptide is linked to the N-terminus of the $TMP_2$ peptide, optionally via $L_1$, wherein $TMP_1$ and $TMP_2$ are each independently selected from the group of core compounds comprising the structure selected from the group consisting of:

a) $X_2\text{-}X_3\text{-}X_4\text{-}X_5\text{-}X_6\text{-}X_7\text{-}X_8\text{-}X_9\text{-}X_{10}$,
wherein,
$X_2$ is selected from the group consisting of Glu, Lys, and Val;
$X_3$ is selected from the group consisting of Gly and Ala;
$X_4$ is Pro;
$X_5$ is selected from the group consisting of Thr and Ser;
$X_6$ is selected from the group consisting of Leu, Ile, Val, Ala, and Phe;
$X_7$ is selected from the group consisting of Arg and Lys;
$X_8$ is selected from the group consisting of Gln, Asn, and Glu;
$X_9$ is selected from the group consisting of Trp, Tyr, Cys, Ala, and Phe;
$X_{10}$ is selected from the group consisting of Leu, Ile, Val, Ala, Phe, Met, and Lys;

b) $X_2\text{-}X_3\text{-}X_4\text{-}X_5\text{-}X_6\text{-}X_7\text{-}X_8\text{-}X_9\text{-}X_{10}$,
wherein,
$X_2$ is selected from the group consisting of Glu, Asp, Lys, and Val;
$X_3$ is Ala;
$X_4$ is Pro;
$X_5$ is selected from the group consisting of Thr and Ser;
$X_6$ is selected from the group consisting of Leu, Ile, Val, Ala, and Phe;
$X_7$ is selected from the group consisting of Arg and Lys;
$X_8$ is selected from the group consisting of Gln, Asn, and Glu;
$X_9$ is selected from the group consisting of Trp, Tyr, Cys, Ala, and Phe;
$X_{10}$ is selected from the group consisting of Leu, Ile, Val, Ala, Phe, Met, and Lys;

c) $X_2\text{-}X_3\text{-}X_4\text{-}X_5\text{-}X_6\text{-}X_7\text{-}X_8\text{-}X_9\text{-}X_{10}$,
wherein,
$X_2$ is selected from the group consisting of Glu, Asp, Lys, and Val;
$X_3$ is selected from the group consisting of Gly and Ala;
$X_4$ is Pro;
$X_5$ is Ser;
$X_6$ is selected from the group consisting of Leu, Ile, Val, Ala, and Phe;
$X_7$ is selected from the group consisting of Arg and Lys;
$X_8$ is selected from the group consisting of Gln, Asn, and Glu;
$X_9$ is selected from the group consisting of Trp, Tyr, Cys, Ala, and Phe;
$X_{10}$ is selected from the group consisting of Leu, Ile, Val, Ala, Phe, Met, and Lys;

d) $X_2\text{-}X_3\text{-}X_4\text{-}X_5\text{-}X_6\text{-}X_7\text{-}X_8\text{-}X_9\text{-}X_{10}$,
wherein,
$X_2$ is selected from the group consisting of Glu, Asp, Lys, and Val;
$X_3$ is selected from the group consisting of Gly and Ala;
$X_4$ is Pro;
$X_5$ is selected from the group consisting of Thr and Ser;
$X_6$ is selected from the group consisting of Ile, Val, Ala, and Phe;
$X_7$ is selected from the group consisting of Arg and Lys;
$X_8$ is selected from the group consisting of Gln, Asn, and Glu;
$X_9$ is selected from the group consisting of Trp, Tyr, Cys, Ala, and Phe;
$X_{10}$ is selected from the group consisting of Leu, Ile, Val, Ala, Phe, Met, and Lys;

e) $X_2\text{-}X_3\text{-}X_4\text{-}X_5\text{-}X_6\text{-}X_7\text{-}X_8\text{-}X_9\text{-}X_{10}$,
wherein,
$X_2$ is selected from the group consisting of Glu, Asp, Lys, and Val;
$X_3$ is selected from the group consisting of Gly and Ala;
$X_4$ is Pro;
$X_5$ is selected from the group consisting of Thr and Ser;
$X_6$ is selected from the group consisting of Leu, Ile, Val, Ala, and Phe;
$X_7$ is Lys;
$X_8$ is selected from the group consisting of Gln, Asn, and Glu;
$X_9$ is selected from the group consisting of Trp, Tyr, Cys, Ala, and Phe;
$X_{10}$ is selected from the group consisting of Leu, Ile, Val, Ala, Phe, Met, and Lys;

f) $X_2$-$X_3$-$X_4$-$X_5$-$X_6$-$X_7$-$X_8$-$X_9$-$X_{10}$,
wherein,
$X_2$ is selected from the group consisting of Glu, Asp, Lys, and Val;
$X_3$ is selected from the group consisting of Gly and Ala;
$X_4$ is Pro;
$X_5$ is selected from the group consisting of Thr and Ser;
$X_6$ is selected from the group consisting of Leu, Ile, Val, Ala, and Phe;
$X_7$ is selected from the group consisting of Arg and Lys;
$X_8$ is selected from the group consisting of Gln and Asn;
$X_9$ is selected from the group consisting of Trp, Tyr, Cys, Ala, and Phe;
$X_{10}$ is selected from the group consisting of Leu, Ile, Val, Ala, Phe, Met, and Lys;
g) $X_2$-$X_3$-$X_4$-$X_5$-$X_6$-$X_7$-$X_8$-$X_9$-$X_{10}$,
wherein,
$X_2$ is selected from the group consisting of Glu, Asp, Lys, and Val;
$X_3$ is selected from the group consisting of Gly and Ala;
$X_4$ is Pro;
$X_5$ is selected from the group consisting of Thr and Ser;
$X_6$ is selected from the group consisting of Leu, Ile, Val, Ala, and Phe;
$X_7$ is selected from the group consisting of Arg and Lys;
$X_8$ is selected from the group consisting of Gln, Asn, and Glu;
$X_9$ is selected from the group consisting of Tyr, Cys, Ala, and Phe;
$X_{10}$ is selected from the group consisting of Leu, Ile, Val, Ala, Phe, Met, and Lys; and
h) $X_2$-$X_3$-$X_4$-$X_5$-$X_6$-$X_7$-$X_8$-$X_9$-$X_{10}$,
wherein,
$X_2$ is selected from the group consisting of Glu, Asp, Lys, and Val;
$X_3$ is selected from the group consisting of Gly and Ala;
$X_4$ is Pro;
$X_5$ is selected from the group consisting of Thr and Ser;
$X_6$ is selected from the group consisting of Leu, Ile, Val, Ala, and Phe;
$X_7$ is selected from the group consisting of Arg and Lys;
$X_8$ is selected from the group consisting of Gln, Asn, and Glu;
$X_9$ is selected from the group consisting of Trp, Tyr, Cys, Ala, and Phe;
$X_{10}$ is selected from the group consisting of Leu, Val, Ala, Phe, Met, and Lys; and
wherein $L_{1a}$ is a linker; and
n is 0 or 1, wherein when n is 1, $L_1$ is independently selected from the linker groups consisting of $Y_n$, wherein Y is a naturally occurring amino acid or a stereoisomer thereof and n is 1 through 20;
and wherein said compound further comprises the formula $$(Fc)_m\text{-}(L_2)_q\text{-}TMP_1\text{-}(L_1)_n\text{-}TMP_2\text{-}(L_3)_r\text{-}(Fc)_p$$

wherein $L_1$, $L_2$ and $L_3$ are linker groups which are each independently selected from the linker groups consisting of
$Y_n$, wherein Y is a naturally occurring amino acid or a stereoisomer thereof and n is 1 through 20;
$(Gly)_n$, wherein n is 1 through 20, and when n is greater than 1, up to half of the Gly residues may be substituted by another amino acid selected from the remaining 19 natural amino acids or a stereoisomer thereof;
$(Gly)_3Lys(Gly)_4$ (SEQ ID NO: 6);
$(Gly)_3AsnGlySer(Gly)_2$ (SEQ ID NO: 7);
$(Gly)_3Cys(Gly)_4$ (SEQ ID NO: 8);
GlyProAsnGly (SEQ ID NO: 9);
a Cys residue; and
$(CH_2)_n$, wherein n is 1 through 20;
wherein Fc is an Fc region of an immunoglobulin;
and wherein m, p, q and r are each independently selected from the group consisting of 0 and 1, wherein at least one of m or p is 1, and further wherein if m is 0 then q is 0, and if p is 0, then r is 0;
and physiologically acceptable salts thereof.

2. The method according to claim 1 wherein $L_1$, $L_2$ and $L_3$ are each independently selected from the group consisting of $Y_n$, wherein Y is selected a naturally-occurring amino acid or a stereoisomer thereof and n is 1 through 20.

3. The method according to claim 1 wherein $L_1$ comprises $(Gly)_n$, wherein n is 1 through 20, and when n is greater than 1, up to half of the Gly residues may be substituted by another amino acid selected from the remaining 19 natural amino acids or a stereoisomer thereof.

4. The method according to claim 1 wherein $L_1$ comprises $(Gly)_n$, wherein n is 1 through 14.

5. The method according to claim 4 wherein $L_1$ comprises $(Gly)_8$.

6. The method according to claim 5 wherein $L_2$ comprises $(Gly)_5$.

7. The method according to claim 6 wherein said compound comprises SEQ ID NO:34 or SEQ ID NO:46.

8. The method according to claim 1 wherein $L_1$, $L_2$ and $L_3$ are independently selected from the group consisting of
$(Gly)_3Lys(Gly)_4$ (SEQ ID NO: 6);
$(Gly)_3AsnGlySer(Gly)_2$ (SEQ ID NO: 7);
$(Gly)_3Cys(Gly)_4$ (SEQ ID NO: 8); and
GlyProAsnGly (SEQ ID NO: 9).

9. The method according to claim 1 wherein $L_1$, $L_2$, or $L_3$ comprises a Cys residue.

10. The method according to claim 1 wherein $L_1$, $L_2$ or $L_3$ comprises $(CH_2)_n$, wherein n is 1 through 20.

11. The method according to claim 1 wherein said polynucleotide is comprised in a vector.

12. The method according to claim 1 wherein said vector is plasmid pAMG21 deposited at the ATCC under accession number 98113.

13. The method according to claim 1 wherein said host cell is selected from bacteria, yeast, fungi, insect or mammalian cells.

14. The method according to claim 13 wherein said host cell is *E. coli*.

15. The method according to claim 1 wherein said $TMP_1$ and $TMP_2$ are independently selected from the group consisting of:
$X_2$-$X_3$-$X_4$-$X_5$-$X_6$-$X_7$-$X_8$-$X_9$-$X_{10}$-$X_{11}$;
$X_2$-$X_3$-$X_4$-$X_5$-$X_6$-$X_7$-$X_8$-$X_9$-$X_{10}$-$X_{11}$-$X_{12}$;
$X_2$-$X_3$-$X_4$-$X_5$-$X_6$-$X_7$-$X_8$-$X_9$-$X_{10}$-$X_{11}$-$X_{12}$-$X_{13}$;
$X_2$-$X_3$-$X_4$-$X_5$-$X_6$-$X_7$-$X_8$-$X_9$-$X_{10}$-$X_{11}$-$X_{12}$-$X_{13}$-$X_{14}$;
$X_1$-$X_2$-$X_3$-$X_4$-$X_5$-$X_6$-$X_7$-$X_8$-$X_9$-$X_{10}$;
$X_1$-$X_2$-$X_3$-$X_4$-$X_5$-$X_6$-$X_7$-$X_8$-$X_9$-$X_{10}$-$X_{11}$;
$X_1$-$X_2$-$X_3$-$X_4$-$X_5$-$X_6$-$X_7$-$X_8$-$X_9$-$X_{10}$-$X_{11}$-$X_{12}$;
$X_1$-$X_2$-$X_3$-$X_4$-$X_5$-$X_6$-$X_7$-$X_8$-$X_9$-$X_{10}$-$X_{11}$-$X_{12}$-$X_{13}$-; and
$X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$,
wherein $X_2$-$X_{10}$ are as defined and $X_1$ and $X_{11}$-$X_{14}$ are selected from the group consisting of:
a) $X_1$ is selected from the group consisting of Ile, Val, Leu, Ser, and Arg;
$X_{11}$ is selected from the group consisting of Ala, Ile, Val, Leu, Phe, Ser, Thr, Lys, His, and Glu;
$X_{12}$ is selected from the group consisting of Ala, Ile, Val, Leu, Phe, Gly, Ser, and Gln;

$X_{13}$ is selected from the group consisting of Arg, Lys, Thr, Val, Asn, Gln, and Gly; and $X_{14}$ is selected from the group consisting of Ala, Ile, Val, Leu, Phe, Thr, Arg, Glu, and Gly;

b) $X_1$ is selected from the group consisting of Ile, Ala, Val, Leu, Ser, and Arg;

$X_{11}$ is selected from the group consisting of Ala, Ile, Val, Leu, Phe, Thr, Lys, His, and Glu;

$X_{12}$ is selected from the group consisting of Ala, Ile, Val, Leu, Phe, Gly, Ser, and Gln;

$X_{13}$ is selected from the group consisting of Arg, Lys, Thr, Val, Asn, Gln, and Gly; and $X_{14}$ is selected from the group consisting of Ala, Ile, Val, Leu, Phe, Thr, Arg, Glu, and Gly; and c) $X_1$ is selected from the group consisting of Ile, Ala, Val, Leu, Ser, and Arg;

$X_{11}$ is selected from the group consisting of Ala, Ile, Val, Leu, Phe, Ser, Thr, Lys, His, and Glu;

$X_{12}$ is selected from the group consisting of Ala, Ile, Val, Leu, Gly, Ser, and Gln;

$X_{13}$ is selected from the group consisting of Arg, Lys, Thr, Val, Asn, Gln, and Gly; and $X_{14}$ is selected from the group consisting of Ala, Ile, Val, Leu, Phe, Thr, Arg, Glu, and Gly.

16. The method according to claim 15 wherein $L_1$, $L_2$ and $L_3$ are each independently selected from the group consisting of $Y_n$, wherein Y is selected a naturally-occurring amino acid or a stereoisomer thereof and n is 1 through 20.

17. The method according to claim 15 wherein $L_1$ comprises $(Gly)_n$, wherein n is 1 through 20, and when n is greater than 1, up to half of the Gly residues may be substituted by another amino acid selected from the remaining 19 natural amino acids or a stereoisomer thereof.

18. The method according to claim 15 wherein $L_1$ comprises $(Gly)_n$, wherein n is 1 through 14.

19. The method according to claim 18 wherein $L_1$ comprises $(Gly)_8$.

20. The method according to claim 19 wherein $L_2$ comprises $(Gly)_5$.

21. The method according to claim 20 wherein said compound comprises SEQ ID NO:34 or SEQ ID NO:46.

22. The method according to claim 15 wherein $L_1$, $L_2$ and $L_3$ are independently selected from the group consisting of
$(Gly)_3Lys(Gly)_4$ (SEQ ID NO: 6);
$(Gly)_3AsnGlySer(Gly)_2$ (SEQ ID NO: 7);
$(Gly)_3Cys(Gly)_4$ (SEQ ID NO: 8); and
GlyProAsnGly (SEQ ID NO: 9).

23. The method according to claim 15 wherein $L_1$, $L_2$, or $L_3$ comprises a Cys residue.

24. The method according to claim 15 wherein $L_1$, $L_2$ or $L_3$ comprises $(CH_2)_n$, wherein n is 1 through 20.

25. The method according to claim 15 wherein said polynucleotide is comprised in a vector.

26. The method according to claim 15 wherein said vector is plasmid pAMG21deposited at the ATCC under accession number 98113.

27. The method according to claim 15 wherein said host cell is selected from bacteria, yeast, fungi, insect or mammalian cells.

28. The method according to claim 27 wherein said host cell is *E. coli*.

* * * * *